(12) United States Patent
Coulibaly

(10) Patent No.: US 10,294,280 B2
(45) Date of Patent: May 21, 2019

(54) CONSTRAINED PROTEINS AND USES THEREFOR

(71) Applicant: Monash University, Clayton, Victoria (AU)

(72) Inventor: Fasseli Joseph Coulibaly, Melbourne (AU)

(73) Assignee: Monash University, Victoria (AU)

( * ) Notice: Subject to any disclaimer, the term of this patent is extended or adjusted under 35 U.S.C. 154(b) by 0 days.

(21) Appl. No.: 15/327,759

(22) PCT Filed: Jul. 21, 2015

(86) PCT No.: PCT/AU2015/050408
§ 371 (c)(1),
(2) Date: Jan. 20, 2017

(87) PCT Pub. No.: WO2016/011501
PCT Pub. Date: Jan. 28, 2016

(65) Prior Publication Data
US 2017/0204143 A1    Jul. 20, 2017

(30) Foreign Application Priority Data

Jul. 21, 2014   (AU) ................................. 2014902814

(51) Int. Cl.
*C07K 14/005* (2006.01)
*A61K 39/12* (2006.01)
*A61K 39/00* (2006.01)

(52) U.S. Cl.
CPC ............ *C07K 14/005* (2013.01); *A61K 39/12* (2013.01); *A61K 2039/6075* (2013.01);
(Continued)

(58) Field of Classification Search
None
See application file for complete search history.

(56) References Cited

U.S. PATENT DOCUMENTS 7,674,606 B2    3/2010   Chao et al.
2017/0204143 A1*   7/2017   Coulibaly ............ C07K 14/005

FOREIGN PATENT DOCUMENTS

EP       1582589 A1    10/2005
WO    2008105672 A1     9/2008
WO    2011160177 A1    12/2011

OTHER PUBLICATIONS

Chen et al. (Journal of Virology. Jun. 2011; 85 (12): 6077-6081).*
(Continued)

*Primary Examiner* — Shanon A. Foley
(74) *Attorney, Agent, or Firm* — Honigman LLP; Femando Alberdi; Jonathan P. O'Brien

(57) ABSTRACT

A fusion protein comprising an N-terminal portion and a C-terminal portion, wherein the N-terminal portion is a heterologous protein of interest which includes membrane proteins and antigens and the C-terminal portion is a polyhedrin targeting peptide which is derived from cypovirus polyhedrin and binds to cypovirus polyhedrin. The polyhedrin targeting peptide is described as a C-terminal portion of cypovirus polyhedrin and as C-terminal portion of cypovirus polyhedrin absent all or part of the N-terminal H1 helix sequence. Vectors and cells capable of expressing the fusion proteins are also provided. The fusion proteins fold with cypovirus polyhedrin to form modified complexes, polyhedra/microcubes useful in myriad applications, including as a platform technology for prophylactic or therapeutic vaccinations, therapeutics and diagnostics, including vaccines, therapeutics and diagnostics etc. employing membrane proteins.

14 Claims, 43 Drawing Sheets

Specification includes a Sequence Listing.

(52) U.S. Cl.
CPC .............. *C12N 2720/12034* (2013.01); *C12N 2760/16134* (2013.01); *Y02A 50/386* (2018.01)

(56) References Cited

OTHER PUBLICATIONS

Cheng et al. (Journal of General Virology. 2014; 95: 1532-1538).*
Sequence alignment of SEQ ID No. 12 with Geneseq database access No. ADY52246 Mar. 2005.*
Sequence alignment of SEQ ID No. 13 with Geneseq database access No. ADY52246 Mar. 2005.*
Sequence alignment of SEQ ID No. 14 with Geneseq database access No. ADY52246 Mar. 2005.*
Ohtsuka et al. (NSTI-Nanotech 2010; 3: 292-295).*
Ijiri, H. et al. "Structure-based targeting of bioactive proteins into cypovirus polyhedra and application to immobilized cytokines for mammalian cell culture." Biomaterials, 2009, vol. 30, pp. 4297-4308.
Mori, H. et al. "Application of Insect Virus Polyhedra to Protein Nanocontainers," NSTI-Nanotech, 2010, vol. 3, pp. 254-257.
Matsumoto, G. et al. "Bone regeneration by polyhedra microcrystals from silkworm virus," Scientific Reports, 2012, vol. 2, Article: 935 (pp. 1-7).
Mori, H. et al. "Immobilization of Bioactive Fibroblast Growth Factor-2 into Cubic Proteinous Microcrystals (Bombyx mori Cypovirus Polyhedra) That Are Insoluable in a Physiological Cellular Environment," The Journal of Biological Chemistry, 2007, vol. 282, No. 23, pp. 17289-17296.
Ikeda, K. et al. "Immobilization of diverse foreign proteins in viral polyhedra and potential application for protein microarrays," Proteomics, 2006, vol. 6, pp. 54-66.
Coulibaly, F. et al. "The molecular organization of cypovirus polyhedra," Nature, 2007, vol. 446, pp. 97-101.

* cited by examiner

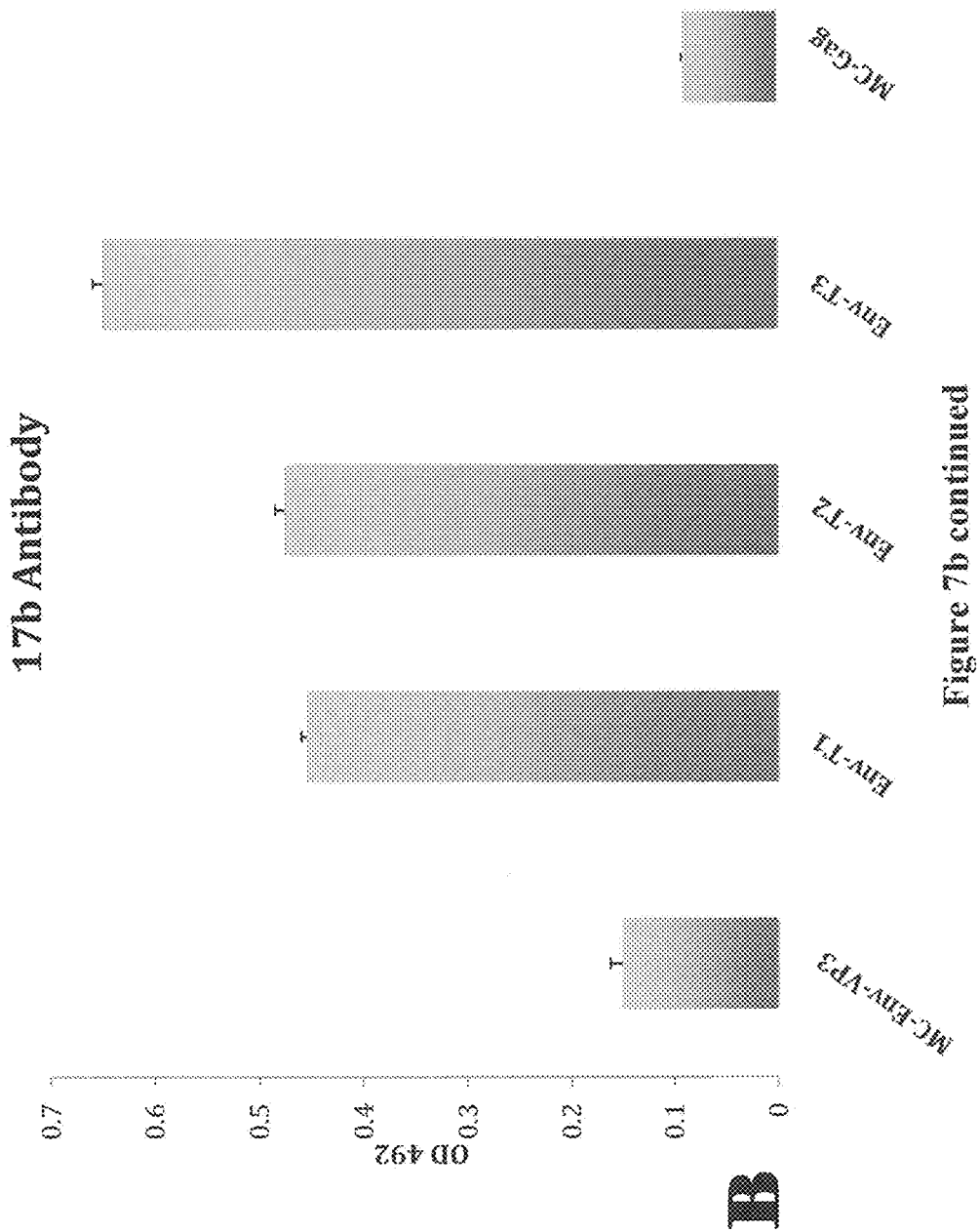

pFastBac-Mel-PH14 (815nt)

CTCGAG
atgaaattcttagtcaacgttgcccttgtttttatggtcgtatacattcttacatctatgccATG a
c agc ggcggcggcggcagcggcagc
GGACGCGAACAAAGACTATTCAATAGCGAG
CAATACAACTATAACAAC
AGCTTGAACGGAGAAGTGAGCGTGTGGGTATACGCATACTACTCAGACGGGTCTGTAC
TCGTAATCAACAAGAACTCGCAATACAAGGTTGGCATTTCAGAGACATTCAAGGCACT
TAAGGAATATCGCAAGGGACAACACAACGACTCTTACGATGAGTATGAAGTGAATCAG
AGCATCTACTATCCTAACGGCGGTGACGCTCGCAAATTCCACTCGAATGCTAAACCACG
CGCGATCCAGATCATCTTCAGCCCTAGTGTGAATGTGCGTACTATCAAGATGGCTAAA
GGTAACGCGGTATCCGTGCCCGATGAGTACTTACAGCGATCTCACCCATGGGAAGCGAC
CGGAATCAAGTACCGCAAGATTAAGAGAGACGGGGAAATCGTTGGTTACAGCCATTAC
TTCGAACTACCCCATGAATACAACTCCATCTCCCTAGCGGTAAGTGGTGTACATAAGA
ACCCATCATCATACAATGTCGGATCAGCACATAACGTAATGGACGTCTTCCAATCATG
CGACTTGGCTCTCAGATTCTGCAACCGCTACTGGGCCGAACTCGAATTGGTGAACCACT
ACATTTCGCCGAACGCCTACCCATACCTCGATATCAACAATCATAGCTATGGAGTAGCT
CTGAGTAACCGTCAG
*TAATAA*
GCATGC (SEQ ID NO: 1)

Figure 14A pFastBac-Mel-PH24 (785nt)

CTCGAG
atgaaattcttagtcaacgttgcccttgtttttatggtcgtatacattcttacatctatgccATG a
c agc ggcggcggcggcagcggcagc
CAATACAACTATAACAAC
AGCTTGAACGGAGAAGTGAGCGTGTGGGTATACGCATACTACTCAGACGGGTCTGTAC
TCGTAATCAACAAGAACTCGCAATACAAGGTTGGCATTTCAGAGACATTCAAGGCACT
TAAGGAATATCGCAAGGGACAACACAACGACTCTTACGATGAGTATGAAGTGAATCAG
AGCATCTACTATCCTAACGGCGGTGACGCTCGCAAATTCCACTCGAATGCTAAACCACG
CGCGATCCAGATCATCTTCAGCCCTAGTGTGAATGTGCGTACTATCAAGATGGCTAAA
GGTAACGCGGTATCCGTGCCCGATGAGTACTTACAGCGATCTCACCCATGGGAAGCGAC
CGGAATCAAGTACCGCAAGATTAAGAGAGACGGGGAAATCGTTGGTTACAGCCATTAC
TTCGAACTACCCCATGAATACAACTCCATCTCCCTAGCGGTAAGTGGTGTACATAAGA
ACCCATCATCATACAATGTCGGATCAGCACATAACGTAATGGACGTCTTCCAATCATG
CGACTTGGCTCTCAGATTCTGCAACCGCTACTGGGCCGAACTCGAATTGGTGAACCACT
ACATTTCGCCGAACGCCTACCCATACCTCGATATCAACAATCATAGCTATGGAGTAGCT
CTGAGTAACCGTCAG
*TAATAA*
GCATGC (SEQ ID NO: 2)

Figure 14B pFastBac-Mel-PH30 (767nt)

CTCGAG
atgaaattcttagtcaacgttgcccttgtttttatggtcgtatacattcttacatctatgccATG G
C AGC ggcggcggcggcagcggcagc
AGCTTGAACGGAGAAGTGAGCGTGTGGGTATACGCATACTACTCAGACGGGTCTGTAC
TCGTAATCAACAAGAACTCGCAATACAAGGTTGGCATTTCAGAGACATTCAAGGCACT
TAAGGAATATCGCAAGGGACAACACAACGACTCTTACGATGAGTATGAAGTGAATCAG
AGCATCTACTATCCTAACGGCGGTGACGCTCGCAAATTCCACTCGAATGCTAAACCACG
CGCGATCCAGATCATCTTCAGCCCTAGTGTGAATGTGCGTACTATCAAGATGGCTAAA
GGTAACGCGGTATCCGTGCCCGATGAGTACTTACAGCGATCTCACCCATGGGAAGCGAC
CGGAATCAAGTACCGCAAGATTAAGAGAGACGGGGAAATCGTTGGTTACAGCCATTAC
TTCGAACTACCCCATGAATACAACTCCATCTCCCTAGCGGTAAGTGGTGTACATAAGA
ACCCATCATCATACAATGTCGGATCAGCACATAACGTAATGGACGTCTTCCAATCATG
CGACTTGGCTCTCAGATTCTGCAACCGCTACTGGGCCGAACTCGAATTGGTGAACCACT
ACATTTCGCCGAACGCCTACCCATACCTCGATATCAACAATCATAGCTATGGAGTAGCT
CTGAGTAACCGTCAG
TAATAA
GCATGC (SEQ ID NO: 3)

Figure 14C

Env construct with flanking NcoI restriction sites
2485nt ccatg;AAAAATTGTGGGTCACAGTCTATTATGGGGTACCTGTGTGGAAGGAAGCAACCACCACTCTATT
TTGTGCATCAGATGCTAAAGCATATGATACAGAGGTACATAA
TGTTTGGGCCACACATGCCTGTGTACCCACAGACCCCAACCCACAAGAAG
TAGTATTGGAAAATGTGACAGAAAATTTTAACATGTGGAAAAATAACATG
GTAGAACAGATGCATGAGGATATAATCAGTTTATGGGATCAAAGCCTAAA
GCCATGTGTAAAATTAACCCCACTCTGTGTTACTTTAAATTGCACTGATT
TGAGGAATGTTACTAATATCAATAATAGTAGTGAGGGAATGAGAGGAGAA
ATAAAAACTGCTCTTTCATATCACCACAAGCATAAGAGATAAGGTGAA
GAAAGACTATGCACTTTTTTATAGACTTGATGTAGTACCAATAGATAATG
ATAATACTAGCTATAGGTTGATAAATTGTAATACCTCAACCATTACACAG
GCCTGTCCAAAGGTATCCTTTGAGCCAATTCCCATACATTATTGTACCCC
GGCTGGTTTTGCGATTCTAAAGTGTAAAGATAAGAAGTTCAATGGAACAG
GGCCATGTAAAAATGTCAGCACAGTACAATGTACACATGGAATTAGGCCA
GTAGTGTCAACTCAACTGCTGTTAAATGGCAGTCTAGCAGAAGAAGAGGT
AGTAATTAGATCTAGTAATTTCACAGACAATGCAAAAAACATAATAGTAC
AGTTGAAAGAATCTGTAGAAATTAATTGTACAAGACCCAACAACAATACA
AGGAAAAGTATACATATAGGACCAGGAAGAGCATTTTATACAACAGGAGA
CATAATAGGAGATATAAGACAAGCACATTGCAACATTAGTAGAACAAAAT
GGAATAACACTTTAAATCAAATAGCTACAAAATTAAAAGAACAATTTGGG
AATAATAAAACAATAGTCTTTAATCAATCCTCAGGAGGGGACCCAGAAAT
TGTAATGCACAGTTTTAATTGTGGAGGGGAATTTTTCTACTGTAATTCAA
CACAACTGTTTAATAGTACTTGGAATTTTAATGGTACTTGGAATTTAACA
CAATCGAATGGTACTGAAGGAAATGACACTATCACACTCCCATGTAGAAT
AAAACAAATTATAAACATGTGGCAAGAAGTAGGAAAAGCAATGTATGCCC
CTCCCATCAGAGGACAAATTAGATGTTCATCAAATATTACAGGGCTGATA
TTAACAAGAGATGGTGGAAATAACCACAATAATGATACCGAGACCTTTAG
ACCTGGAGGAGGAGATATGAGGGACAATTGGAGAAGTGAATTATATAAAT
ATAAAGTAGTAAAAATTGAACCATTAGGAGTAGCACCCACCAAGGCAAAG
AGAAGAGTGGTGCAGAGAGAAAACGGTGCAGTGGGAACAATAGGAGCTAT
GTTCCTTGGGTTCTTGGGAGCAGCAGGAAGCACTATGGGCGCAGCGTCAA
TAACGCTGACGGTACAGGCCAGACTATTATTGTCTGGTATAGTGCAACAG
CAGAACAACTTGCTGAGGGCTATTGAGGCGCAACAGCATCTGTTGCAACT
CACAGTCTGGGGCATCAAGCAGCTCCAGGCAAGAGTCCTGGCTGTGGAAA
GATACCTAAGGGATCAACAGCTCCTAGGGATTTGGGGTTGCTCTGGAAAA
CTCATCTGCACCACTGCTGTGCCTTGGAATGCTAGTTGGAGTAATAAATC
TCTGGAACAGATTTGGAATAACATGACCTGGATGGAGTGGGACAGAGAAA
TTAACAATTACACAAGCTTAATACACTCCTTAATTGAAGAATCGCAAAAC
CAGCAAGAAAAGAATGAACAAGAATTATTGGAATTAGATAAATGGGCAAG
TTTGTGGAATTGGTTTAACATAACAAATTGGCTGTGGTATATAAAATTAT
TCATAATGATAGTAGGAGGCTTGGTAGGTTTAAGAATAGTTTTTGCTGTA
CTTTCTATAGTGAATAGAGTTAGGCAGGGATATTCACCATTATCGTTTCA
GACCCACCTCCCAATCCCGAGGGGACCCGACAGGCCCGAAGGAATAGAAG
AAGAAGGTGGAGAGAGAGACAGAGACAGATCCATTCGATTAGTGAACGGA
TCCTTAGCACTTATCTGGGACGATCTGCGGAGCCTGTGCCTCTTCAGCTA
CCACCGCTTGAGAGACTTACTCTTGATTGTAACGAGGATTGTGGAACTTC
TGGGACGCAGGGGGTGGGAAGCCCTCAAATATTGGTGGAATCTCCTACAG
TATTGGAGTCAGGAACTAAAGAATAGTGCTGTTAACTTGCTCAATGCCAC
AGCCATAGCAGTAGCTGAGGGGACAGATAGGGTTATAGAAGTATTACAAG
CAGCTTATAGAGCTATTCGCCACATACCTAGAAGAATAAGACAGGGCTTG
GAAAGGATTTTGCT
ccatgg (SEQ ID NO: 4)

Figure 15A

Translation (Frame +3)
MDEKLWVTVYYGVPVWKEATTTLFCASDAKAYDTEVHNVWATHACVPTDPNPQEVVLERV
TENFNMWKNNMVEQMHEDIISLWDQSLKPCVKLTPLCVTLNCTDLRNVTNINNSSEGMRG
EIKNCSFNITTSIRDKVKKDYALFYRLDVVPIDNDNTSYRLINCNTSTITQACPKVSFEP
IPIHYCTPAGFAILKCKDKKFNGTGPCKRVSTVQCTHGIRPVVSTQLLLNGSLAEEEVVI
RSSNFTDNAKNIIVQLKESVEINCTRPNNNTRKSIHIGPGRAFYTTGDIIGDIRQAHCNI
SPTKWNNTLNQIATKLKEQFGNNKTIVFNQSSGGDPEIVMHSFNCGGEFFYCNSTQLFNS
TWNFRGTWNLTQSNGTEGNDTITLPCRIKQIINMWQEVGKAMYAPPIRGQIRCSSNITGL
ILTRDGGNNHNNDTETFRPGGGDMRDNWPSELYKYKVVKIEPLGVAPTKAKPRVVQREKR
AVGTIGAMFLGFLGAAGSTMGAASITLTVQARLLLSGIVQQQNNLLRAIEAQQHLLQLTV
WGIKQLQAPVLAVERYLRDQQLLGIWGCSGKLICTTAVPWNASWSNKSLEQIWNNMTWME
WDREINNYTSLIHSLIEESQNQQEKNEQELLELDKWASLWNWFNITNWLWYIKLFIMIVG
GLVGLPIVFAVLSIVNRVRQGYSPLSFQTHLPIPRGPDRPEGIEEEGGERDRDRSIRLVN
GSLALIWDDLRSLCLFSYHRLRDLLLIVTRIVELLGRRGWEALKYWWNLLQYWSQELKNS
AVNLLNATAIAVAEGTDRVIEVLQAAYRAIRHIPRRIRQGLERILL (SEQ ID NO: 5)
HG (last aa brought by linker: ggX is Gly irrespective of X)

Figure 15B

Final constructs in pFastBac/pFastBac-Dual after restriction digest with NcoI and ligation of the Env-FL construct pFastBac-Mel-PH14-Env

XhoI in green
NcoI in red
SphI in blue

```
CTCGAG
atgaaattcttagtcaacgttgcccttgtttttatggtcgtatacattccttacatctatgccATG G
AAAAATGTGGGTCACAGTCTATTATGGGTACCTGTGTGGAAGGAAGCAACCACC
ACTCTATTTTGTGCATCAGATGCTAAAGCATATGATACAGAGGTACATAA
TGTTTGGGCCACACATGCCTGTGTACCCACAGACCCCAACCCACAAGAAG
TAGTATTGGAAAATGTGACAGAAAATTTTAACATGTGGAAAAATAACATG
GTAGAACAGATGCATGAGGATATAATCAGTTTATGGGATCAAAGCCTAAA
GCCATGTGTAAAATTAACCCCACTCTGTGTTACTTTAAATTGCACTGATT
TGAGGAATGTTACTAATATCAATAATAGTAGTCAGGGAATGAGAGGAGAA
ATAAAAAACTGCTCTTTCAATATCACCACAAGCATAAGAGATAAGGTGAA
GAAAGACTATGCACTTTTTTATAGACTTGATGTAGTACCAATAGATAATG
ATAATACTAGCTATAGGTTGATAAATTGTAATACCTCAACCATTACACAG
GCCTGTCCAAAGGTATCCTTTGAGCCAATTCCCATACATTATTGTACCCC
GGCTGGTTTTGCGATTCTAAAGTGTAAAGATAAGAAGTTCAATGGAACAG
GGCCATGTAAAAATGTCAGCACAGTACAATGTACACATGGAATTAGGCCA
GTAGTGTCAACTCAACTGCTGTTAAATGGCAGTCTAGCAGAAGAAGAGGT
AGTAATTAGATCTAGTAATTTCACAGACAATGCAAAAAACATAATAGTAC
AGTTGAAAGAATCTGTAGAAATTAATTGTACAAGACCCCAACAACAATACA
AGGAAAAGTATACATATAGGACCAGGAAGAGCATTTTATACAACAGGAGA
CATAATAGGAGATATAAGACAAGCACATTGCAACATTAGTAGAACAAAAT
GGAATAACACTTTAAATCAAATAGCTACAAAATTAAAAGAACAATTTGGG
AATAATAAAACAATAGTCTTTAATCAATCCTCAGGAGGGGACCCCAGAAAT
TGTAATGCACAGTTTTAATTGTGGAGGGGAATTTTTCTACTGTAATTCAA
CACAACTGTTTAATAGTACTTGGAATTTTAATGGTACTTGGAATTTAACA
CAATCGAATGGTACTGAAGGAAATGACACTATCACACTCCCATGTAGAAT
AAAACAAATTATAAACATGTGGCAAGAAGTAGGAAAAGCAATGTATGCCC
CTCCCATCAGAGGACAAATTAGATGTTCATCAAATATTACAGGGCTGATA
TTAACAAGAGATGGTGGAAATAACCACAATAATGATACTGAGACCTTTAG
ACCTGGAGGAGGAGATATGAGGGACAATTGAGAAGTGAATTATATAAAT
ATAAAGTAGTAAAAATTGAACCATTAGGAGTAGCACCCACCAAGGCAAAG
AGAAGAGTGGTGCAGAGAGAAACCGGTGCAGTGGGAACAATAGGAGCTAT
GTTCCTTGGGTTCTTGGGAGCAGCAGGAAGCACTATGGGCGCAGCGTCAA
TAACGCTGACGGTACAGGCCAGACTATTATTGTCTGGTATAGTGCAACAG
CAGAACAACTTGCTGAGGGCTATTGAGGCGCAACAGCATCTGTTGCAACT
CACAGTCTGGGGCATCAAGCAGCTCCAGGCAAGAGTCCTGGCTGTGGAAA
GATACCTAAAGGATCAACAGCTCCTAGGGATTTGGGGTTGCTCTGGAAAA
CTCATCTGCACCACTGCTGTGCCTTGGAATGCTAGTTGGAGTAATAAATC
TCTGGAACAGATTTGGAATAACATGACCTGGATGGAGTGGGACAGAGAAA
TTAACAATTACACAAGCTTAATACACTCCTTAATTGAAGAATCGCAAAAC
CAGCAAGAAAAGAATGAACAAGAATTATTGGAATTAGATAAATGGGCAAG
TTTGTGGAATTGGTTTAACATAACAAATTGGCTGTGGTATATAAAATTAT
TCATAATGATAGTAGGAGGCTTGGTAGGTTTAAGAATAGTTTTTGCTGTA
CTTTCTATAGTGAATAGAGTTAGGCAGGGATATTCACCATTATCGTTTCA
GACCCACCTCCCAATCCCGAGGGGACCCGACAGCCCGAAGGAATAGAAG
AAGAAGGTGGAGAGAGAGACAGAGACAGATCCATTCGATTAGTGAACGGA
TCCTTAGCACTTATCTGGGACGATCTGCGGAGCCTGTGCCTCTTCAGCTA
CCACCGCTTGAGAGACTTACTCTTGATTGTAACGAGGATTGTGGAACTTC
TGGGACGCAGGGGTGGGAAGCCCTCAAATATCGGTGGAATCTCCTACAG
TATTGGAGTCAGGAACTAAAGAATAGTGCTGTTAACTTGCTCAATGCCAC
```

Figure 16A

```
AGCCATAGCAGTAGCTGAGGGGACAGATAGGGTTATAGAAGTATTACAAG
CAGCTTATAGAGCTATTCGCCACATACCTAGAAGAATAAGACAGGGCTTG
GAAAGGATTTTCGCTcatgg
c agc ggcggcggcagcggcagc
GGACGCGAACAAAGACTATTCAATAGCGAG
CAATACAACTATAACAAC
AGCTTGAACGGAGAAGTGAGCGTGTGGGTATACGCATACTACTCAGACGGGTCTGTACTCGTAATCAACAAGAACTCG
CAATACAAGGTTGGCATTTCAGAGACATTCAAGGCACTTAAGGAATATCGCAAGGGACAACACAACGACTCTTACGAT
GAGTATGAAGTGAATCAGAGCATCTACTATCCTAACGGCGGTGACGCTCGCAAATTCCACTCGAATGCTAAACCACGC
GCGATCCAGATCATCTTCAGCCCTAGTGTGAATGTGCGTACTATCAAGATGGCTAAAGGTAACGCGGTATCCGTGCCC
GATGAGTACTTACAGCGATCTCACCCATGGGAAGCGACCGGAATCAAGTACCGCAAGATTAAGAGAGACGGGGAAAT
CGTTGGTTACAGCCATTACTTCGAACTACCCCATGAATACAACTCCATCCCCTAGCGGTAAGTGGTGTACATAAGAA
CCCATCATCATACAATGTCGGATCAGCACATAACGTAATGGACGTCTTCCAATCATGCGACTTGGCTCTCAGATTCTG
CAACCGCTACTGGGCCGAACTCGAATTGGTGAACCACTACATTTCGCCGAACGCCTACCCATACCTCGATATCAACAA
TCATAGCTATGGAGTAGCTCTGAGTAACCGTCAG
TAATAA
GCATGC (SEQ ID NO: 6)
```

Figure 16A (cont.)

Translation (1092 AA – N-terminal melittin in blue-underlined; linker in bold (HGS GGGGSGS); PH14-tag in red-underlined)

```
MKFLVNVAL VFMVVYISYI YAMEKLWVTV YYGVPVWKEA TTTLFCASDA KAYDTEVHNV
WATHACVPTD PNPQEVVLEN VTENFNMWKN NMVEQMHEDI ISLWDQSLKP CVKLTPLCVT
LNCTDLRNVT NNNSSSGMR GEIKNCSFNI TTSIRDKVKK DYALFYRLDV VPIDNDNTSY
RLINCNTSTI TQACPKVSFE PIPIHYCTPA GFAILKCKDK KFNGTGPCKN VSTVQCTHGI
RPVVSTQLLL NGSLAEEEVV IRSSNFTDNA KNIIVQLKES VEINCTRPNN NTRKSIHIGP
GRAFYTTGDI IGDIRQAHCN ISRTKWNNTL NQTATKLKEQ FGNNKTTVFN QSSGGDPEIV
MHSFNCGGEF FYCNSTQLFN STWRFNGTWN LTQSNGTEGN DTITLPCRIK QIINMWQEVG
KAMYAPPIRG QIRCSSNITG LILTRDGGNN NRDTETFRP GGGDMRDNWR SELYKYKVVK
IEPLGVAPTK AKRRVVQREK RAVGTIGAMF LGFLGAAGST MGAASITLTV QARLLLSGIV
QQQNNLLRAI EAQQHLLQLT VWGIKQLQAR VLAVERYLRD QQLLGIWGCS GKLICTTAVP
WNASWSNKSL EQIWNNMTWM EWDREINNYT SLIHSLIEES QNQQEKNEQE LLELDKWASL
WNWFNITNWL WYIKLFIMIV GGLVGLRIVF AVLSIVNRVR QGYSPLSFQT RLPIPRGPDR
PEGIEEEGGE RDRDRSIRLV NGSLALIWDD LRSLCLFSYH RLRDLLLIVT RIVELLGRRG
WEALKYWWNL LQYWSQELKN SAVRLLNATA IAVAEGTDRV IEVLQAAYRA IRHIPRRIRQ
GLERILLRGS GGGGSGSGRS GRLFYSEQYN YNNSLNGEVS YWYYAKYSDG SVLVIHNSQ
YRVGISEKFK ALKEYDRSQH NGSYDEYRVR SGIKYENGGD AKKFNBRAKP NAIQIIFSPS
VNVKIRMAK GNAVSVRDKY LQRSHFWEAT GIKYPKINRD GGIVGISRKF RLPKRENSIS
LAVSGYHRE SSYNVGSAHR VRDVRQHEDL ALRFCNRYWA KLRLVNRYIS PNAIPYLDIN
NHSYSYALRR RQ (SEQ ID NO: 7)
```

Figure 16B pFastBac-Mel-PH24-Env

XhoI in green
NcoI in red
SphI in blue

CTCGAG
atgaaattcttagtcaacgttgcccttgttttatggtcgtatacattcttacatctatgccATG G
AAAAATTGTGGGTCACAGTCTATTATGGGGTACCTGTGTGGAAGGAAGCAACCACC
ACTCTATTTTGTGCATCAGATGCTAAAGCATATGATACAGAGGTACATAA
TGTTTGGGCCACACATGCCTGTGTACCCACAGACCCCAACCCACAAGAAG
TAGTATTGGAAAATGTGACAGAAAATTTTAACATGTGGAAAAATAACATG
GTAGAACAGATGCATGAGGATATAATCAGTTTATGGGATCAAAGCCTAAA
GCCATGTGTAAAATTAACCCCACTCTGTGTTACTTTAAATTGCACTGATT
TGAGGAATGTTACTAATATCAATAATAGTAGTGAGGGAATGAGAGGAGAA
ATAAAAAACTGCTCTTTCAATATCACCACAAGCATAAGAGATAAGGTGAA
GAAAGACTATGCACTTTTTTATAGACTTGATGTAGTACCAATAGATAATG
ATAATACTAGCTATAGGTTGATAAATTGTAATACCTCAACCATTACACAG
GCCTGTCCAAAGGTATCCTTTGAGCCAATTCCCATACATTATTGTACCCC
GGCTGGTTTTGCGATTCTAAAGTGTAAAGATAAGAAGTTCAATGGAACAG
GGCCATGTAAAAATGTCAGCACAGTACAATGTACACATGGAATTAGGCCA
GTAGTGTCAACTCAACTGCTGTTAAATGGCAGTCTAGCAGAAGAAGAGGT
AGTAATTAGATCTAGTAATTTCACAGACAATGCAAAAACATAATAGTAC
AGTTGAAAGAATCTGTAGAAATTAATTGTACAAGACCCAACAACAATACA
AGGAAAAGTATACATATAGGACCAGGAAGAGCATTTTATACAACAGGAGA
CATAATAGGAGATATAAGACAAGCACATTGCAACATTAGTAGAACAAAAT
GGAATAACACTTTAAATCAAATAGCTACAAAATTAAAAGAACAATTTGGG
AATAATAAAACAATAGTCTTTAATCAATCCTCAGGAGGGACCCAGAAAT
TGTAATGCACAGTTTTAATTGTGGAGGGGAATTTTTCTACTGTAATTCAA
CACAACTGTTTAATAGTACTTGGAATTTTAATGGTACTTGGAATTTAACA
CAATCGAATGGTACTGAAGGAAATGACACTATCACACTCCCATGTAGAAT
AAAACAAATTATAAACATGTGGCAAGAAGTAGGAAAAGCAATGTATGCCC
CTCCCATCAGAGGACAAATTAGATGTTCATCAAATATTACAGGGCTGATA
TTAACAAGAGATGGTGGAAATAACCACAATAATGATACCGAGACCTTTAG
ACCTGGAGGAGGAGATATGAGGGACAATTGGAGAAGTGAATTATATAAAT
ATAAAGTAGTAAAAATTGAACCATTAGGAGTAGCACCCACCAAGGCAAAG
AGAAGAGTGGTGCAGAGAGAAACCGGTGCAGTGGGAACAATAGGAGCTAT
GTTCCTTGGGTTCTTGGGAGCAGCAGGAAGCACTATGGGCGCAGCGTCAA
TAACGCTGACGGTACAGGCCAGACTATTATTGTCTGGTATAGTGCAACAG
CAGAACAACTTGCTGAGGGCTATTGAGGCGCAACAGCATCTGTTGCAACT
CACAGTCTGGGGCATCAAGCAGCTCCAGGCAAGAGTCCTGGCTGTGGAAA
GATACCTAAGGGATCAACAGCTCCTAGGGATTTGGGGTTGCTCTGGAAAA
CTCATCTGCACCACTGCTGTGCCTTGGAATGCTAGTTGGAGTAATAAATC
TCTGGAACAGATTTGGAATAACATGACCTGGATGGAGTGGGACAGAGAAA
TTAACAATTACACAAGCTTAATACACTCCTTAATTGAAGAATCGCAAAAC
CAGCAAGAAAAGAATGAACAAGAATTATTGGAATTAGATAAATGGGCAAG
TTTGTGGAATTGGTTTAACATAACAAATTGGCTGTGGTATATAAAATTAT
TCATAATGATAGTAGGAGGCTTGGTAGGTTTAAGAATAGTTTTTGCTGTA

Figure 17A

```
CTTTCTATAGTGAATAGAGTTAGGCAGGGATATTCACCATTATCGTTTCA
GACCCACCTCCCAATCCCGAGGGGACCCGACAGGCCCGAAGGAATAGAAG
AAGAAGGTGGAGAGAGAGACAGAGACAGATCCATTCGATTAGTGAACGGA
TCCTTAGCACTTATCTGGGACGATCTGCGGAGCCTGTGCCTCTTCAGCTA
CCACCGCTTGAGAGACTTACTCTTGATTGTAACGAGGATTGTGGAACTTC
TGGGACGCAGGGGGTGGGAAGCCCTCAAATATTGGTGGAATCTCCTACAG
TATTGGAGTCAGGAACTAAAGAATAGTGCTGTTAACTTGCTCAATGCCAC
AGCCATAGCAGTAGCTGAGGGGACAGATAGGGTTATAGAAGTATTACAAG
CAGCTTATAGAGCTATTCGCCACATACCTAGAAGAATAAGACAGGGCTTG
GAAAGGATTTTGCTccatgg
c agc ggcggcggcagcggcagc
CAATACAACTATAACAAC
AGCTTGAACGGAGAAGTGAGCGTGTGGGTATACGCATACTACTCAGACGGGTCTGTAC
TCGTAATCAACAAGAACTCGCAATACAAGGTTGGCATTTCAGAGACATTCAAGGCACT
TAAGGAATATCGCAAGGGACAACACAACGACTCTTACGATGAGTATGAAGTGAATCAG
AGCATCTACTATCCTAACGGCGGTGACGCTCGCAAATTCCACTCGAATGCTAAACCACG
CGCGATCCAGATCATCTTCAGCCCAGTGTGAATGTGCGTACTATCAAGATGGCTAAA
GGTAACGCGGTATCCGTGCCCGATGAGTACTTACAGCGATCTCACCCATGGGAAGCGAC
CGGAATCAAGTACCGCAAGATTAAGAGAGACGGGGAAATCGTTGGTTACAGCCATTAC
TTCGAACTACCCCATGAATACAACTCCATCTCCCTAGCGGTAAGTGGTGTACATAAGA
ACCCATCATCATACAATGTCGGATCAGCACATAACGTAATGGACGTCTTCCAATCATG
CGACTTGGCTCTCAGATTCTGCAACCGCTACTGGGCCGAACTCGAATTGGTGAACCACT
ACATTCGCCGAACGCCTACCCATACCTCGATATCAACAATCATAGCTATGGAGTAGCT
CTGAGTAACCGTCAG
TAATAA
GCATGC (SEQ ID NO: 8)
```

Figure 17A (cont.)

Translation (1082 AA – melittin in blue-underlined; linker in bold (HGS GGGGSGS); PH24-tag in red=underlined)

(SEQ ID NO: 9)

Figure 17B pFastBac-Mel-PH30-Env

XhoI in green
NcoI in red
SphI in blue

CTCGAG
atgaaattcttagtcacgttgcccttgttttatggtcgtatacattcttacatctatgccATG G
AAAAATGTGGGTCACAGTCTATTATGGGTACCTGTGTGGAAGGAAGCAACCACC
ACTCTATTTTGTGCATCAGATGCTAAAGCATATGATACAGAGGTACATAA
TGTTTGGGCCACACATGCCTGTGTACCCACAGACCCCAACCCACAAGAAG
TAGTATTGGAAAATGTGACAGAAAATTTTAACATGTGGAAAAATAACATG
GTAGAACAGATGCATGAGGATATAATCAGTTTATGGGATCAAAGCCTAAA
GCCATGTGTAAAATTAACCCCACTCTGTGTTACTTTAAATTGCACTGATT
TGAGGAATGTTACTAATATCAATAATAGTAGTGAGGGAATGAGAGGAGAA
ATAAAAAACTGCTCTTTCAATATCACCACAAGCATAAGAGATAAGGTGAA
GAAAGACTATGCACTTTTTTATAGACTTGATGTAGTACCAATAGATAATG
ATAATACTAGCTATAGGTTGATAAATTGTAATACCTCAACCATTACACAG
GCCTGTCCAAAGGTATCCTTTGAGCCAATTCCCATACATTATTGTACCCC
GGCTGGTTTTGCGATTCTAAAGTGTAAAGATAAGAAGTTCAATGGAACAG
GGCCATGTAAAAATGTCAGCACAGTACAATGTACACATGGAATTAGGCCA
GTAGTGTCAACTCAACTGCTGTTAAATGGCAGTCTAGCAGAAGAAGAGGT
AGTAATTAGATCTAGTAATTTCACAGACAATGCAAAAAACATAATAGTAC
AGTTGAAAGAATCTGTAGAAATTAATTGTACAAGACCCAACAACAATACA
AGGAAAAGTATACATATAGGACCAGGAAGAGCATTTTATACAACAGGAGA
CATAATAGGAGATATAAGACAAGCACATTGCAACATTAGTAGAACAAAAT
GGAATAACACTTTAAATCAAATAGCTACAAAATTAAAAGAACAATTTGGG
AATAATAAAACAATAGTCTTTAATCAATCCTCAGGAGGGGACCCAGAAAT
TGTAATGCACAGTTTTAATTGTGGAGGGGAATTTTTCTACTGTAATTCAA
CACAACTGTTTAATAGTACTTGGAATTTTAATGGTACTTGGAATTTAACA
CAATCGAATGGTACTGAAGGAAATGACACTATCACACTCCCATGTAGAAT
AAAACAAATTATAAACATGTGGCAAGAAGTAGGAAAAGCAATGTATGCCC
CTCCCATCAGAGGACAAATTAGATGTTCATCAAATATTACAGGGCTGATA
TTAACAAGAGATGGTGGAAATAACCAATAATGATACCGAGACCTTTAG
ACCTGGAGGAGGAGATATGAGGGACAATTGGAGAAGTGAATTATATAAT
ATAAAGTAGTAAAAATTGAACCATTAGGAGTAGCACCCACCAAGGCAAAG
AGAAGAGTGGTGCAGAGAGAAACCGGTGCAGTGGGAACAATAGGAGCTAT
GTTCCTTGGGTTCTTGGGAGCAGCAGGAAGCACTATGGGCGCAGCGTCAA
TAACGCTGACGGTACAGGCCAGACTATTATTGTCTGGTATAGTGCAACAG
CAGAACAACTTGCTGAGGGCTATTGAGGCGCAACAGCATCTGTTGCAACT
CACAGTCTGGGGCATCAAGCAGCTCCAGGCAAGAGTCCTGGCTGTGGAAA
GATACCTAAGGGATCAACAGCTCCTAGGGATTTGGGGTTGCTCTGGAAAA
CTCATCTGCACCACTGCTGTGCCTTGGAATGCTAGTTGGAGTAATAAATC
TCTGGAACAGATTTGGAATAACATGACCTGGATGGAGTGGGACAGAGAAA
TTAACAATTACACAAGCTTAATACACTCCTTAATTGAACAATCGCAAAAC
CAGCAAGAAAAGAATGAACAAGAATTATTGGAATTAGATAAATGGGCAAG
TTTGTGGAATTGGTTTAACATAACAAATTGGCTGTGGTATATAAAATTAT
TCATAATGATAGTAGGAGGCTTGGTAGGTTTAAGAATAGTTTTTGCTGTA
CTTTCTATAGTGAATAGAGTTAGGCAGGGATATTCACCATTATCGTTTCA
GACCCACCTCCCAATCCCGAGGGGACCCGACAGGCCCGAAGGAATAGAAG
AAGAAGGTGGAGAGAGAGACAGAGACAGATCCATTCGATTAGTGAACGGA
TCCTTAGCACTTATCTGGGACGATCTGCGGAGCCTGTGCCTCTTCAGCTA
CCACCGCTTGAGAGACTTACTCTTGATTGTAACGAGGATTGTGGAACTTC
TGGGACGCAGGGGTGGGAAGCCCTCAAATATTGGTGGAATCTCCTACAG
TATTGGAGTCAGGAACTAAAGAATAGTGCTGTTAACTTGCTCAATGCCAC

Figure 18A

```
AGCCATAGCAGTAGCTGAGGGGACAGATAGGGTTATAGAAGTATTACAAG
CAGCTTATAGAGCTATTCGCCACATACCTAGAAGAATAAGACAGGCTTG
GAAAGGATTTTGCTccatgg
c agc ggcggcggcgtcagcggcagc
AGCTTGAACGGAGAAGTGAGCGTGTGGGTATACGCATACTACTCAGACGGGTCTGTACTCGTAATCAACA
AGAACTCGCAATACAAGGTTGGCATTTCAGAGACATTCAAGGCACTTAAGGAATATCGCAAGGGACAACA
CAACGACTCTTACGATGAGTATGAAGTGAATCAGAGCATCTACTATCCTAACGGCGGTGACGCTCGCAAA
TTCCACTCGAATGCTAAACCACGCGCGATCCAGATCATCTTCAGCCCTAGTGTGAATGTGCGTACTATCA
AGATGGCTAAAGGTAACGCGGTATCCGTGCCCGATGAGTACTTACAGCGATCTCACCCATGGGAAGCGAC
CGGAATCAAGTACCGCAAGATTAAGAGAGACGGGGAAATCGTTGGTTACAGCCATTACTTCGAACTACCC
CATGAATACAACTCCATCTCCCTAGCGGTAAGTGGTGTACATAAGAACCCATCATCATACAATGTCGGAT
CAGCACATAACGTAATGGACGTCTTCCAATCATGCGACTTGGCTCTCAGATTCTGCAACCGCTACTGGCC
GAACTCGAATTGGTGAACCACTACATTTCGCCGAACGCCTACCCATACCTCGATATCAACAATCATAGCT
ATGGAGTAGCTCTGAGTAACCGTCAG
TAATAA
GCATGC (SEQ ID NO: 10)
```

Figure 18A (cont.)

Translation (1076 AA – melittin in blue-underlined; linker in bold (HGS GGGGSGS); PH30-tag in red-underlined)

```
MKFLVNVAL VFMVVYISYI YAMDEKLWVTV YYGVPVWKEA TTTLFCASDA KAYDTEVHNV
WATHACVPTD PNPQEVVLEN VTENFNMWKN NMVEQMHEDI ISLWDQSLKP CVKLTPLCVT
LNCTDLRNVT NINNSSEGMR GEIKNCSFNI TTSIRDKVKK DYALFYRLDV VPIDNDNTSY
RLINCNTSTI TQACPKVSFE PIPIHYCTPA GFAILKCKDK KFNGTGPCKN VSTVQCTHGI
RPVVSTQLLL NGSLAEEEVV IRSSNFTDNA KNIIVQLKES VEINCTRPNN NTRKSIHIGP
GRAFYTTGDI IGDIRQAHCN ISPTKWNNTL NQIATKLKEQ FGNNKTIVFN QSSGGDPEIV
MHSFNCGGEF FYCNSTQLFN STWNFNGTWN LTQSNGTEGN DTITLPCRIK QIINMWQEVG
KAMYAPPIRG QIRCSSNITG LILTRDGGNN HNNDTETPRP GGGDMRDNWR SELYKYKVVK
IEPLGVAPTK AKRRVVQREV GAVGTIGAMF LGFLGAAGST MGAASITLTV QARLLSGIV
QQQNNLLRAI EAQQHLLQLT VWGIKQLQAR VLAVERYLRD QQLLGIWGCS GKLICTTAVP
WNASWSNKSL EQIWNNMTWM EWDREINNYT SLIHSLIEES QNQQEKNEQE LLELDKWASL
WNWFNITNWL WYIKLFIMIV GGLVGLRIVF AVLSIVNPVR QGYSPLSFQT HLPIPRGPDR
PEGIEEEGGE RDRDRSIRLV NGSLALIWDD LRSLCLFSYH RLRDLLLIVT RIVELLGRRG
WEALKYWWNL LQYWSQELKN SAVNLLNATA IAVAEGTDRV IEVLQAAYRA IRHIPRRIRQ
GLERILLHGS GGGGSGSRLN GRYSVWYYAY SDGSVLYIN RHSGYKYGIS RTFKALEEYR
KGQHNDSYDE YRVNQSIYYP NSGDARKFNS NAKPRAIQII FSPSYNVRYI KMAEGNAVSY
RDRILQRSHP WEAHGIKYRK IKRDGEIVSY SHYFRLPHEY NSIBLAVSGY HKNPSSYNVG
SAHNVSLVFQ SCDIALRFCN RYWAELELYN HYLSENAYPY LOINNHSYGV ALSNRQ (SEQ ID NO: 11)
```

Figure 18B

HA PR8 sequence:

>NcoI-PR8-FL-NcoI
CCATGGATACAATCTGTATTGGATACCACGCCAATAACTCAACCGACACTGTGGATACTGTC
CTCGAAAAGAACGTGACGGTCACTCACAGTGTCAATTTGTTGGAAGATAGCCACAATGGTA
AACTGTGCAGACTGAAAGGCATTGCCCCTCTGCAACTCGGAAAGTGTAACATTGCTGGATGG
CTGTTGGGTAACCCCGAGTGCGACCCACTTCTCCCTGTCCGCTCGTGGTCCTACATCGTGGA
GACTCCCAATAGCGAGAATGGTATTTGTTACCCAGGCGACTTTATCGACTATGAGGAGCTGC
GCGAGCAGCTCTCATCGGTCAGCTCATTCGAGAGGTTTGAGATCTTTCCCAAGGAATCGAGC
TGGCCAAATCATAACACCAACGGAGTTACTGCAGCTTGCTCCCACGAGGGAAAATCTTCGTT
CTATCGTAATTTGTTGTGGCTGACTGAAAAGGAGGGAAGTTACCCGAAGTTGAAAAACTCCT
ACGTCAATAAGAAGGGTAAAGAAGTGCTGGTTCTCTGGGGCATCCACCATCCTCCGAATTCC
AAGGAACAACAGAACATCTACCAGAACGAAAATGCTTATGTGTCCGTGGTTACCTCCAACT
ACAACAGGCGCTTCACACCAGAGATCGCTGAGCGTCCTAAAGTCCGCGACCAGGCGGGTCG
CATGAATTACTACTGGACCCTGCTGAAGCCGGGTGATACTATTATCTTCGAGGCTAACGGTA
ACCTCATAGCGCCCATGTATGCTTTCGCCTTGTCAAGAGGTTTTGGCAGTGGAATCATTACCT
CTAACGCGTCTATGCATGAGTGCAATACTAAGTGCCAGACACCTCTCGGAGCTATAAACAGC
TCCCTTCCCTATCAAAACATCCACCCAGTCACCATAGGAGAATGTCCTAAGTATGTACGCTC
CGCCAAGTTGAGGATGGTAACGGGCTTGCGTAACACACCCTCGATCCAGAGTAGGGGTCTG
TTCGGAGCAATTGCAGGCTTCATCGAGGGCGGTTGGACGGGTATGATCGATGGCTGGTATGG
CTACCACCATCAAAACGAGCAGGGCAGTGGATACGCCGCAGATCAGAAGTCTACACAAAAC
GCTATCAATGGAATTACCAACAAGGTTAATACCGTTATCGAAAAGATGAATATACAGTTCAC
AGCCGTGGGCAAAGAATTCAACAAGTTGGAAAAACGTATGGAAAACCTTAACAAGAAAGTG
GATGACGGTTTTCTCGACATCTGGACCTACAACGCAGAGCTTCTGGTACTTCTTGAGAACGA
AAGAACCCTGGACTTCCACGACTCGAACGTGAAGAATCTTTACGAAAAGGTAAAGAGTCAA
CTCAAGAACAACGCTAAAGAGATTGGTAACGGTTGTTTCGAATTCTATCACAAGTGCGACAA
CGAATGCATGGAGTCCGTTCGTAACGGTACGTACGACTACCCAAAGTACAGCGAGGAGAGC
AAACTGAACAGAGAAAAAGTAGATGGCGTCAAACTCGAATCAATGGGCATATACCAGATCC
TGGCGATCTACTCTACGGTTGCCTCTTCTCTCGTGCTGCTTGTGTCATTGGGAGCCATAAGTT
TCTGGATGTGCAGCAACGGCTCACTGCAATGTCGTATTTGCATCCATGG (SEQ ID NO: 15)

Figure 19

CONSTRAINED PROTEINS AND USES THEREFOR

The present application claims priority under 35 U.S.C. § 371 to Patent Cooperation Treaty application PCT/AU2015/050408, filed Jul. 21, 2015, which claims the benefit of earlier filed Australian application No. 2014902814, filed Jul. 21, 2014, the entire contents of which are incorporated herein by reference.

Incorporated by reference in its entirety is a computer-readable sequence listing submitted concurrently herewith and identified as follows: One 62.5 KB ASCII (Text) file named "517615 Sequence listing.txt."

FIELD

The present description relates to a platform technology for producing stable and functional proteinaceous biological molecules in modified polyhedra crystals referred to as microcubes for a wide range of applications not limited to screening and diagnostics applications, therapeutics, in vitro culture reagents, tissue repair and vaccination.

BACKGROUND

Bibliographic details of references in the subject specification are also listed at the end of the specification.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Recombinant expression of functional biological molecules and particularly full length membrane proteins for the biotechnology, medical and allied health industry is a challenging endeavour.

Membrane proteins constitute attractive targets for biotechnological applications such as diagnostic, biosensors, stem cell culture and tissue repair and vaccine. However these proteins are extremely difficult to produce compared to their soluble counterparts. The process generally involves detergent solubilisation with the risk of inactivating the protein by denaturation, an increased cost and often incompatibilities with downstream applications. The solution commonly adopted is to express only the soluble portion of the protein of interest but this results in an artificial construct that potentially misses some of the characteristics of the full-length native protein.

Despite much progress in understanding the mechanisms of immunity, vaccines against major pathogens, such as without limitation HIV and *Plasmodium* spp. remain elusive. In recent years, alternative antigen delivery systems have been actively investigated for greater efficacy, safety and ease of production. The most successful of these approaches has been virus-like particles (VLP) relying on self-assembly of viral structural proteins (HBV, papillomavirus). However, many pathogens do not produce such assemblies and there are limitations to the size of the antigens that can be incorporated into VLP scaffolds. The administration of antigens as particles is thought to have a number of advantages. Antigen presenting cells take up particulate antigens preferentially and traffic them to cellular compartments facilitating the production of antibody and cellular responses (see review by Rice-Ficht et al., *Current Opinion in Microbiology*, 13: 106-112, 2010).

There remains a need for a versatile platform technology able to provide stable and functional proteins, including membrane proteins, for myriad applications.

SUMMARY

Each embodiment in this specification is to be applied mutatis mutandis to every other embodiment unless expressly stated otherwise.

The articles "a" and "an" are used herein to refer to one or to more than one (i.e. to at least one) of the grammatical object of the article. By way of example, "a cell" means one cell or more than one cell. Reference to "a protein" means one protein or more than one protein.

Nucleotide and amino acid sequences are referred to in the specification and by sequence identifier number (SEQ ID NO:) that are described further in Table 3.

In one embodiment, the present specification enables a fusion protein comprising an N-terminal portion and a C-terminal portion, wherein the N-terminal portion is a heterologous protein of interest and the C-terminal portion is a polyhedrin targeting peptide which is derived from cypovirus polyhedrin and binds to cypovirus polyhedrin. Microcubes comprising the C-terminal polyhedrin targeting peptide are referred to as PH-microcubes.

In one embodiment, the polyhedrin targeting peptide is a C-terminal portion of cypovirus polyhedrin. In one embodiment, the polyhedrin targeting peptide is a C-terminal portion of cypovirus polyhedrin absent all or part of the N-terminal H1 helix sequence.

In an illustrative embodiment, the polyhedrin targeting peptide is derived from silkworm (*Bombyx mori*) cypovirus (BmCPV) polyhedrin.

In another illustrative example, the polyhedrin targeting peptide comprises the peptide sequence as set forth in SEQ ID NO: 14 (PH-30), SEQ ID NO:13 (PH-24) or SEQ ID NO:12 (PH-14) or a functional variant of any one of these sequences.

The present invention is not limited by the type of protein of interest and the skilled person will recognize the broad application of the present invention. However, the present specification describes the successful production of modified polyhedra comprising membrane proteins of interest, such an antigens that are membrane proteins. Membrane proteins produced in polyhedral in accordance with the present specification are functional as determined by antibody binding. Accordingly, in one embodiment, the heterologous protein of interest is a membrane protein of interest or an antigen of a disease or condition. In some embodiments, the membrane protein of interest is an antigen of a disease or condition.

In another embodiment, the specification provides a complex comprising the fusion protein as described herein and cypovirus polyhedrin. During recombinant production of modified polyhedra, for example in insect cells, the C-terminal polyhedrin targeting peptide was determined to direct the protein of interest, including full length membrane proteins of interest (which may comprise one or more membrane spanning portions) to which it is fused to the same cytoplasmic compartment comprising polyhedrin and there to form polyhedra. The C-terminal polyhedrin targeting peptides described herein and routine derivatives or variants thereof were designed to function at the C-terminus of a target protein of interest. By functional is meant that the targeting peptide is capable of packaging the protein of interest or facilitating trimer formation and hence the ability to package the target protein of interest, even a membrane protein to form microcubes. This was unexpected in light of the prior art use of the N-terminal H1 portion of polyhedrin as a tag.

Accordingly, the specification provides polyhedra that comprise the fusion protein containing the polypeptide of interest (target protein).

Thus, in one embodiment the specification provides a modified crystalline polyhedron (microcube) comprising a complex between cypovirus derived polyhedrin polypeptide and a fusion protein comprising an N-terminal portion and a C-terminal portion, wherein the N-terminal portion is a heterologous protein of interest and the C-terminal portion is a polyhedrin targeting peptide which is derived from cypovirus polyhedrin and binds to cypovirus polyhedrin.

Thus, in one embodiment the specification provides a polyhedron (or the plural form, polyhedra) comprising a complex between polyhedrin and a fusion protein comprising an N-terminal portion and a C-terminal portion, wherein the N-terminal portion is a heterologous protein of interest and the C-terminal portion is a polyhedrin targeting peptide which is derived from cypovirus polyhedrin and binds to cypovirus polyhedrin.

In one embodiment, the specification enables a polyhedron comprising a complex between polyhedrin and a fusion protein comprising an N-terminal portion and a C-terminal portion, wherein the N-terminal portion is a heterologous membrane or surface antigen of a pathogen or condition and the C-terminal portion is a polyhedrin targeting peptide which is a polyhedrin absent all or part of the N-terminal H1 helix sequence (see FIG. 4A), Surprisingly, the C-terminal portion is able to fold independently and adopt a trimeric structure that will stabilize a trimeric assembly including the protein of interest attached to the tag. The ability of antigen specific conformational antibodies to bind to the surface of recombinant polyhedra shows that the protein is also present on the surface of the microcube and is folded correctly (See for example, FIGS. 7 and 30).

In one embodiment, the polyhedrin targeting peptide is derived from a C-terminal portion of H1 (polyhedrin—reference herein to "H1" as the source of the polyhedrin targeting peptide of the present invention is incorrect and should be "polyhedrin"—the prior art tag was H1) of CPV. Reference to a C-terminal portion of polyhedrin of CPV includes functional variants of peptides having the sequences set forth in SEQ ID NOs 14, 13 and 12. C-terminal portions of CPV polyhedrin comprise, in some embodiments, at least 219 amino acids e.g., residues 30 to 249 (PH-30) or 214 amino acids e.g., residues 24 to 249 (PH-24), or 235 amino acids e.g., residues 14 to 249 (PH-14) of polyhedrin of CPV or their equivalents representing, for example, 87%, 85%, 90% or 94% of the full length sequence. In some embodiments, the C-terminal portion is absent N-terminal sequences representing at least 1%, 2%, 3%, 4%, 5%, 6%, 7%, 8%, 9%, 10%, 11%, 12% or 13-20% of the full length polyhedrin CPV sequence. Functional variants may be produced and tested using the methods described herein and as known in the art. They may be tested for their ability to guide proteins of interest into microcubes. Functional variants include modified functional forms comprising one or more, but generally no more than 5 to 10 substituted amino acids as known in the art and further described herein. Targeting peptides PH14, PH24 and PH30 are provided.

The ability of recombinant polyhedra presenting membrane proteins such as HIV GAG, ENV, influenza hemagglutinin, TB, malaria GPs, viral capsid proteins such as hepatitis viral proteins. Such proteins would previously have been expressed and matured in the secretory pathways of a host cell. In accordance with the present invention such proteins are co-located with polyhedrin in the cytoplasm.

In one embodiment, the present specification provides a composition or kit comprising the herein described fusion protein or complex or polyhedron/polyhedra.

Thus in one embodiment the specification provides a composition comprising a complex between polyhedrin and a fusion protein comprising an N-terminal portion and a C-terminal portion, wherein the N-terminal portion is a heterologous protein of interest and the C-terminal portion is a peptide comprising the sequence set for the in SEQ ID NO: 14 or a functional variant thereof.

In one embodiment, the composition comprises a physiologically or pharmaceutically acceptable carrier and/or diluent.

The present specification further provides for the use of the herein disclosed compositions in, or in the manufacture of a preparation for, the treatment or prevention of a condition associated with the heterologous protein of interest. For example, many antigens able to elicit neutralizing antibodies are surface or membrane proteins which may be produced in the modified polydedra described herein and formulated as compositions for administration to a subject in need. The specification further provides for their use in, or in the manufacture of a diagnostic agent for, the diagnosis or monitoring of a condition associated with the heterologous protein of interest.

The compositions, may be used in accordance with one embodiment, in:

(i) a method for eliciting an immune response in a subject, the method comprising administering to the subject or patient an effective amount of the composition and under conditions to elicit an immune response;

(ii) a method for immunising a subject against infection or disease or a condition associated with the protein of interest comprising administering the composition to the subject;

(iii) a method for treating or preventing infection by a pathogen or a cancer or other condition comprising administering the composition to the subject for a time and under conditions sufficient to treat or prevent the infection or cancer or disease or condition; or (iv) a method for producing an isolated or purified antibody or immune cell that specifically binds to a heterologous protein of interest, including a membrane protein of interest or an antigen of a disease or condition or other antigen against which an immune response is sought in a human or non-human animal subject, comprising administering to a subject an effective amount of the composition, and isolating or purifying the antibody or immune cell.

In another expression, the specification provides a nucleic acid molecule encoding and capable of expressing a fusion protein comprising an N-terminal portion and a C-terminal portion, wherein the N-terminal portion is a heterologous protein of interest and the C-terminal portion is a polyhedrin targeting peptide which is derived from cypovirus polyhedrin and binds to cypovirus polyhedrin, or a vector encoding and capable of directing expression of the C-terminal portion of a polyhedrin targeting peptide which is derived from cypovirus polyhedrin and binds to cypovirus polyhedrin and comprising sites for introduction of an N-terminal heterologous protein of interest. Alternative signal sequences are known in the art. In one embodiment the melittin signal sequence is employed.

The present specification contemplates a host cell comprising the fusion protein or the complex or polyhedra comprising same or the nucleic acid molecule able to express the fusion protein or the C-terminal targeting peptides and any inserted protein of interest, wherein the fusion protein comprises an N-terminal portion and a C-terminal portion, and wherein the N-terminal portion is a heterologous protein of interest and the C-terminal portion is a polyhedrin targeting peptide which is derived from cypovirus polyhedrin and binds to cypovirus polyhedrin. In one embodiment, the polyhedrin targeting peptide is a C-terminal portion of cypovirus polyhedrin. In another embodiment, the polyhedrin targeting peptide is a C-terminal portion of cypovirus polyhedrin absent all or part of the N-terminal H1 helix sequence. In an illustrative embodiment, the polyhedrin targeting peptide is derived from silkworm (Bombyx mori) cypovirus (BmCPV) polyhedrin. In another illustrative example, the polyhedrin targeting peptide comprises the peptide sequence as set forth in SEQ ID NO: 14 (PH30), SEQ ID NO:13 (PH24) or SEQ ID NO:12 (PH14) or a functional variant of any one of these sequences.

The present invention is not limited by the type of protein of interest and the skilled person will recognize the broad application of the present invention. However, the present specification describes the successful production of modified polyhedra comprising membrane proteins of interest, such an antigens that are membrane proteins. Accordingly, in one embodiment, the heterologous protein of interest is a membrane protein of interest or an antigen of a disease or condition. In some embodiments, the membrane protein of interest is an antigen of a disease or condition.

Screening methods are also provided based on the presentation of a protein of interest in the context of a modified polyhedra or complexes between the subject fusion proteins and polyhedrin. Illustrative method include screening for putative interacting agents comprising contacting a complex fusion protein as described herein with a putative interacting agent and determining binding relative to controls.

The above summary is not and should not be seen in any way as an exhaustive recitation of all embodiments of the present description.

BRIEF DESCRIPTION OF THE FIGURES

FIGS. 14-19 further describe the sequences used to generate the pMel-PH vectors and pFastBac-PH-Env vectors described in the specification, and illustrate the tags, PH30, 14, and 24.

Figure 1:
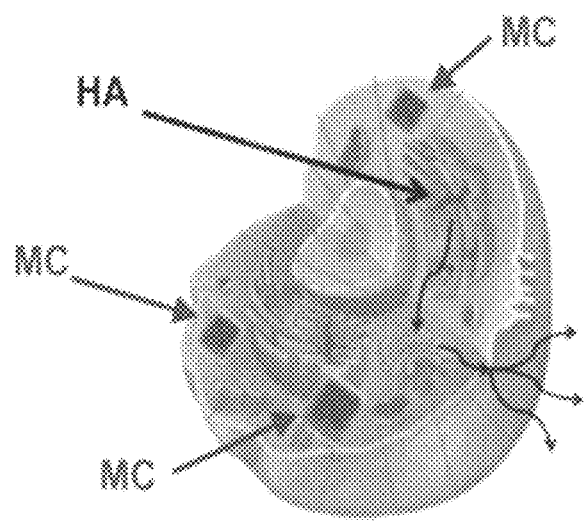
FIG. 1. Glycoproteins and MicroCubes (MC) form in different compartments.

The present description enables the use of modified elements of insect virus crystals, referred to as polyhedra, to stably present or provide functional proteins for a wide range of applications.

In one broad embodiment, the present description provides a fusion protein comprising a C-terminal polyhedrin targeting peptide (tag) of cytoplasmic polyhedrosis virus (CPV or cypovirus) poyhedrin, and an N-terminal heterologous protein of interest.

The heterologous protein of interest may be any protein of interest in the field. In one illustrative example, which illustrates one of the advantages of the present innovation, the protein is a membrane protein.

In one embodiment, a membrane protein, is any protein found in nature in a biological membrane or parts or variants thereof as known in the art. Membrane proteins may be integral or peripheral to the membrane. Integral proteins are commonly transmembrane proteins. Membrane proteins produced using the subject methods may be type I or type II transmembrane proteins. In one embodiment, Type I proteins are specifically contemplated. The subject membrane proteins may be receptors, channels, ligands, enzymes and antigens. The present invention enables production of full length membrane proteins constrained within polyhedra or a complex comprising polyhedra. In some embodiments, the membrane protein is an antigen of a pathogen.

Illustrative polyhedrin targeting peptides are C-terminal (polyhedron) polyhedrin fragments comprising amino acid sequences set out in SEQ ID NO: 14, 13 and 12 or functional variants thereof. The presently designed targeting peptides (tags) were designed to be functional when located at the C-terminus of the target protein (the protein to be packaged within microcubes. They represent regions of the BmCPV polyedrin or peptides derived thereform that retain the ability to be involved in trimer formation.

As used herein with reference to polyhedrin targeting peptides, functional variants retain the ability to guide the protein of interest as a fusion protein with the targeting peptide to form complexes comprising polyhedra (microcubes).

In a related embodiment, the description provides a stable complex comprising the fusion protein as described herein together with a polyhedrin protein of CPV. Thus, the fusion protein comprises comprising a C-terminal polyhedrin targeting peptide (tag) of cytoplasmic polyhedrosis virus (CPV) polyhedrin, and an N-terminal heterologous protein of interest.

In one embodiment, the heterologous protein of interest is a membrane protein of interest.

In one embodiment, the polyhedrin targeting peptide is a C-terminal fragment of polyhedrin CPV. Illustrative fragments lack the N-terminus of polyhedrin CPV, such as amino acids 1 to 35, 1 to 34, 1 to 33, 1 to 32 and so on down to about 1 to 12 of CPV polyhedrin.

Illustrative polyhedrin targeting peptides are C-terminal polyhedrin fragments comprising an amino acid sequence set out in one of SEQ ID NO: 14, 13 and 12 or functional variants thereof.

Illustrative polyhedrin targeting peptides are C-terminal polyhedrin fragments comprising amino acids sequences set out in SEQ ID NO: 14, 13 and 12 or functional variants thereof including amino acids having at least 80%, or at least 85%, 90%, 95%, 96%, 97%, 98% or 99% sequence identity as further described herein.

In one broad embodiment, the present description provides a fusion protein comprising a C-terminal polyhedrin targeting peptide of cytoplasmic polyhedrosos virus (CPV) polyhedrin or a functional variant thereof, and an N-terminal heterologous protein of interest.

The term "complex" refers to the "protein-polyhedrin subunit" which forms the modified polyhedra. In some embodiments, the term "complex" also refers to the modified polyhedra (the terms "MicroCubes", "polyhedra crystals", "modified polyhedra crystals", "polyhedra", "polyhedrin" or "micromolecular structure" and the like are used interchangeably) comprising the protein of interest. In one non-limiting embodiment, the protein of interest is antigen of a pathogen or disease or condition affecting a human or non-human mammalian subject.

In some embodiments, the present description employs protocols developed previously to express polypeptides as fusion proteins in insect polyhedra. This technology is known in the art and may be reviewed for example in Ikeda et al., J. Virol. 75: 988-995, 2001; Ikeda et al., Proteomics, 6: 54-66, 2006; Mori et al., J. Biol. Chem. 282(23): 17289-17296, 2007; Ijiri et al. Biomaterials 30: 4297-4308, 2009 incorporated herein in their entirely by reference. The present invention provides, in one embodiment polyhedrin-based targeting peptides which are enabled for guiding the protein of interest into polyhedra. In one embodiment, the polyhedrin targeting peptides are fused C-terminally to the protein of interest where they direct inclusion of the protein in polyhedron crystals.

"Polyhedrin" and "polyhedrin-like" encompasses any naturally occurring form of polyhedrin from any cytoplasmic polyhedrosis virus (cypovirus) (CPV) as well as their biologically active portions and variants, analogs, homologs or derivatives of these, as defined herein. Different polyhedrin polypeptide and peptide sequences are available in the art (see NCBI Entrez Search). A polyhedrin may be selected from the art and routinely tested in the methods described herein. Polyhedrin molecules produced by CPV are distinct from those produced by baculoviruses. They differ in structure and the viruses are unrelated. Differences are described between their molecular structures in Coulibaly et al., Proc. Natl. Acad. Sci. U.S.A. 106(52): 22205-22210, 2009—baculovirus polyhedra have an envelope that may prevent full access to antigens and their cellular localisation is distinct as CPVs replicate in the cytoplasm and baculoviruses in the nucleus.

In some embodiments, microcubes are in isolated, homogeneous, fully or partly purified form. Isolation and/or purification can be carried out by methods known in the art including salt fractionation, ion exchange chromatography, gel filtration, size-exclusion chromatography, size-fractionation, and affinity and immunoaffinity chromatography. FACS separation may also be employed.

The term "isolated" or "purified" means material that is substantially or essentially free from components that normally accompany it in its native state. For example, an "isolated complex", as used herein refers to a complex isolated from the cellular, cell-free, or molecular mixtures used in its production. In some embodiments, the purified complex is at least 95 to 99% pure.

The present specification provides for the use of a C-terminal CPV polyhedrin targeting peptide as described herein, in a fusion protein comprising an N-terminal heterologous protein of interest, to facilitate inclusion during expression of the heterologous protein of interest into modified CPV polyhedra within cells. Polyhedra are modified by inclusion of a heterologous protein of interest. They typically will not contain CPV virus particles.

In a related embodiment, plasmids and vectors able to express the subject modified targeting peptides and fusion proteins are expressly contemplated. Various illustrative vectors and constructs are described in the examples, figures and figure legends.

In one embodiment, the polyhedrin targeting peptide is derived from a C-terminal portion of H1 (polyhedrin) of CPV. Reference to a C-terminal portion of polyhedrin of CPV includes functional variants of peptides having the sequences set forth in SEQ ID NOs 14, 13 and 12. C-terminal portions of CPV polyhedrin comprise, in some embodiments, at least 219 amino acids e.g., residues 30 to 249 (PH-30) or 214 amino acids e.g., residues 24 to 249 (PH-24), or 235 amino acids e.g., residues 14 to 249 (PH-14) of polyhedrin of CPV or their equivalents representing, for example, 87%, 85%, 90% or 94% of the full length sequence. In some embodiments, the C-terminal portion is absent N-terminal sequences representing at least 1%, 2%, 3%, 4%, 5% or 6% of the full length polyhedrin CPV sequence. Functional variants may be produced and tested using the methods described herein and as known in the art. Tested for their ability to guide proteins of interest into microcubes. Functional variants include modified functional forms comprising one or more, but generally no more than 5 to 10 substituted amino acids as known in the art and further described herein. Targeting peptides PH14, PH24 and PH30 are provided.

Reference to "stable" includes that the heterologous (non-CPV) protein component of the complex in the polyhedron is substantially resistant to degradation under physiological or environmental conditions or exhibits decreased degradation compared to a control such as the antigen in the absence of the complex or polyhedra comprising same. Facets of "stability" include slow release applications.

In some embodiments, the heterologous protein in the polyhedra is heat stable. For example, as described in the Examples, MicroCube antigens are stable at between about 4° C. and about 21° C. and even at about 37° C. In some other embodiments, the heterologous protein of interest in the polyhedra displays decreased degradation relative to the unconstrained form.

In some embodiments, reference to "decreased degradation" refers to a composition displaying less than 50%, or less than 40%, less than 30%, less than 20%, less than 10%, less than 1% protein degradation over a storage period under conditions wherein the same antigen not present in a complex with polyhedrin or in a polyhedron exhibits more than 50%, 60%, 70% or more protein degradation. In some embodiments, the protein in the polyhedron is resistant to enzymatic such as trypsin degradation.

In an illustrative non-limiting embodiment, the polyhedrin is derived from *Bombyx mori* CPV. Functional variants may be naturally occurring or artificially produced.

By "derived from" is meant naturally occurring forms and functional variants of naturally occurring forms and therefore includes sequences directly or indirectly derived from an organism. For example, a viral polypeptide such as polyhedrin is "derived from" a particular polypeptide of a virus (viral polypeptide) if it is (i) encoded by an open reading frame of a polynucleotide of that virus (viral polynucleotide), or (ii) displays sequence and or structure-functional similarity to polypeptides of that virus as described herein. Functional variants are described herein and include derivatives which may be fragments of a polyhedrin polypeptide.

In one embodiment, the heterologous protein of interest is fused N-terminally to an CPV polyhedrin targeting peptide or a functional variant thereof.

In one embodiment, the heterologous membrane protein of interest is fused N-terminally to a CPV polyhedrin targeting peptide or a functional variant thereof.

As will be appreciated, in relation to the applications of recombinant polyhedra to function as antigens in vaccines against infections, diseases and conditions, many antigens involved in these events are surface or membrane proteins. This in one embodiment the heterologous protein of interest is a membrane protein, such as a membrane or surface protein or a pathogen or cancer antigen as described further herein or known in the art.

Correctly, in one embodiment, the heterologous protein of interest is fused N-terminally to a CPV polyhedrin targeting peptide or a functional variant thereof derived from a C-terminal portion of polyhedrin.

In one embodiment the C-terminal portion of polyhedrin is absent all or part of the N-terminal H1 alpha helix of polyhedrin. The H1 tag comprises residues 1 to 30 of Bombxy mori (Bm) cypovirus (BmCPV) or the corresponding region from functionally a related cypovirus. Thus in one embodiment the C-terminal portion of polyhedrin lacks 1-29 of the BmCPV polyhedrin H1. For example, the PH30 tag is about residues 30-248 of polyhedrin or about residues 20 to 249 of polyhedrin protein.

Reference to polyhedrin targeting peptide means the targeting peptide is derived from polyhedrin and targets associated proteins to polyhedrin during production of the polyhedra. Thus the associated protein or heterologous protein of interest is drawn into polyhedra through association as a fusion protein with the polyhedrin targeting peptide (polyhedrin recognition sequence). The C-terminal polyhedrin targeting peptide facilitates co-location of the heterologous protein of interest including a membrane protein of an antigen or other membrane protein of interest with polyhedrin expressed in the cytoplasm of cells such as insect cells. As determined herein, this co-location is sufficient to facilitate efficient packaging of the membrane protein into polyhedra.

In some embodiments, the heterologous protein of interest is fused N-terminally to a C-terminal fragment of CPV polyhedrin, or a functional variant thereof.

In some non-limiting embodiments, the targeting peptide is derived from *Bombyx mori*.

In an illustrative embodiment, a chimeric protein-polyhedrin targeting protein/peptide of the present description is produced wherein at least two polypeptides or peptides derived from different species are linked by covalent bonds, either by being expressed as part of the same expression product or by synthesis. In both cases the resulting polypeptide may be referred to as a fusion protein. Direct attachment of protein to polyhedra by covalent cross-linking or coating is also contemplated.

The terms "polypeptide" "protein" and "peptide" and "glycoprotein" and "antigen" are used interchangeably and mean a polymer of amino acids not limited to any particular length. The term does not exclude modifications such as myristylation, glycosylation, phosphorylation and addition and/or deletion of signal sequences.

In another embodiment, the description provides a method for producing a complex comprising (a) a fusion polypeptide comprising a protein of interest fused N-terminally to a polyhedrin targeting peptide as described and (b) polyhedrin, the method comprising expressing a nucleic acid molecule encoding the protein of interest as a fusion polypeptide with the polyhedrin targeting peptide and expressing a nucleic acid molecule encoding a polyhedrin or polyhedrin-like polypeptide in an insect or other suitable host cell and contacting the polyhedrin and fusion polypeptides for a time and under conditions sufficient for the fusion protein comprising the protein of interest and the polyhedrin to form a complex. In some embodiments, the two proteins are co-produced in an insect or other equivalent host cell. The complex typically comprises a plurality of copies of the fusion protein. In a particular embodiment, the method further comprises isolating or purifying the complex from other cellular or culture material.

In other embodiments fusion polypeptides may be directly synthesised and combined with polyhedrin in host cells or under cell free conditions that allow the formation of polyhedrin-protein of interest complexes and folding and production of polyhedra or polyhedra-like particles.

In some embodiments, the methods increase the half-life or shelf life (stability) of an protein of interest prepared according to the above method or a composition comprising same. In some embodiments, the methods increase the resistance of the preparation comprising the protein of interest to enzymatic degradation or degradation under certain physiological or environmental conditions.

In some embodiments, kits such as immunodiagnostic or immunoscreening kits comprising the isolated or purified complexes or fusion proteins and/or antibodies thereto are contemplated.

Modified CPV polyhedra are provided comprising a fusion protein comprising heterologous protein of interest and a C-terminal polyhedrin targeting peptide derived from H1 polyhedrin of CPV. Solid surfaces comprising same for diagnostic, screening and therapeutic applications are provided.

In some embodiments, antibodies are produced according to a method comprising administering to a non-human subject an effective amount of a complex comprising a) a fusion polypeptide comprising a protein of interest fused N-terminally to a CPV polyhedrin targeting peptide as described herein and (b) polyhedrin, wherein administration is for a time and under conditions sufficient for the protein to induce an antibody response. In other embodiments, the fusion protein, rather than the complex comprising same is administered. In some embodiments, antibodies are used in the manufacture of a chimeric, deimmunised, humanised or human antibodies as known in the art.

In another embodiment, the present description contemplates methods for screening putative interacting (binding) agents for those that bind to a subject protein in the form of a complex comprising polyhedrin or a fusion polypeptide as described herein. In some embodiments, the methods comprise contacting a purified complex or fusion protein of the present description with a putative interacting agent and determining binding relative to controls. In some embodiments, binding agents are further tested for their ability to reduce the level or activity of a pathogen or cancerous cell from which the antigen is derived.

Further embodiments are directed to a nucleic acid molecule encoding the fusion polypeptides described herein, vectors capable of directing expression, host cells comprising the subject complexes or fusion polypeptides, and compositions comprising purified recombinant or modified polyhedra. Compositions may include agents to facilitate destabilisation (such as pH modifiers) or stabilisation (such as cross-linking) of the complex in vivo.

Pharmaceutical compositions comprising the subject crystals or fusion proteins or an antibody determined thereby that specifically recognises the protein of interest are provided.

Functional variants include "derivatives" and include "biologically active portions" or "biologically active parts" or "functional part or portion" by which is meant a portion of a full-length targeting polypeptide (i.e., polyhedrin) which portion retains at least the activity of the full length molecule at least in so far as it retains the structural and functional abilities to target a protein to polyhedrin. As used herein, the term "biologically active portion" includes deletion mutants and peptides, for example of at least about 150-200 or 200 to 214 or 214 to 219, contiguous amino acids (and every integer in between), which retains activity. Portions of this type may be obtained through the application of standard recombinant nucleic acid techniques or synthesized using conventional or state of the art liquid or solid phase synthesis techniques. For example, reference may be made to solution synthesis or solid phase synthesis as described, for example, in Chapter 9. By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a targeting polypeptide including additions, or deletions that provide for functionally equivalent molecules.

A "part" or "portion" of a polynucleotide or protein is defined as having a minimal size of at least about 20 nucleotides or amino acids and may have a minimal size of at least about 100 nucleotides or amino acids. This definition includes all sizes in the range of 10-35 nucleotides or amino acids including 10, 11, 12, 13, 14, 15, 16, 17, 18, 19, 20, 21, 22, 23, 24, 25, 26, 27, 28, 29, 30, 31, 32, 33, 34 or 35 nucleotides or amino acids as well as greater than 100 nucleotides or amino acids including 300, 500, 600, 700, 1500 and 2000 nucleotides or amino acids or molecules having any number of nucleotides or amino acids within these values. The Env construct comprises over 2400 nucleotides.

Reference herein to "functional variants" of targeting polypeptides or peptides or polyhedrin polypeptides include naturally or non-naturally occurring functional variants, biologically active parts or portions, precursors, derivatives, analogs and recombinant or synthetic forms having a degree of sequence similarity or the omission of one or more biologically active parts or portions sufficient to retain the functional and structural ability of the sequences identified herein to form complexes with polyhedrin as described herein. Functional variants are described further in the detailed description.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present description, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.*, 25: 3389-3402, 1997. A detailed discussion of sequence analysis can be found in Unit 19.3 of Ausubel et al., *Current Protocols in Molecular Biology*, John Wiley & Sons Inc, Chapter 15, 1994-1998.

The term "recombinant" may be used herein to describe a nucleic acid molecule and means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

The description provides a method for producing an antibody comprising immunising a non-human animal or screening expression products of a library of human immunoglobulin genes with a fusion or complex protein or polyhedra as described herein, or a nucleic acid encoding same and isolating an antibody that binds specifically to the subject protein or to all or part of a pathogen or tissue comprising same.

In another embodiment, the description provides an antibody produced by the methods described herein using a subject protein or complex or a subject, human or humanised form thereof. The antibody is preferable monoclonal rather than polyclonal and is preferably subject, humanised, deimmunised or is a human antibody.

Reference to functional variants of the herein described tags includes those that are distinguished from a naturally-occurring form or from forms presented herein by the addition, deletion and/or substitution of at least one amino acid residue. Thus, variants include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present description are biologically active, that is, they continue to possess the desired biological activity of the parent protein (e.g., immunogenicity or ability to form complexes with polyhedrin or encapsulate at least partially the antigen of interest). Variants may result from, for example, genetic polymorphism or from human manipulation. Biologically active variants of a viral polypeptide will typically have at least 40%, 50%, 60%, 70%, generally at least 75%, 80%, 85%, preferably about 90% to 95% or more, and more preferably about 98% or more sequence similarity or identity with the amino acid sequence or the published amino acid sequence for the protein described herein as determined by sequence alignment programs described elsewhere herein using default parameters. In some embodiments, percentage identified refers to the full length polypeptide or to the parent molecule from which the variant is derived. A functional variant of a subject polypeptide may differ from that polypeptide generally by as much 100, 50 or 20 amino acid residues or suitably by as few as 1-15 amino acid residues, as few as 1-10, such as 6-10, as few as 5, as few as 4, 3, 2, or even 1 amino acid residue.

A variant polypeptide may be altered in various ways including amino acid substitutions, deletions, truncations, and insertions. Methods for such manipulations are generally known in the art. For example, amino acid sequence variants of a subject polypeptide can be prepared by mutations in the DNA. Methods for mutagenesis and nucleotide sequence alterations are well known in the art. See, for example, Kunkel, *Proc. Natl. Acad. Sci. USA*, 82: 488-492, 1985; Kunkel et al., *Methods in Enzymol.*, 154: 367-382, 1987; U.S. Pat. No. 4,873,192; Watson et al., *Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., *Atlas of Protein Sequence and Structure*, Natl. Biomed. Res. Found., Washington, D.C., 1978. Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of subject polypeptides. Conservative substitutions, such as exchanging one amino acid with another having similar properties, are desirable as discussed in more detail below.

Variant subject polypeptides may contain conservative amino acid substitutions at various locations along their sequence, as compared to the reference amino acid sequence. A "conservative amino acid substitution" is one in which the amino acid residue is replaced with an amino acid residue having a similar side chain Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al. 1978, (supra), A model of evolutionary change in proteins. Matrices for determining distance relationships In M. O. Dayhoff, (ed.), Atlas of protein sequence and structure, Vol. 5, pp. 345-358, National Biomedical Research Foundation, Washington DC; and by Gonnet et al., *Science,* 256(5062): 1443-1445, 1992), however, include proline in the same group as glycine, serine, alanine and threonine. Accordingly, for the purposes of the present description, proline is classified as a "small" amino acid.

The degree of attraction or repulsion required for classification as polar or nonpolar is arbitrary and, therefore, amino acids specifically contemplated by the description have been classified as one or the other. Most amino acids not specifically named can be classified on the basis of known behavior.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not Small residues are, of course, always nonaromatic. Dependent on their structural properties, amino acid residues may fall in two or more classes. For the naturally-occurring protein amino acids, sub-classification according to this scheme is presented in the Table 1.

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional subject polypeptide can readily be determined by assaying its activity. Conservative substitutions are shown in Table 2 (below) under the heading of exemplary substitutions. More preferred substitutions are shown under the heading of preferred substitutions Amino acid substitutions falling within the scope of the description, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for functional activity Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry,* third edition, Wm.C. Brown Publishers (1993).

Thus, a predicted non-essential amino acid residue in a subject polypeptide is typically replaced with another amino acid residue from the same side chain family. Alternatively, mutations can be introduced randomly along all or part of a subject polynucleotide coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined.

Accordingly, the present description also contemplates variants of the subject polypeptides provided herein or their biologically-active fragments, wherein the variants are distinguished from the provided sequences by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity to a reference subject polypeptide sequence. Desirably, variants will have at least 30, 40, 50, 55, 60, 65, 70, 75, 80, 85, 90, 91, 92, 93, 94, 95, 96, 97, 98, 99% sequence identity to a parent subject polypeptide sequence. Moreover, sequences differing from the disclosed sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the biological activity of the parent subject polypeptide are contemplated. Variant subject polypeptides also include polypeptides that are encoded by polynucleotides that hybridize under stringency conditions as defined herein, especially high stringency conditions, to disclosed polynucleotide sequences, or the non-coding strand thereof.

In some embodiments, variant polypeptides differ from a prior art or wild-type sequence by at least one but by less than 50, 40, 30, 20, 15, 10, 8, 6, 5, 4, 3 or 2 amino acid residue(s). In another, variant polypeptides differ from the recited sequence by at least 1% but less than 20%, 15%, 10% or 5% of the residues. (If this comparison requires alignment the sequences should be aligned for maximum similarity. "Looped" out sequences from deletions or insertions, or mismatches, are considered differences.) The differences are, suitably, differences or changes at a non-essential residue or a conservative substitution.

A "non-essential" amino acid residue is a residue that can be altered from the wild-type sequence of an embodiment polypeptide without abolishing or substantially altering one or more of its activities. Suitably, the alteration does not substantially alter one of these activities, for example, the activity is at least 20%, 40%, 60%, 70% or 80% of wild-type. An "essential" amino acid residue is a residue that, when altered, results in abolition of an activity of the parent molecule such that less than 20% of the parent activity is present.

Reference herein to "bound" includes covalent and non-covalent bonds. In illustrated embodiments, the bond is a covalent bond, such as between linear components of a fusion protein. Another covalent bond is a disulphide base. "Fused" refers to a covalent bond.

"Synthetic" sequences, as used herein, include polynucleotides whose expression has been optimized as described herein, for example, by codon substitution, deletions, replacements and/or inactivation of inhibitory sequences usually in order to optimize expression. "Wild-type" or "native" or "naturally occurring" sequences, as used herein, refers to polypeptide encoding sequences that are essentially as they are found in nature.

Recombinant proteins/polypeptides and antigens can be conveniently prepared using standard protocols as described for example in Sambrook, et al., 1989 (supra), in particular Sections 16 and 17; Ausubel et al., 1994 (supra), in particular Chapters 10 and 16; and Coligan et al., Current Protocols in Protein Science, John Wiley & Sons, Inc. 1995-1997, in particular Chapters 1, 5 and 6. Fusion proteins comprising polyhedrin targeting peptides and expressing vectors encoding polyhedrin such as AcCP-H are described in Ikeda et al., 2006 (supra); US Publication No. 2006/0155114; Mori et al., 1993 (supra); International Publication No. WO 2008/1105672. The polypeptides or polynucleotides may be synthesized by chemical synthesis, e.g., using solution synthesis or solid phase synthesis as described, for example, in Chapter 9 of Atherton and Shephard (supra) and in Roberge et al., Science, 269(5221): 202-204, 1995.

The pharmaceutical compositions enabled herein include biologically active proteins of interest which are produced on or in polyhedra and are administered to a subject for therapy or prophylaxis. Many different kinds of biological molecules are contemplated for therapeutic applications which will benefit from administration in the form of modified polyhedra. Enhanced stability both inside and outside the body, half-life, controlled release and more uniform qualities are illustrative advantages. The following description encompasses vaccine-related embodiments and non-vaccine related applications.

Pharmaceutical compositions are conveniently prepared according to conventional pharmaceutical compounding techniques. See, for example, Remington's Pharmaceutical Sciences, 18th Ed., Mack Publishing, Company, Easton, Pa., U.S.A., 1990. The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. intravenous, oral or parenteral.

A "pharmaceutically acceptable carrier" and/or a diluent is a pharmaceutical vehicle comprised of a material that is not otherwise undesirable i.e., it is unlikely to cause a substantial adverse reaction by itself or with the active agent. Carriers may include all solvents, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes, For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. Tablet may contain a binder such as tragacanth, corn starch or gelatin; a disintegrating agent, such as alginic acid; and a lubricant, such as magnesium stearate. If desired, tablets may be sugar-coated or enteric-coated by standard techniques. The active agent can be encapsulated to make it stable to passage through the gastrointestinal tract. See for example, International Patent Publication No. WO 96/11698.

For parenteral administration, the composition may be dissolved in a carrier and administered as a solution or a suspension. When the agents are administered intrathecally, they may also be dissolved in cerebrospinal fluid. For transmucosal or transdermal (including patch) delivery, appropriate penetrants known in the art are used for delivering the subject complexes. For inhalation, delivery uses any convenient system such as dry powder aerosol, liquid delivery systems, air jet nebulizers, propellant systems. For example, the formulation can be administered in the form of an aerosol or mist. The agents may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's. In some embodiments the formulations may be incorporated in lipid monolayers or bilayers such as liposomes or micelles. Targeting therapies known in the art may be used to deliver the agents more specifically to certain types of cells or tissues such as, without limitation, antigen presenting cells.

The actual amount of active agent administered and the rate and time-course of administration will depend on the nature and severity of the disease or condition. Prescription of treatment, e.g. decisions on dosage, timing, etc. is within the responsibility of general practitioners or specialists and typically takes into account the condition of the individual patient, the site of delivery, the method of administration and other factors known to practitioners. Examples of techniques and protocols can be found in Remington's Pharmaceutical Sciences (supra).

In further describing the various applications of the subject compositions in eliciting immune responses, the compositions is generally administered in an effective amount and for a time an under conditions sufficient to elicit an immune response. The compositions of the present description may be administered as a single dose. Alternatively, the compositions may involve repeat doses or applications.

The terms "effective amount" including a "therapeutically effective amount" and "prophylactically effective amount" as used herein mean a sufficient amount a composition comprising a complex as defined herein, or a cell or antibody as described herein, which provides the desired therapeutic or physiological effect and is an amount sufficient to achieve a biological effect such as to induce enough humoral or cellular immunity. Desired biological effects include but are not limited to reduced or no symptoms, remission, reduced pathogen titres, reduced vascular or cerebral compromise, reduced nasal secretions, fever etc. Undesirable effects, e.g. side effects, may sometimes manifest along with the desired therapeutic effect; hence, a practitioner balances the potential benefits against the potential risks in determining an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. One of ordinary skill in the art would be able to determine the required amounts based on such factors as prior administration of agents, the subject's size, the severity of the subject's symptoms, pathogen load, and the particular composition or route of administration selected.

The terms "treatment" or "prophylaxis" or "therapy" are used interchangeably in their broadest context and include any measurable or statistically significant amelioration in at least some subjects in one or more symptoms of a condition to be treated or in the risk of developing a particular condition. Prophylaxis may be considered as reducing the severity or onset of a condition or signs of a condition. Treatment may also reduce the severity of existing conditions.

In some embodiments, a vaccine or composition of the present description is physiologically effective if its presence results in a detectable change in the physiology of a recipient patient that enhances or indicates an enhancement in at least one primary or secondary humoral or cellular immune response against at least one strain of an pathogen or virus. In some embodiments the vaccine composition is administered to protect against infection by a pathogen. The "protection" need not be absolute, i.e., the infection need not be totally prevented or eradicated, if there is a statistically significant improvement compared with a control population or set of patients. Protection may be limited to reducing the severity or rapidity of onset of symptoms of the viral or other pathogen infection, or the development of cancer or other condition as described herein.

In one embodiment, a vaccine composition of the present description is provided to a subject either before the onset of infection (so as to prevent or attenuate an anticipated infection) or after the initiation of an infection, and thereby protects against viral infection. In some embodiments, a vaccine composition of the present description is provided to a subject before or after onset of infection, to reduce viral transmission between subjects.

It will be further appreciated that compositions of the present description can be administered as the sole active pharmaceutical agent, or used in combination with one or more agents to treat or prevent pathogen infections or symptoms associated with such infection.

The pharmaceutical composition is contemplated to exhibit therapeutic activity when administered in an amount that depends upon the particular case. The variation depends, for example, on the human or animal and the agent chosen. A broad range of doses may be applicable. Considering a subject, for example, from about 0.1 µg to 1 µg (i.e., including 0.1 µg, 0.2 µg, 0.3 µg, 0.4 µg, 0.5 µg, 0.6 µg, 0.7 µg, 0.8 µg and 0.9 µg) 0.5 µg to 50 µg, 1 µg to 10 µg, 2 µg to 200 µg, 0.1 mg to 1.0 mg (i.e., including 0.1 mg, 0.2 mg, 0.3 mg, 0.4 mg, 0.5 mg, 0.6 mg, 0.7 mg, 0.8 mg and 0.9 mg), from about 15 mg to 35 mg, about 1 mg to 30 mg or from 5 to 50 mg, or from 10 mg to 100 mg of agent may be administered per kilogram of body weight per day or per every other day or per week or per month. Therapeutic including prophylactic compositions may be administered at a dosage of about 0.1 to 20 mg/kg however dosages above or below this amount are contemplated in the ranges set out above. A dose providing an effective amount will depend upon the age, weight and condition of a subject but typical dosages provide between about 1-500 µg/kg, such as about 50-200 µg or about 100 µg/kg subject weight. Dosage regimes may be adjusted to provide the optimum therapeutic response. For example, several divided doses may be administered daily, weekly, monthly or other suitable time intervals or the dose may be proportionally reduced as indicated by the exigencies of the situation. It is also possible to administer compositions in sustained release formulations. Pharmaceutical preparations are conveniently provided in unit dosage form such as tablets, capsules, powders etc.

The compositions, complexes, antibodies and cells may be administered in a convenient manner such as by the oral, intravenous, intraperitoneal, intramuscular, subcutaneous, intradermal, intrathecal or suppository routes or implanting (e.g. using slow release molecules). Administration may be systemic or local. References to systemic include intravenous, intraperitoneal, subcutaneous injection, infusion as well as administration via oral, rectal, vaginal and nasal routes or via inhalation. Other contemplated routes of administration are by patch, cellular transfer, implant, sublingually, intraocularly, topically or transdermally.

In some embodiments, oral or nasal administration is contemplated. Capillaries have a diameter or approximately 5 µm permitting administration of complexes that are smaller than about 1 µm diameter. Polyhedra of more than 5 µm may be administered subcutaneously or intra muscularly or by other convenient route known in the art. Polyhedra can routinely be separated based upon size.

Physiological solutions are known in the art and can be developed using routine protocls and knowledge.

In one illustrative embodiment, the protein of interest in the subject fusion protein and subject complex is an antigen and delivery of the complex to a subject in substantially particulate polyhedral form induces an immune response thereto. In accordance with the present description, the polyhedron reduces degradation of antigens. In some embodiments, it also activates the immune response and therefore potentially enhances the antigen-specific immune response.

In another embodiment, the present description provides a complex comprising (a) a fusion polypeptide comprising a polyhedrin targeting peptide and an antigen of a pathogen or other antigen associated with a condition against which an immune response is sought; and (b) polyhedrin. In some embodiments, the complex is immunogenic and/or provides sustained release in a subject. In other embodiments, the complex is suitable for eliciting an enhanced immune response compared to the immune response produced by the antigen not in the form of a complex with polyhedrin nor in the form of a fusion protein with a polyhedrin targeting peptide.

In some embodiments, the complex is in the form of a recombinant or modified polyhedron comprising a plurality of fusion polypeptides comprising an antigenic portion and a polyhedrin targeting portion. In some embodiments, the antigen portion comprises one or more epitopes derived from a single pathogenic organism or condition. In other embodiments, the antigen portion comprises one or more epitopes from more than one pathogen or condition. In some embodiments, the recombinant or modified polyhedra in the size range of 0.1 um to 50 um, more particularly, 0.1 um to 10 um, depending upon the insect polyhedrin molecules employed. Particle size may be tailored to the mode of administration for immunisation.

In an illustrative embodiment, the pathogen is HIV. In an illustrative embodiment, the membrane protein is HIV Env, or Influena HA In a further illustrative embodiment, the antigen is HIV Gag polypeptide or an antigenic peptide thereof. As known in the art a Gag is produced as a precursor comprising a myristylated protein (p55), which is typically processed to varying degrees by proteases to form matrix protein (MA-p17), core antigen capsid protein (CA-p24), nucleo-capsid protein (NC-p'7), p6, p2 and p1. HIV Gag p39 comprises p24, p9 and p6.

In some embodiments, the description provides pharmaceutical compositions including immunogenic or putative vaccine compositions comprising an isolated nucleic acid molecule encoding the subject fusion polypeptide.

In some embodiments, pharmaceutical compositions including an immunogenic or putative vaccine composition are formulated with a pharmaceutically acceptable carrier and/or diluent.

In other embodiments, the present description provides a pharmaceutical composition comprising a subject complex or fusion polypeptide as described herein.

A putative vaccine composition is one, for example, that shows promise of inducing an effective immune response in an accepted animal or cellular model.

In other embodiments, the description provides a method for producing an isolated or purified antibody or immune cell that specifically binds to an antigen of a pathogen As used herein, an "immune response" refers to the reaction of the body as a whole to the presence of a composition of the present description which includes making antibodies and developing immunity to the composition.

An "immunogenic composition" is a composition that comprises an antigenic molecule where administration of the composition to a subject results in the development in the subject of a humoral and/or a cellular immune response to the antigenic molecule of interest. In accordance with the present description, the polyhedrin protein or peptide is also immunogenic and stimulates an immune response suitable for enhancing the immune response to the antigen against which an immune response is sought.

Assays for assessing an immune response are described in the art and in the Examples and may comprise in vivo assays, such as assays to measure antibody responses and delayed type hypersensitivity responses. In an embodiment, the assay to measure antibody responses primarily may measure B-cell function as well as B-cell/T-cell interactions. Or they may comprise in vivo assays, trials etc.

In some embodiments, phenotypic cell assays can be performed to determine the frequency of certain cell types. Peripheral blood cell counts may be performed to determine the number of lymphocytes or macrophages in the blood. Antibodies can be used to screen peripheral blood lymphocytes to determine the percent of cells expressing a certain antigen as in the non-limiting example of determining CD4 cell counts and CD4/CD8 ratios.

Accordingly, the present description provides a composition comprising a complex as herein described wherein the immune response to the complex includes a cellular and a humoral response. In some embodiments, the immune response to the polyhedrin or polyhedrin peptide portion of the complex comprises a cellular or humoral response. In some embodiments, the immune response to the polyhedrin or polyhedrin peptide portion of the complex comprises inflammasome activation.

In some further embodiments, the subject compositions comprising porteins of interest such as antigens of interest further comprise a pharmaceutically or physiologically acceptable carrier and/or diluent.

The term "vaccine" as used herein refers to a pharmaceutical composition comprising an immunologically active component that induces an immunological response in a subject and possibly but not necessarily one or more additional components that enhance the immunological activity of said active component (for example an adjuvant). A vaccine may additionally comprise further components typical to pharmaceutical compositions. The immunologically active component of a vaccine according to the present description comprises an antigen of a pathogen or other antigen against which a immune response is sought in a human or non-human animal subject and a polyhedrin protein. The terms "vaccine" and "vaccine composition" are used interchangeably in the present description. As determined herein, the polyhedrin portion also induces an immune response.

"Subjects" contemplated in the present description include any animal of commercial or humanitarian interest including conveniently, primates, livestock animals including fish, crustacea, and birds, laboratory test animals, companion animals, or captive wild animals. In some embodiments the subject is a mammalian animal. In particular embodiments, the subject is a human subject. In some embodiments, "subjects" are humans or animals including laboratory or art accepted test or vehicle animals. "Patients" include human subjects in need of treatment or prophylaxis.

In another embodiment, the description provides an immunogenic composition comprising an antigen of a pathogen or other antigen against which an immune response is sought and a CPV polyhedron wherein delivery of the composition induces an immune response to the antigen and wherein the CPV polyhedron enhances the immune response to the antigen.

In some embodiments, the description provides an immunogenic composition comprising CPV polyhedra for use in conjunction with an antigen to stimulate an immune response to the antigen. In some embodiments, the CPV polyhedron is derived from Bombyx mori.

In another embodiment, the present description provides an immunogenic composition as described herein comprising a complex comprising an antigen of a pathogen or other antigen against which a immune response is sought in a human or non-human animal subject and a polyhedrin protein for use in the manufacture of a vaccine for the treatment or prevention of an infection, disease or condition associated with the antigen.

In another embodiment, there is provided for a use of an immunogenic composition as described herein comprising a complex comprising an antigen of a pathogen or other antigen against which a immune response is sought in a human or non-human animal subject and a polyhedrin protein in the manufacture of a medicament for the treatment or prevention of an infection, disease or condition associated with the antigen.

In another broad embodiment, there is provides a method for eliciting an immune response in a subject or patient, the method comprising administering to the subject or patient an effective amount of an immunogenic composition as described herein comprising a complex comprising an antigen of a pathogen or other antigen against which a immune response is sought in a human or non-human animal subject and a polyhedrin protein, under conditions to elicit an immune response.

Further, the description includes method for immunising a subject against infection or disease or condition associated with the antigen comprising administering to the subject an immunogenic composition as described herein comprising a complex comprising an antigen of a pathogen or other antigen against which a immune response is sought in a human or non-human animal subject and a polyhedrin protein.

Furthermore, the present description provides a method for treating or preventing infection by a pathogen or a disease (cancer) or other condition comprising administering to the subject an immunogenic composition as described herein comprising a complex comprising an antigen of a pathogen or other antigen against which a immune response is sought in a human or non-human animal subject and a polyhedrin protein, for a time and under conditions sufficient to treat or prevent the infection or cancer/disease or condition.

In one embodiment, the present description provides a method for inducing an immune response in a subject, the method comprising administering to the subject an effective amount of a complex comprising (a) an antigen of a pathogen or other antigen associated with a condition against which an immune response is sought; and (b) polyhedrin, wherein administration is for a time and under conditions sufficient for the antigen to induce an immune response.

In another embodiment, the present description provides a method for inducing an immune response in a subject, the method comprising administering to the subject an effective amount of a complex comprising (a) a chimeric fusion polypeptide comprising a polyhedrin targeting peptide and an antigen of a pathogen or other antigen associated with a condition against which an immune response is sought; and (b) polyhedrin, wherein administration is for a time and under conditions sufficient for the antigen to induce an immune response.

In one embodiment the chimeric fusion protein is a fusion protein comprising an N-terminal portion and a C-terminal portion, wherein the N-terminal portion is a heterologous protein of interest and the C-terminal portion is a polyhedrin targeting peptide which is derived from cypovirus polyhedrin and binds to cypovirus polyhedrin.

As described herein, in one embodiment, the polyhedrin targeting peptide is a C-terminal portion of cypovirus polyhedrin.

In one expression, the polyhedrin targeting peptide is a C-terminal portion of cypovirus polyhedrin absent all or part of the N-terminal H1 helix sequence.

As illustrated herein, in one embodiment the polyhedrin targeting peptide is derived from silkworm cypovirus (Bm-CPV) polyhedrin.

In some embodiments, the polyhedrin targeting peptide comprises the peptide sequence set forth in SEQ ID NO: 14 (PH30), SEQ ID NO:13 (PH24) or SEQ ID NO:12 (PH14) or a functional variant thereof.

As described herein, in some embodiments, the heterologous protein of interest is a membrane protein of interest or an antigen of a disease or condition.

In one embodiment the membrane protein of interest is an antigen of a disease or condition.

In some embodiments, the fusion protein is administered in the form of a complex comprising the fusion protein as described herein and cypovirus polyhedrin. In some embodiments, the fusion protein is administered in the form of a complex comprising the fusion protein as described herein and silkworm cypovirus (BmCPV) polyhedrin.

In a similar embodiment, the description provides a method for treatment or prophylaxis of a viral infection in a subject comprising administering a complex comprising a virus antigen and/or fusion protein comprising same according to the present description for a time and under conditions sufficient to treat or prevent the virus infection.

In a similar embodiment, the description provides a method for treatment or prophylaxis of an infection in a subject comprising administering a complex comprising a pathogen antigen or a tumor/cancer antigen and/or fusion protein comprising same according to the present description for a time and under conditions sufficient to treat or prevent the pathogen or tumor/cancer infection/condition.

In other similar embodiments, the description provides the subject complexes and fusion proteins for use in the treatment and/or prophylaxis of a viral infection or a pathogen or tumor/cancer infection/condition. In further similar embodiments, the complexes and/or fusion proteins are proposed for use in the manufacture of a medicament for treatment and/or prophylaxis of a viral pathogen or other pathogenic infection or tumor.

In some embodiments, the complex or polyhedra comprising same is in isolated, homogeneous, fully or partly purified form.

In some embodiments, the immune response to the complex includes an immune response to the polyhedrin portion of the complex and comprises a cellular or humoral immune response and/or comprises inflammasome activation. Activation may be detected by various assays such as by assaying for IL-1β secretion.

The above method encompasses the production of antibodies and/or immune cells in a non-human subject. In this embodiment, antibodies, for example, are suitable for use in the manufacture of therapeutic or prophylactic antibodies. In some other embodiments, such antibodies are useful for diagnosis, screening and research. In yet another embodiment, the methods encompass the induction of a humoral and/or immune response to the antigen in a subject susceptible to the pathogen or condition or in need of treatment or prophylaxis. In the case of prophylactic or therapeutic administration, mammalian including human subjects are particularly contemplated.

In an illustrative example, an antigen against which an immune response is sought is an antigen associated with a condition such as a tumor i.e., a tumor antigen. Accordingly, in some embodiments, the description employs one or more antigens that are described in the art as candidate antigens for vaccination purposes because, for example, they engender an effective immune response in an animal model, and re-package the antigen(s) as a complex with polyhedrin that forms micromolecular polyhedra wherein the antigen is structurally and physically constrained. Without being bound by any particular theory or mode of action, it is proposed that delivery of antigen in particulate polyhedral form will induce enhanced cellular and/or immune responses, preferably both. Alternatively, or in addition, slow or sustained release of antigen from the micromolecular structure is proposed to reduce the need for multiple administrations and/or generate higher titre/strength cellular or antibody responses.

In one embodiment the description provides a stable immunogenic or vaccine composition comprising a complex comprising an antigen of a pathogen or other antigen against which a immune response is sought in a human or non-human animal subject and a polyhedrin protein derived from a cytoplasmic polyhedrosis virus (CPV) wherein delivery of the complex to a subject in substantially particulate polyhedral form induces an immune response thereto.

Reference herein to a virus or viral antigen includes without limitation a virus or antigen therefrom from any virus family. Non-limiting examples of viral families include Adenoviridae, African swine fever-like viruses, Arenaviridae, Arterivirus, Astroviridae, Baculoviridae, Birnaviridae, Bunyaviridae, Caliciviridae, Circoviridae, Coronaviridae, Deltavirus, Filoviridae, Flaviviridae, Hepadnaviridae, Hepeviridae, Herpesviridae, Orthomyxoviridae, Paramyxoviridae, Picornaviridae, Poxyviridae, Reoviridae, Retroviridae and Rhabdoviridae. Particular viruses are from Paramyxoviridae, Retroviridae and Filoviridae.

In some embodiments, a virus includes a virus selected from influenza virus, respiratory syncytial virus (RSV), chlamydia, adenovirdiae, mastadenovirus, aviadenovirus, herpesviridae, herpes simplex virus 1, herpes simplex virus 2, herpes simplex virus 5, herpes simplex virus 6, leviviridae, levivirus, enterobacteria phase MS2, allolevirus, poxviridae, chordopoxvirinae, parapoxvirus, avipoxvirus, capripoxvirus, leporiipoxvirus, suipoxvirus, molluscipoxvirus, entomopoxvirinae, papovaviridae, polyomavirus, papillomavirus, paramyxoviridae, paramyxovirus, parainfluenza virus 1, mobillivirus, measles virus, rubulavirus, mumps virus, pneumonovirinae, pneumovirus, metapneumovirus, avian pneumovirus, human metapneumovirus, picornaviridae, enterovirus, rhinovirus, hepatovirus, human hepatitis A virus, cardiovirus, andapthovirus, reoviridae, orthoreovirus, orbivirus, rotavirus, cypovirus, fijivirus, phytoreovirus, oryzavirus, retroviridae, mammalian type B retroviruses, mammalian type C retroviruses, avian type C retroviruses, type D retrovirus group, BLV-HTLV retroviruses, lentivirus, human immunodeficiency virus 1, human immunodeficiency virus 2, spumavirus, flaviviridae, hepatitis C virus, hepadnaviridae, hepatitis B virus, togaviridae, alphavirus sindbis virus, rubivirus, rubella virus, rhabdoviridae, vesiculovirus, lyssavirus, ephemerovirus, cytorhabdovirus, necleorhabdovirus, arenaviridae, arenavirus, lymphocytic choriomeningitis virus, Ippy virus, lassa virus, coronaviridae, coronavirus and torovirus.

Illustrative viral pathogens include HIV, HSV, chlamydia, SARS, RSV, Dengue virus and Influenza. Another illustrative pathogen is an apicomplexal parasite such as *Plasmodium* Spp. The antigen or a pathogen or condition may be combined with a polyhedrin targeting polypeptide in accordance with various aspects of the present description.

In particular embodiments, the antigen is a polypeptide or peptide proposed to engender or facilitate the production of an effective immune response in at least some subjects. Without being bound by any particular theory or mode of action, it is proposed that the present complexes stabilise and or protect the three dimensional structure of the antigen and provide improved vehicles for effective immune response production, for antibody and in some embodiments neutralising antibody production and for immune response and antibody screening. In preparing antibodies for diagnosis or screening, an effective immune response is generally one that producing antibodies of sufficient affinity to be useful reagents in standard protocols employing antibodies, such as ELISA, RIA, RAPID, etc. In some embodiments, the antigen is recognised in the art as useful or potentially useful for generating a protective or neutralising immune response. A range of illustrative known target antigens are described herein. In other embodiments, the description permits the characterisation of new useful antigens and conformational epitopes recognised, for example, by neutralising antibodies from infected subjects.

Any viral or non-viral antigen of a pathogen or cancer may be engineered using the methods described or referenced in this specification.

An "antigen" or "immunogen" or "antigenic" or "immunogenic" refers to a molecule containing one or more epitopes (either linear, conformational or both) that will stimulate an immune system to make a humoral and/or cellular antigen-specific response.

Illustrative antigens include those selected from influenza virus haemagglutinin, human respiratory syncytial virus G glycoprotein, core protein, matrix protein or other protein of Dengue virus, measles virus haemagglutinin, herpes simplex virus type 2 glycoprotein gB, poliovirus I VP1, envelope or capsid glycoproteins of HIV-I or HIV-II, hepatitis B surface antigen, diptheria toxin, streptococcus 24M epitope, gonococcal pilin, pseudorabies virus g50 (gpD), pseudorabies virus II (gpB), pseudorabies virusglll (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulinahydodysenteriae protective antigen, bovine viral diarrhea glycoprotein 55, newcastle disease virus hemagglutinin-neuraminidase, swine flu hemagglutinin, swine flu neuraminidase, foot and mouth disease virus, hog colera virus, swine influenza virus, African swine fever virus, mycoplasma liyopneutiioniae, infectious bovine rhinotracheitis virus, infectious bovine rhinotracheitis virus glycoprotein E, glycoprotein G, infectious laryngotracheitis virus, infectious laryngotracheitis virus glycoprotein G or glycoprotein I, a glycoprotein of La Crosse virus, neonatal calf diarrhoea virus, Venezuelan equine encephalomyelitis virus, punta toro virus, murine leukemia virus, mouse mammary tumor virus, hepatitis B virus core protein and hepatitis B virus surface antigen or a fragment or derivative thereof, antigen of equine influenza virus or equine herpes virus, including equine influenza virus type A/Alaska 91 neuraminidase, equine influenza virus typeA/Miami 63 neuraminidase, equine influenza virus type A/Kentucky 81 neuraminidase equine herpes virus type 1 glycoprotein B, and equine herpes virus type 1 glycoprotein D, antigen of bovine respiratory syncytial virus or bovine parainfluenza virus, bovine respiratory syncytial virus attachment protein (BRSV G), bovine respiratory syncytial virus fusion protein (BRSV F), bovine respiratory syncytial virus nucleocapsid protein (BRSVN), bovine parainfluenza virus type 3 fusion protein, bovine parainfluenza virus type 3 hemagglutinin neuraminidase, bovine viral diarrhoea virus glycoprotein 48 and glycoprotein 53.

Illustrative cancer antigens include KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens, CEA, TAG-72, LEA, Burkitt's lymphoma antigen-38.13, CD19, human B-lymphoma antigen-CD20, CD33, melanoma specific antigens, ganglioside GD2, ganglioside GD3, ganglioside GM2, ganglioside GM3, tumor-specific transplantation type of cell-surface antigen (TSTA), virally-induced tumor antigens, T-antigen DNA tumor viruses, envelope antigens of RNA tumor viruses, oncofetal antigen-alpha-fetoprotein, CEA of colon, bladder tumor oncofetal antigen, differentiation antigen, human lung carcinoma antigen L6, L20, antigens of fibrosarcoma, human leukemia T cell antigen-Gp37, neoglycoprotein, sphingolipids, breast cancer antigen, EGFR (Epidermal growth factor receptor), HER2 antigen, polymorphic epithelial mucin, malignant human lymphocyte antigen-APO-1, differentiation antigen, including I antigen found in fetal erythrocytes, primary endoderm, I antigen found in adult erythrocytes, preimplantation embryos, I (Ma) found in gastric adenocarcinomas, M18, M39 found in breast epithelium, SSEA-1 found in myeloid cells, VEP8, VEP9, Myl, VIM-D5, Du56-22 found in colorectal cancer, TRA-1-85 (blood group H), C14 found in colonic adenocarcinoma, F3 found in lung adenocarcinoma, AH6 found in gastric cancer, Y hapten, LeY found in embryonal carcinoma cells, TL5 (blood group A), EGF receptor found in A431 cells, E1 series (blood group B) found in pancreatic cancer, FC10. 2 found in embryonal carcinoma cells, gastric adenocarcinoma antigen, CO-514 (blood group Lea) found in Adenocarcinoma, NS-10 found in adenocarcinomas, CO-43 (blood groupLeb), G49 found in EGF receptor of A431 cells, MH2 (blood groupALeb/Ley) found in colonic adenocarcinoma, 19.9 found in colon cancer, gastric cancer mucins, TsA7 found in myeloid cells, R24 found in melanoma, 4.2, GD3, D1.1, OFA-1, GM2, OFA-2, GD2, and M1:22:25:8 found in embryonal carcinoma cells, and SSEA-3 and SSEA-4 found in 4 to 8-cell stage embryos.

Non-viral pathogens and antigens further include those from pathogenic or non-pathogenic fungi, including parasites, including apicomplexa, or uni cellular parasites, nematodes, trematodes, cestodes and plant pathogen or parasitic bacteria.

In an illustrative embodiment, one important group of pathogens is the primary systemic fungal pathogens of man such *Coccidioides immitis, Histoplasma capsulatum, Blastomyces dermatitidis*, and *Paracoccidioides brasiliensis*. Important opportunistic fungal pathogens which tend to rely upon an immunocompromised host include *Cryptococcus neoformans, Pneumocystis jiroveci, Candida* spp., *Aspergillus* spp., *Penicillium marneffei*, and Zygomycetes, *Trichosporon beigelii*, and *Fusarium* spp. A range of pathogenic fungi are associated with immunocompromised subjects including those with AIDS, with chemotherapy induced neutropenia or patients undergoing haematopoietic stem cell transplantation, among others.

In some embodiments, the pathogen is a microbe including a bacterium, fungus, virus, algae, parasite, (including ecto- or endo-parasites) prion, oomycetes, slime, moulds, nematode, mycoplasma and the like. By way of non-limiting example, the microbe is selected from one or more of the following orders, genera or species: *Acinetobacter, Actinobacillus, Actinomycetes, Actinomyces, Aeromonas, Bacillus, Bacteroides, Bordetella, Borrelia, Brucella, Burkholderia, Campylobacter, Citrobacter, Clostridium, Corynebacterium, Enterobacter, Enterococcus, Erysipelothrix, Escherichia, Francisella, Haemophilus, Helicobacter, Klebsiella, Legionella, Leptospira, Listeria, Micrococcus, Moraxella, Morganella, Mycobacterium* (tuberculosis), *Nocardia, Neisseria, Pasteurella, Plesiomonas, Propionibacterium, Proteus, Providencia, Pseudomonas, Rhodococcus, Salmonella, Serratia, Shigella, Staphylococcus, Stenotrophomonas, Streptococcus, Treponema, Vibrio* (cholera) and *Yersinia* (plague), Adenoviridae, African swine fever-like viruses, Arenaviridae (such as viral haemorrhagic fevers, Lassa fever), Astroviridae (astroviruses) Bunyaviridae (La Crosse), Calicivirid (Norovirus), Coronaviridae (Corona virus), Filoviridae (such as Ebola virus, Marburg virus), Parvoviridae (B19 virus), Flaviviridae (such as hepatitis C virus, Dengue viruses), Hepadnaviridae (such as hepatitis B virus, Deltavirus), Herpesviridae (herpes simplex virus, varicella zoster virus), Orthomyxoviridae (influenza virus) Papovaviridae (papilloma virus) Paramyxoviridae (such as human parainfluenza viruses, mumps virus, measles virus, human respiratory syncytial virus) Picornaviridae (common cold virus), Poxviridae (small pox virus, orf virus, monkey poxvirus) Reoviridae (rotavirus) Retroviridae (human immunodeficiency virus) Paroviridae (paroviruses) Papillomaviridae, (papillomaviruses) alphaviruses and Rhabdoviridae (rabies virus), *Trypanosoma, Leishmania, Giardia, Trichomonas, Entamoeba, Naegleria, Acanthamoeba, Plasmodium, Toxoplasma, Cryptosporidium, Isospora, Balantidium, Schistosoma, Echinostoma, Fasciolopsis, Clonorchis, Fasciola, Opisthorchis* and *Paragonimus*, Pseudophyllidea (e.g., *Diphyllobothrium*) and *Cyclophyllidea* (e.g., *Taenia*). Pathogenic nematodes include species from the orders; *Rhabditida* (e.g., *Strongyloides*), *Strongylida*

(e.g., *Ancylostoma*), *Ascarida* (e.g., *Ascaris*, *Toxocara*), *Spirurida* (e.g., *Dracunculus*, *Brugia*, *Onchocerca*, *Wucheria*), and *Adenophorea* (e.g., *Trichuris* and *Trichinella*), *Prototheca* and *Ptiesteria*, *Absidia*, *Aspergillus*, *Blastomyces*, *Candida* (yeast), *Cladophialophera*, *Coccidioides*, *Cryptococcus*, *Cunninghamella*, *Fusarium*, *Histoplasma*, *Madurella*, *Malassezia*, *Microsporum*, *Mucor*, *Paecilomyces*, *Paracoccidioides*, *Penicillium*, *Pneumocystis*, *Pseudallescheria*, *Rhizopus*, *Rhodotorula*, *Scedosporium*, *Sporothrix*, *Trichophyton* and *Trichosporon*. For the avoidance of doubt the pathogen may include an emerging or re-emerging pathogen or an organism which has never previously been identified as a pathogen in a particular subject.

The present invention is further described by the following non-limiting Examples, together with the Sequence listing, Figures and Figure legends.

Example 1

PH Tags: a Novel Technology to Incorporate Membrane Proteins into Microcrystals for Biotechnological Applications MicroCubes were developed from protein crystals called polyhedra produced by common insect viruses. In nature, these crystals function to protect the virus particles from environmental insults. MicroCubes were engineered as a vaccine platform where antigens of interest are incorporated in place of the virus particles exploiting their natural robustness and packaging abily. Importantly, the remarkable capacity of MicroCubes to accommodate cargoes of different sizes and natures is unique and vastly superior to that of virus-like particles (VLPs). In previous studies (see WO 2008/105672 incorporated herein), polyhedra-based mixed crystals containing cargoes of interest have been produced using a VP3 tag and the H1 tag. The VP3 tag introduces another protein sequence (the viral VP3 protein) and has been overall less efficient than the H1 tag. The H1 tag has been successfully used for applications in the field of stem cells and tissue repair. Polyhedra crystals containing antigens fused to H1 represent a viable vaccine platform that is referred to as H1-MicroCube (see WO 2011/160177). As a proof of concept, H1-MicroCubes were produced expressing the full-length Gag protein of HIV with the H1-tag as an N-terminal extension. Murine immunisation studies showed no toxic effect of H1-MicroCubes and demonstrated that HIV Gag H1-MicroCubes induce robust Gag-specific humoral and cellular responses in the absence of adjuvant. These studies indicated that the crystalline nature of H1-MicroCubes triggers danger signals that induce innate immune responses through the NLRP3 inflammasome, in a mechanism similar to the broadly used adjuvant Alum.

However a major limitation of the H1-MicroCube platform has been the impossibility to include surface proteins. This results from an intrinsic limitation of the H1 technology that functions only as an N-terminal fusion protein and the fact that these target proteins are inserted in a membrane with the largest domain translocated in a compartment physically separated from H1-MicroCubes. Here the engineering of PH-MicroCubes is described, a novel technology that allows the incorporation of full-length membrane proteins in their antigenically-native and functional state.

Figure 7A:
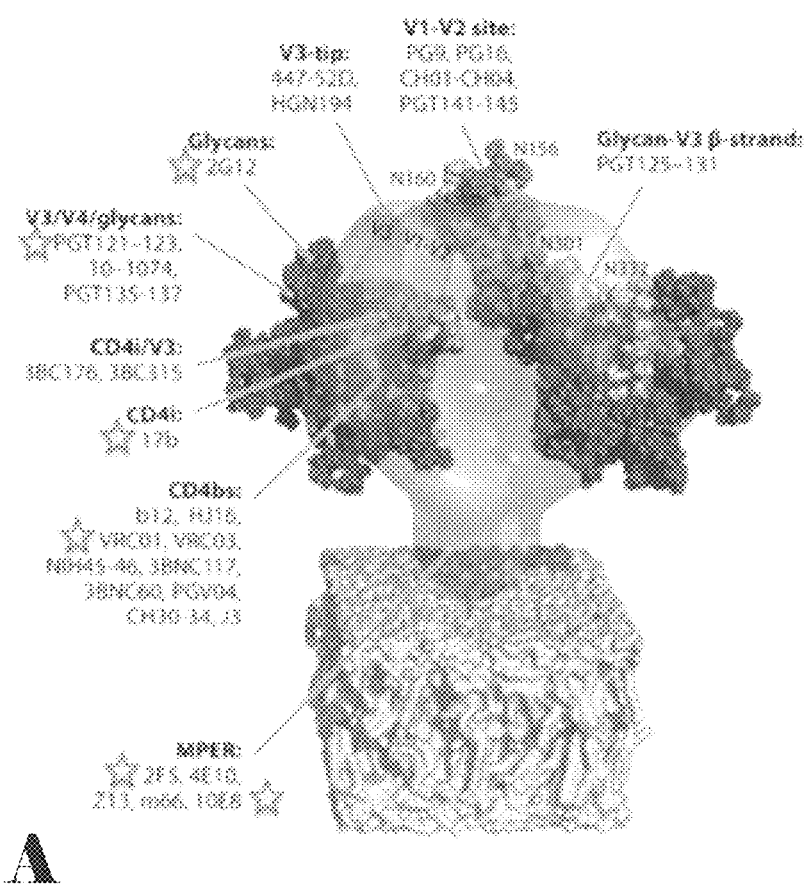
FIG. 7. Env PH-MicroCubes present a form of Env that is antigenically native, recognised by HIV-positive sera and functional.
Figure 7B:
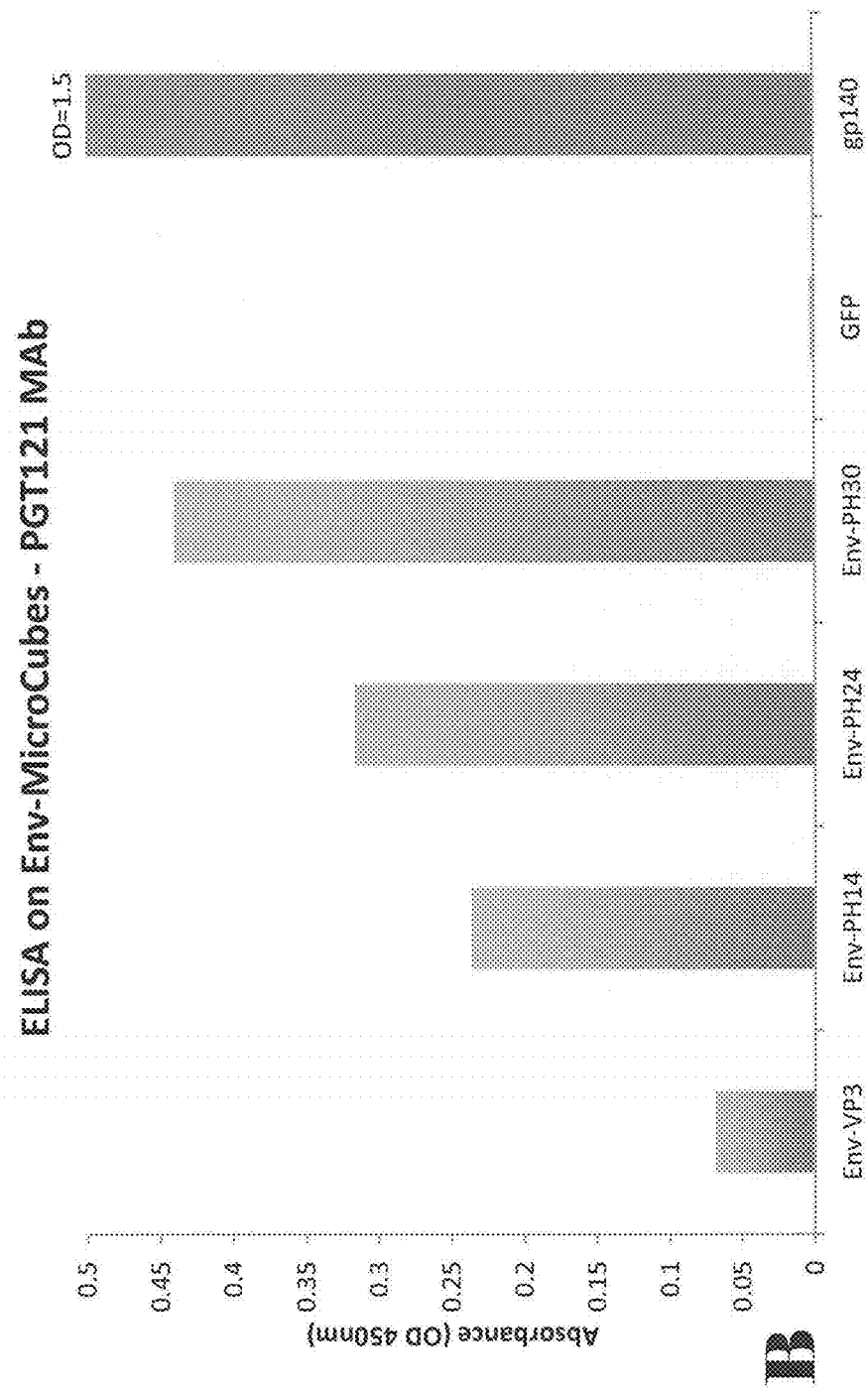
Figure 7B:
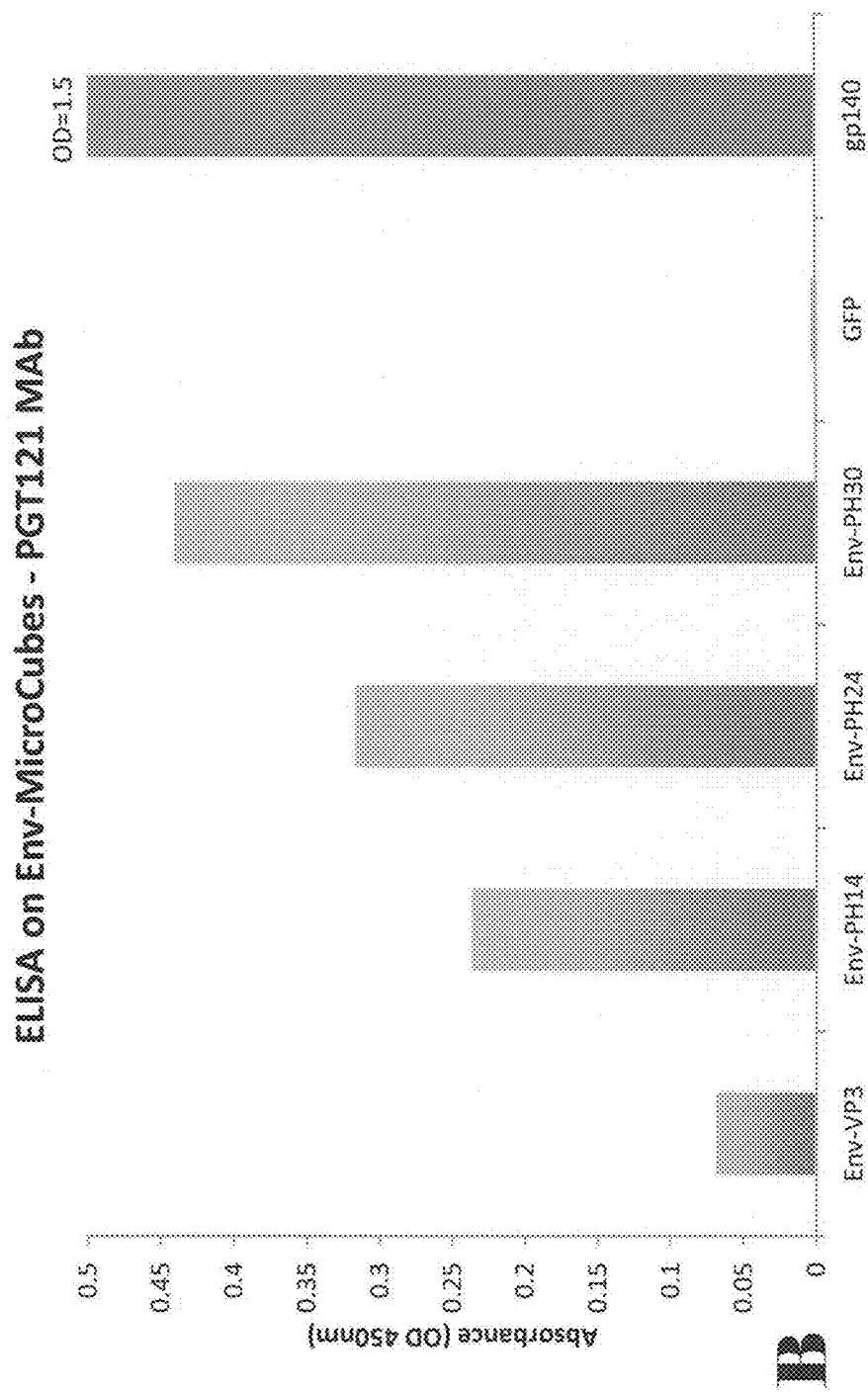
Figure 7B:
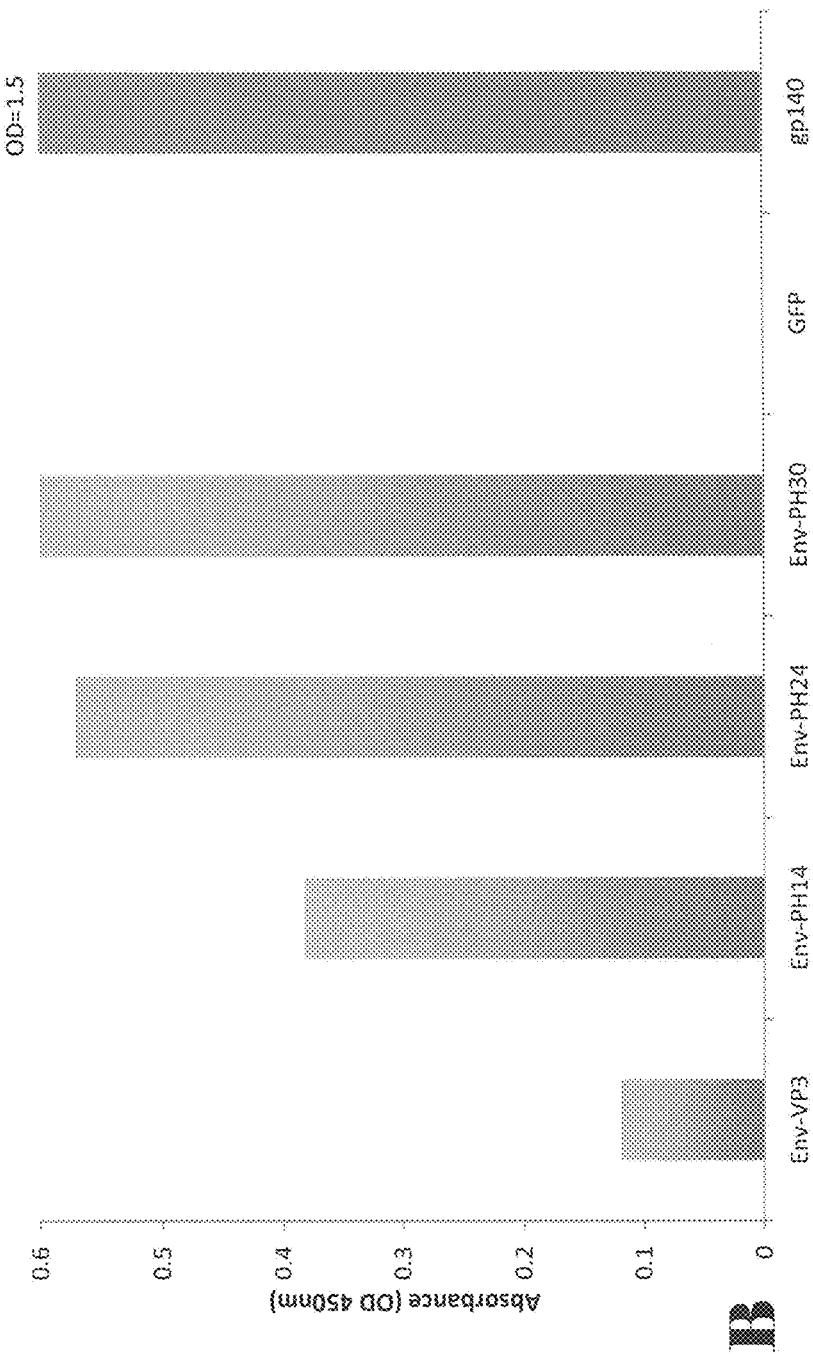
Figure 7C:
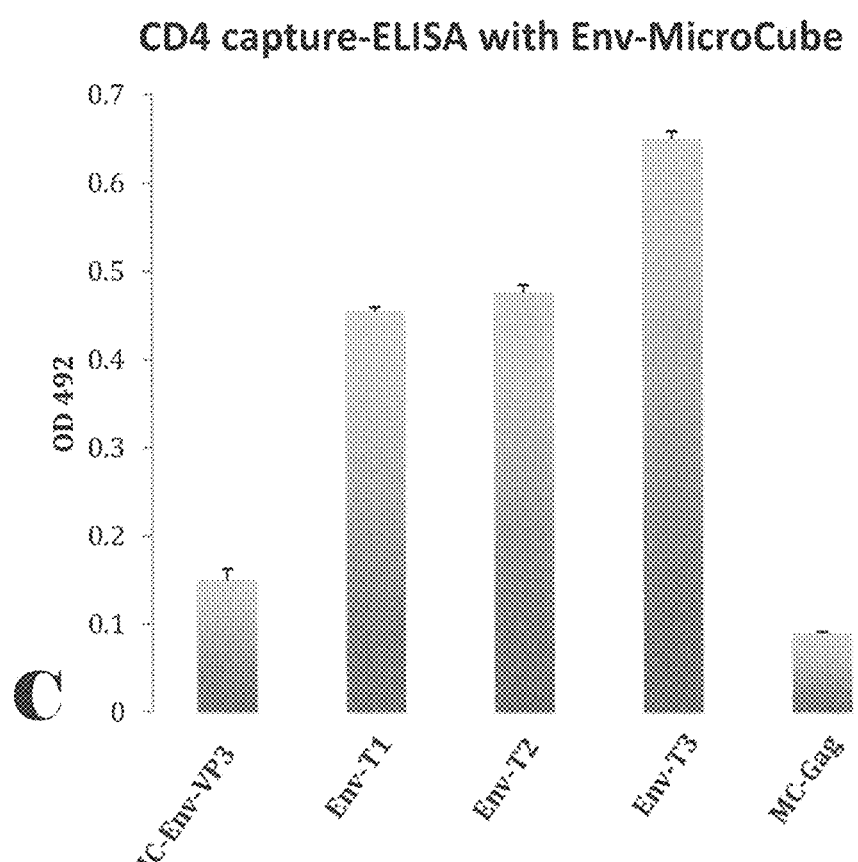
Figure 7D:
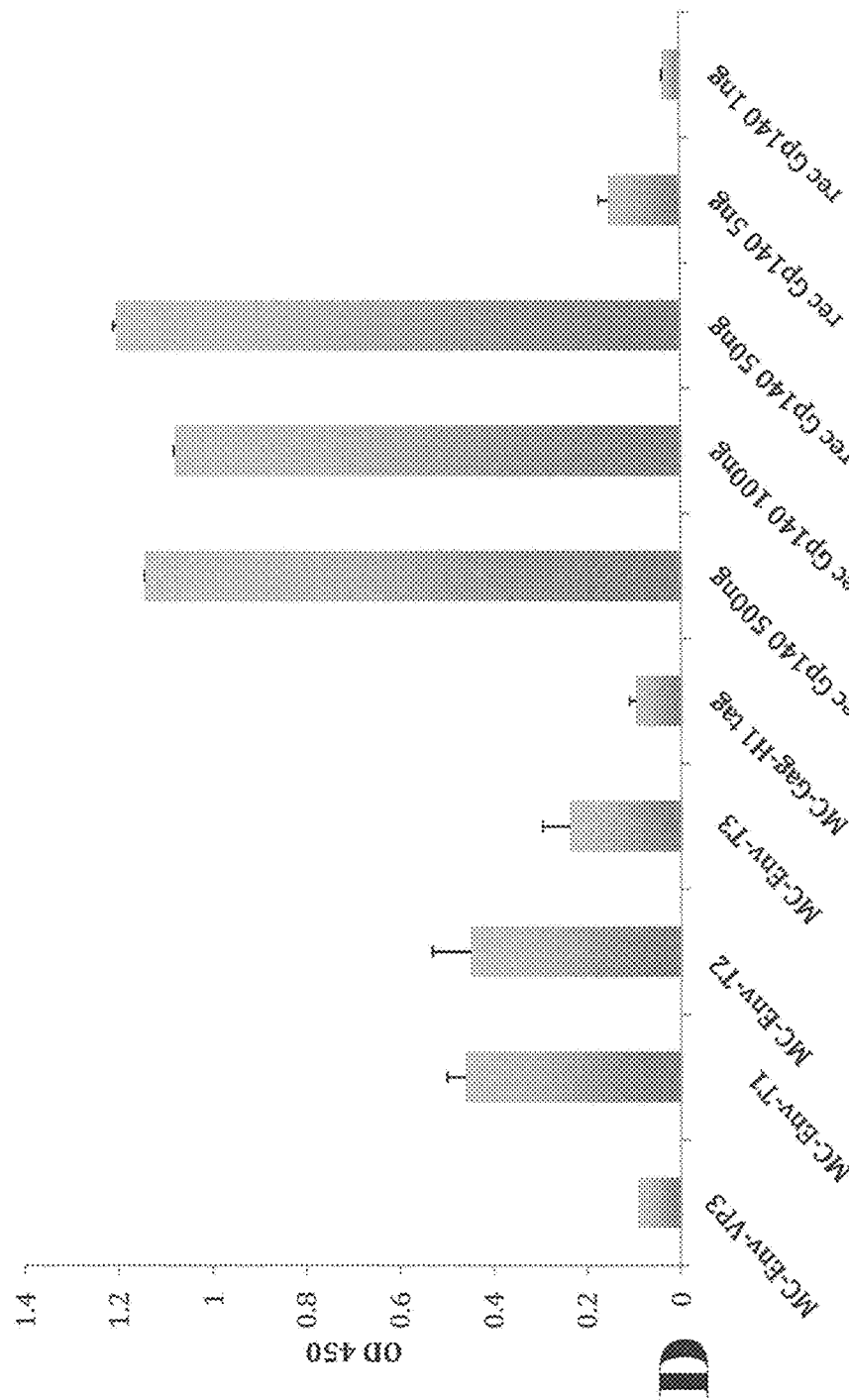

Described herein is a method that allows the incorporation of full-length functional membrane protein into crystals of the cypovirus polyhedrin protein. This method does not introduce foreign protein sequences beyond the sequences of the polyhedrin and the target. The applicability of this method using two non-related membrane glycoproteins that represent major vaccine targets for HIV and flu respectively is provided.

Engineering and Production of PH-MicroCubes

PH-MicroCubes are produced by co-infection of Sf9 insect cells by two recombinant baculoviruses. The first baculovirus encodes for the polyhedrin protein of cypovirus that typically assembles into cubic crystals in the cytoplasm of infected cells. The second baculovirus is produced using shuttle vectors pMel-PH14, pMel-PH24 or pMel-PH30. Sub-cloning into pFastBac plasmid allows the generation of pFastBac-PH14/24/30-FL containing the gene of interest preceeded by the melitin signal sequence and followed by one of the PH tags (FIG. 2). Transformation of DH10bac cells allow the generation of a recombinant baculovirus that encodes for a fusion between a C-terminal tag called PH14, PH24 or PH30 (described below) and the target protein. Co-infection by these two baculoviruses aims at the formation of mixed crystals where the target protein is embedded into the crystalline matrix of the polyhedrin protein (FIG. 3).

Cypovirus polyhedrin differs from the second class of polyhedrin protein that is produced by unrelated viruses of the Baculoviridae family Cypoviruses belong to the Reoviridae family of dsRNA viruses. They differ from Baculoviridae by their morphology (naked icosahedral particles vs. enveloped rod-shaped particles), the chemical nature of their genome (RNA vs DNA genome), their replication mechanism. Accordingly, their infectious crystals (i.e. polyhedra) appear to have emerged independently and show not similarity at a molecular level (Coulibaly et al, 2009). Engineering of one class of polyhedra cannot be extrapolated to the other class because of these fundamental differences. Additionally, baculovirus polyhedra form in the nucleus and have an external membrane that may complicate their use for biotechnological applications.

The representative PH tags represent the C-terminal part of the cypovirus polyhedrin protein deleted from its first 13, 23 and 29 residues (FIG. 4).

Engineering of PH-MicroCubes Incorporating Antigenic Env Proteins of HIV

While the packaging capacity of H1-MicroCubes allows incorporation of large cargo proteins such as growth factors 7 and HIV using the N-terminal tag called H1, these crystals assemble in the cellular cytoplasm when surface proteins of most viruses fold and mature in the secretory pathway. To overcome this limitation of the H1-tag, a novel strategy to direct the incorporation of glycoproteins in MicroCubes was developed. This approach is based on C-terminal sequence tags fused to the cytoplasmic tail of full-length Env (HIV-1 gp160) (FIG. 4). It is proposed and enabled herein that fragments of the polyhedrin protein called PH14, PH24 and PH30 interact tightly with the native polyhedrin thereby directing the fusion protein to the forming crystal. Molecular modeling predicts that these tags fold independently and adopt a trimeric structure that will stabilize a trimeric assembly of the protein attached to these tags (FIG. 4). Env MicroCubes were produced with the 3 different PH-tags showing that the best incorporation is achieved for PH30 (FIG. 5) Immunofluoresence showed that the Env protein is present at the surface of MicroCubes and is folded correctly, as shown by ELISA using the VRC01 conformational mAb (FIG. 6).

Analysis of the antigenicity of the protein showed that Env PH-MicroCubes are recognised by a panel of conformational antibodies (FIG. 7A-B). Most of the antibodies described in FIG. 7B exhibit a broadly neutralizing activity supporting the relevance of this antigen for vaccination.

These MicroCubes are also recognised by sera from HIV-positive subjects supporting the fact that Env is folded natively (FIG. 7D).

To demonstrate that Env at the surface of PH-MicroCubes is functional, a CD4-capture ELISA was established (coating=Env PH-MicroCubes; capture of soluble CD4; detection with the OKT4 anti-CD4 antibody). Specific binding of CD4 was observed compared to the negative control (Gag H1-MicroCubes) (FIG. 7C).

Figure 8A:
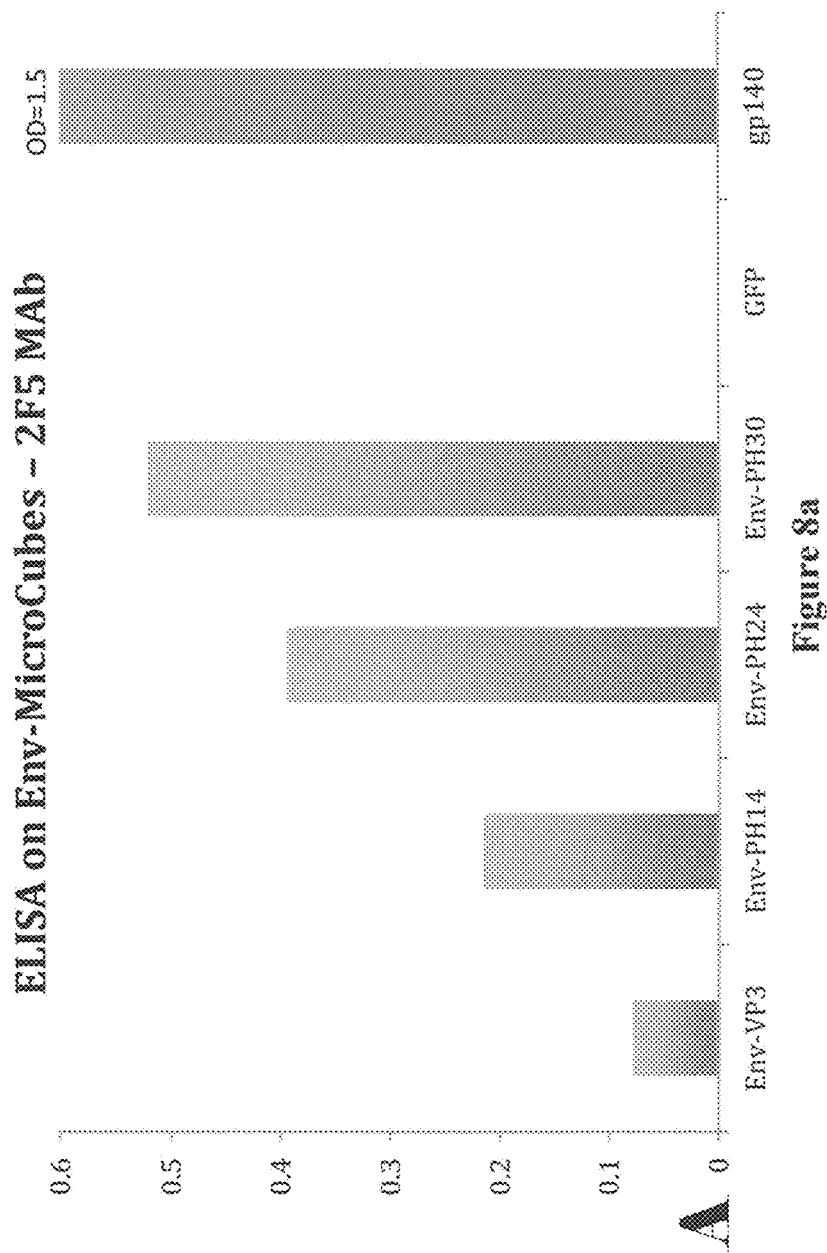
FIG. 8. Env PH-MicroCubes present more efficiently MPER epitopes known to induce broadly-neutralizing antibodies.
Figure 8B:
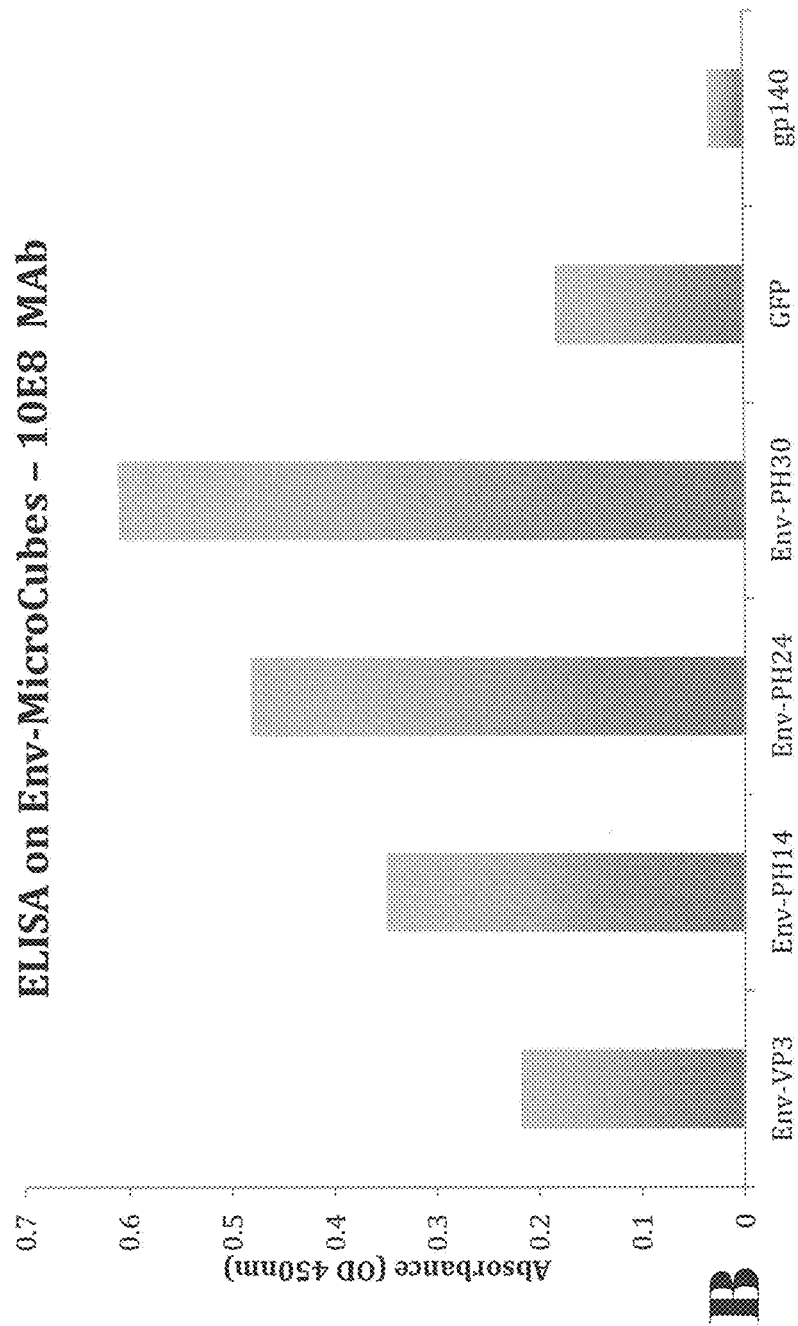

Recognition of epitopes in the membrane proximal region (MPER) was tested. It was hypothesised that in soluble constructs this region may be partially disordered or altered. Confirming this hypothesis, Env PH MicroCubes were strongly recognised by mAb 10E8 when responses to their soluble counterpart gp140 was very weak comparatively (FIG. 8). These conserved epitopes have been described as a vulnerability site of the Env protein and are of particular interest for the production of broadly-neutralising antibodies required for a viable HIV vaccine. The present description enables the incorporation of Env into PH-MicroCubes as an intact full-length membrane protein. In this context, Env is antigenically native and functional for the binding of the receptor molecule CD4. Importantly, Env PH-MicroCubes presents epitopes of interest for the development of an HIV vaccine.

Engineering of HA-PH Microcubes

Figure 2:
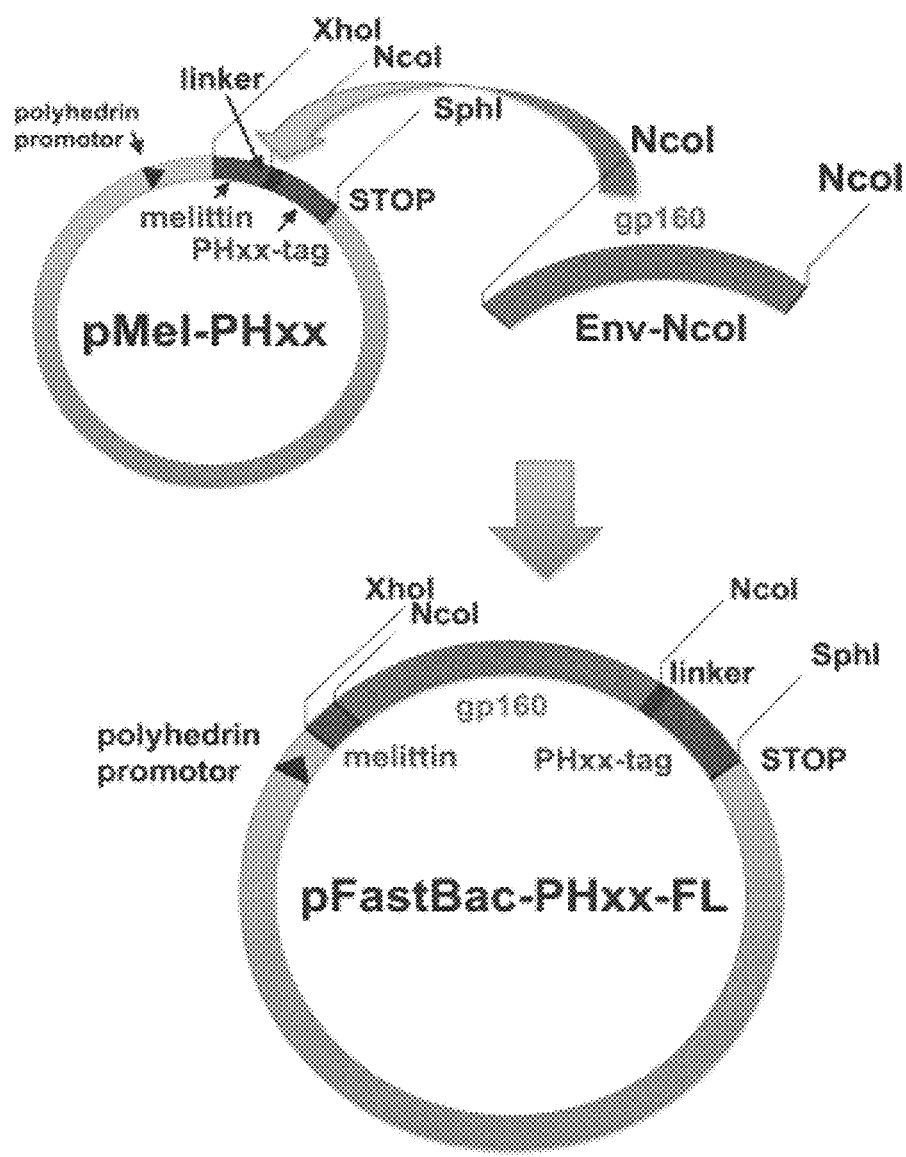
FIG. 2. Transfer vector pMel-PH for the production of the pFastBac-PH vectors.
Figure 3:
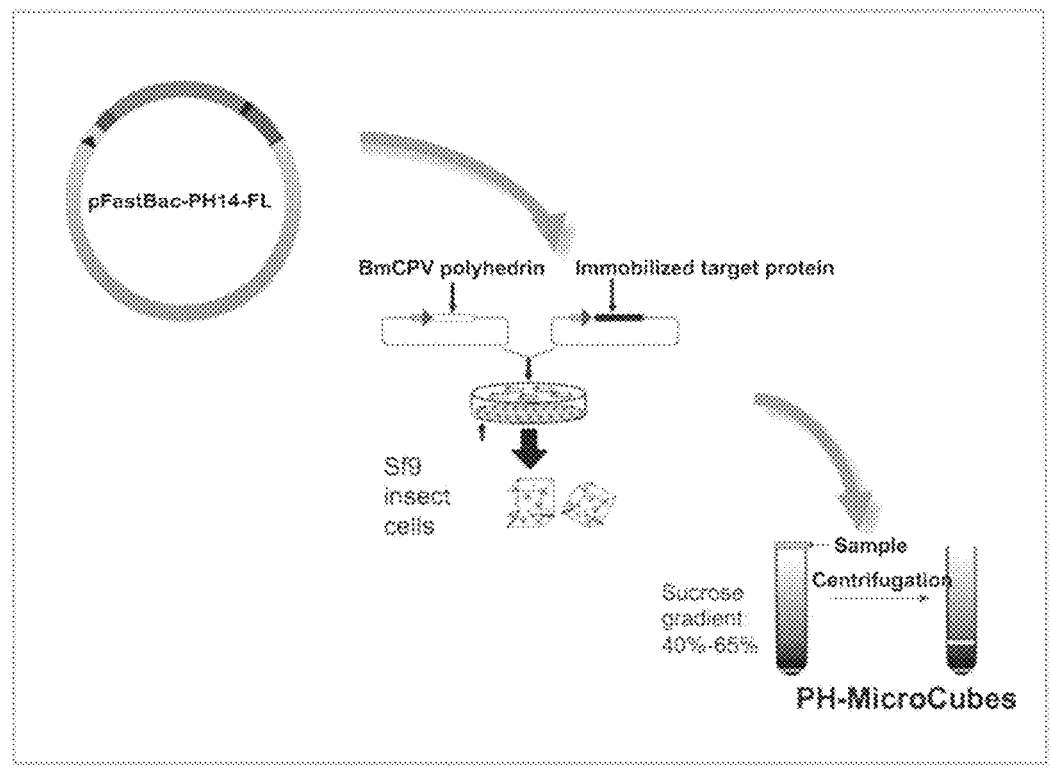
FIG. 3. Schematic showing production of PH-Micro-Cubes.
Figure 4:
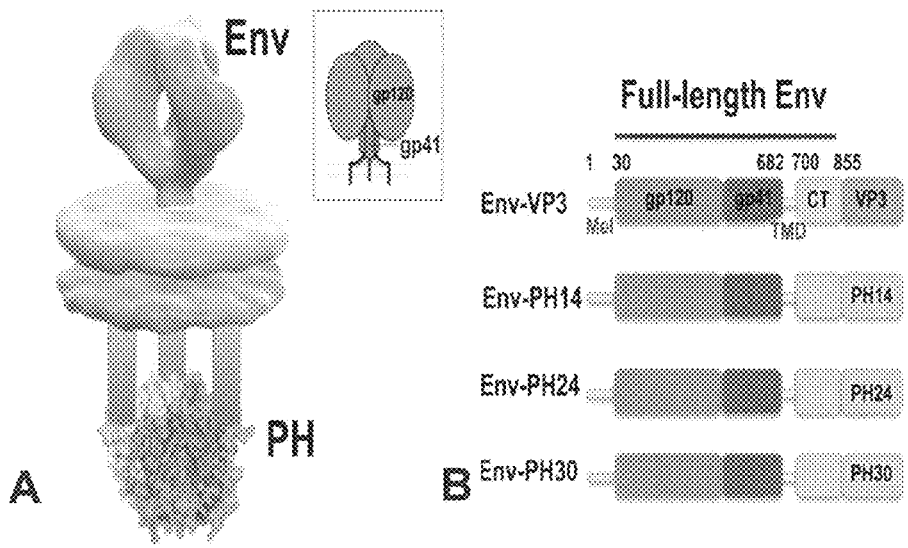
FIG. 4. Env MicroCube design and characterization. A. Env-MicroCube Schematic representation. B. 3D Representation of the Env-PH30 trimer. C. Env Expression using the Env-PH30 construct. D. Western blot analysis of Env Micro-Cubes showing successful incorporation of Env. E. SDS-PAGE analysis of 1 µg of MC. F. ELISA tests with ENV-MicroCubes probed with the conformation Mab VRC01 (left) and CD4 binding analysis using the anti-CD4 OKT4 Mab.
Figure 5:
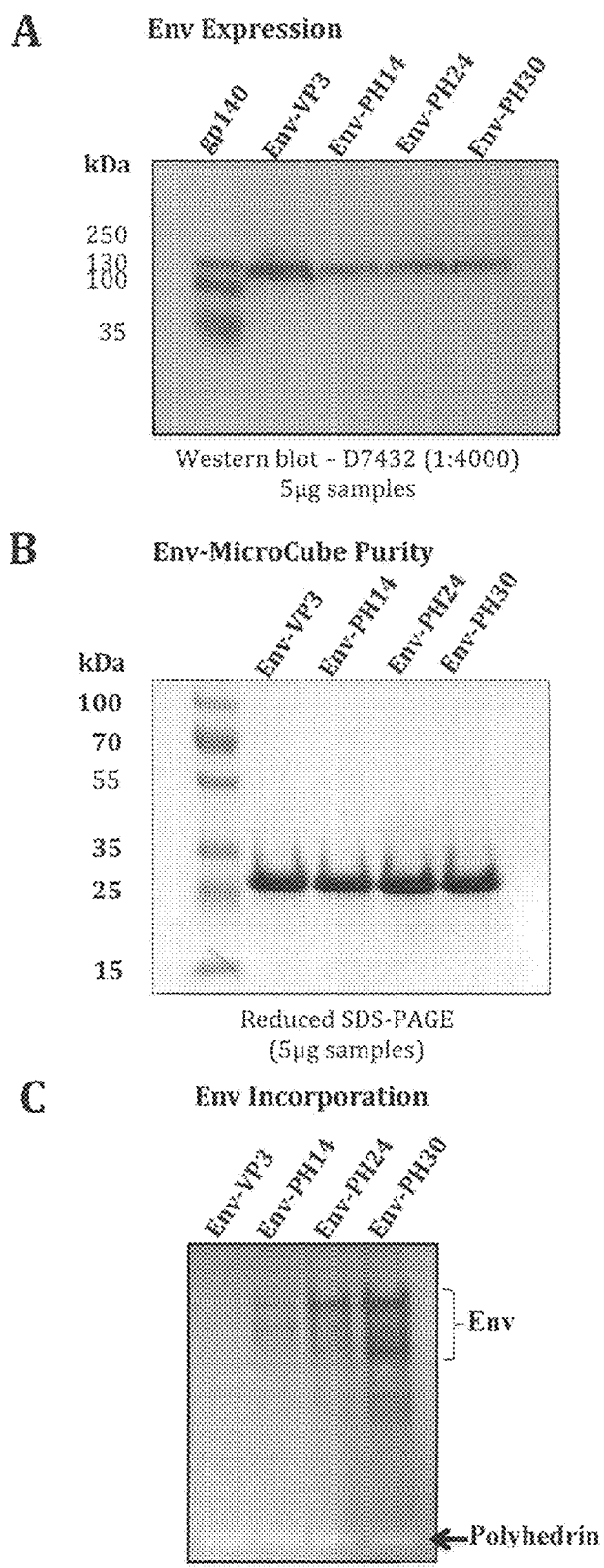
FIG. 5. Env-PH expression and incorporation into PH-MicroCubes. Note the low incorporation of Env-VP3 in BmCPV polyhedrin crystals despite similar levels of expression.
Figure 6:
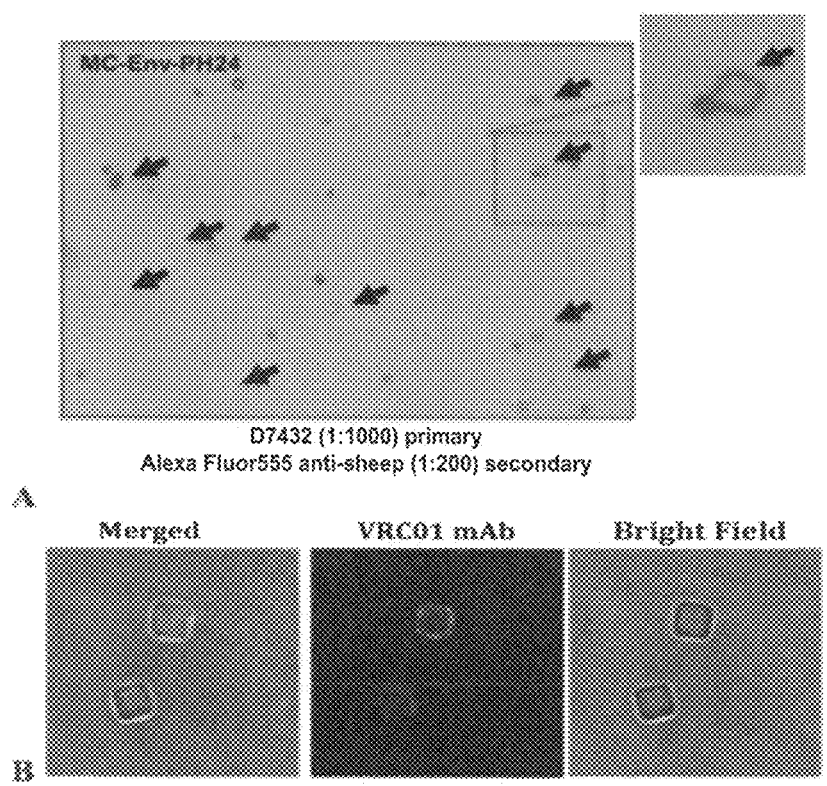
FIG. 6. Env PH-MicroCubes present Env on their surface recognised by the conformational antibody VRC01.
Figure 9:
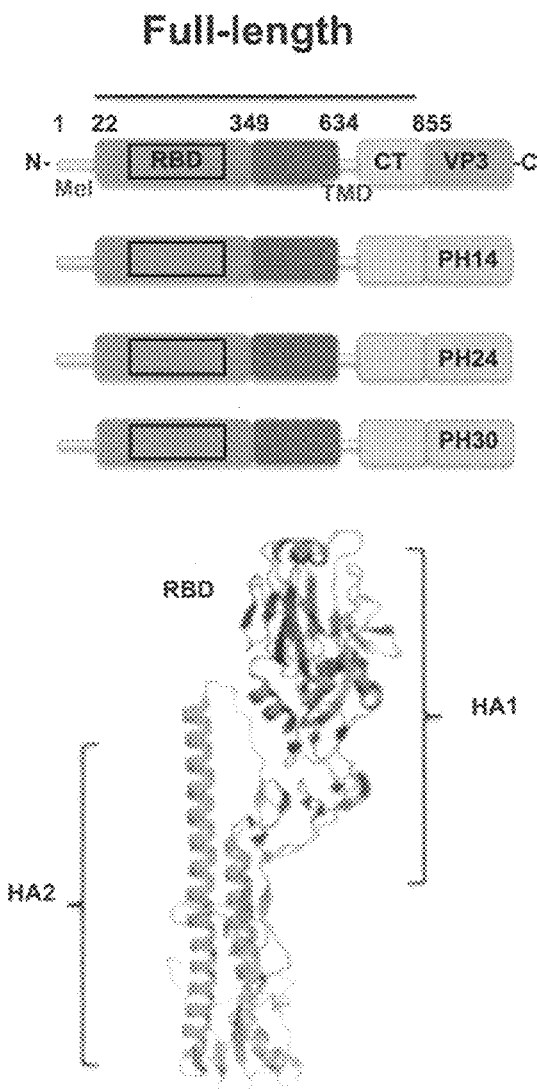
FIG. 9. Schematic representation of HA-PH constructs. The antigens were fused to the VP3, PH14, PH24 or PH30 tags. HA: haemagglutinin Influenza protein, CT: cytoplasmic tail, TMD: trans-membrane domain, RBD: Receptor Binding Domain. Mel: Honeybee Melittin signal peptide.

HA PH-MicroCubes were engineered with the same protocol as Env PH-MicroCubes (FIG. 2 and FIG. 3). Constructs are described in FIG. 9 and correspond to the full-length HA including the head and stalk domains (i.e. HA1, HA2, the trans-membrane domain and the cytoplasmic tail). The strain used for all constructs is A/PR8 (H1N1).

Figure 10:
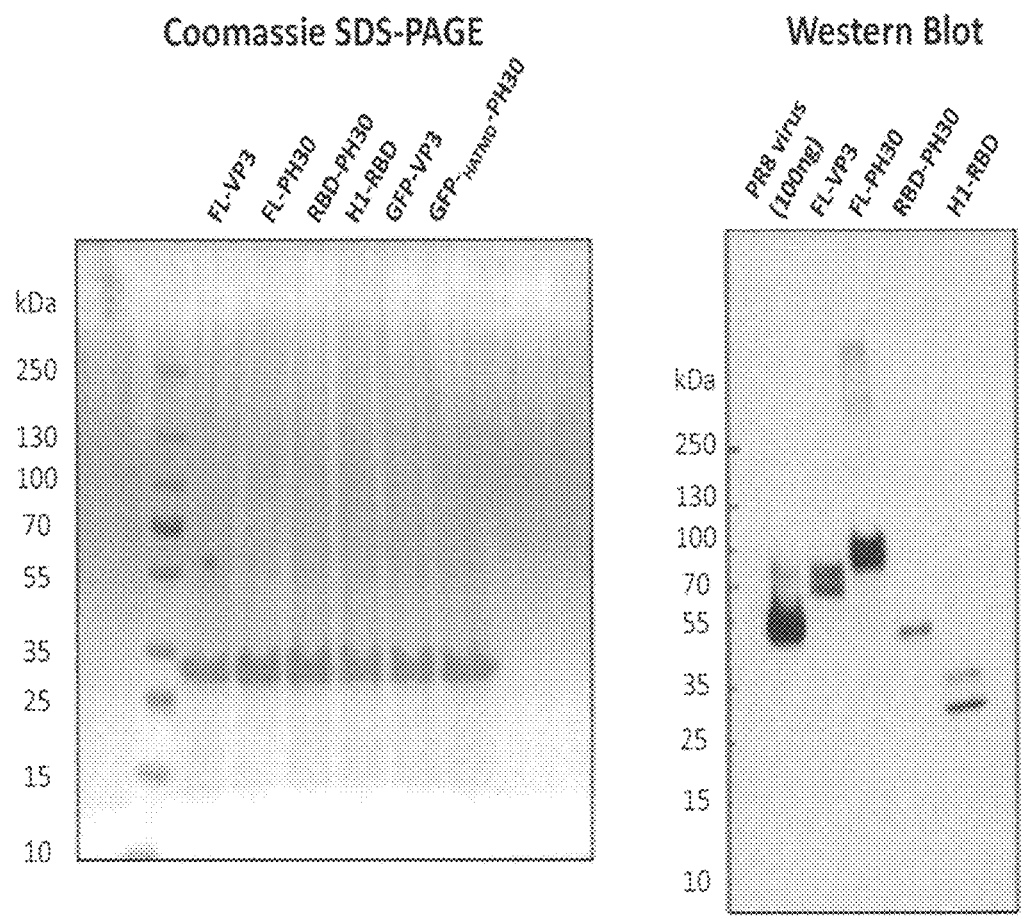
FIG. 10. Influenza MicroCubes. SDS-PAGE analysis (left) and Western blot (right) of Sf9 cells that were co-infected with two recombinant baculoviruses expressing HA derived antigens and BmCPV polyhedrin. Samples were collected 48 h post-infection and HA MicroCubes highly purified from the insoluble fraction by differential centrifugation and sucrose gradient. PR8=63.3 kDa, FL-VP3=71.3 kDa, FL-PH30=90.0 kDa, RBD-PH30=51.3 kDa, H1-RBD=28.9 kDa. Note the slightly higher incorporation in FL-PH30 compared to the old VP3 tag (Kyoto patent) and H1 tag (H1 MicroCubes).

Full-length HA expressed as a trimer and including its trans-membrane domain is the main target for neutralizing antibodies elicited for example by split vaccine or recombinant HA. While this would be the favoured antigen to be tested in murine studies, incorporation of a trimeric membrane glycoprotein into MicroCubes had never been attempted. A number of factors complicate expression because of the requirement for translocation into the ER compartment for correct folding of full-length HA. MicroCubes form cytoplasmically, HA must therefore be captured along its trafficking path to the plasma membrane, potentially limiting the amount of HA that will be incorporated into MicroCubes. Despite this, the Full-length HA antigen was successfully incorporated in MicroCubes using the PH30 tags (FIG. 10). This is the optimal antigen with the potential to induce strong, long-lasting protection from a lethal challenge and possibly cross-neutralizing antibodies. Incorporation of approximately 2-3 ng of HA antigen per ug of crystal was achieved. These levels are sufficient for immunogenicity studies and demonstrate that incorporation of membrane glycoprotein into MicroCubes can be achieved.

Analysis of Influenza Antigen Expression by ELISA

Figure 11:
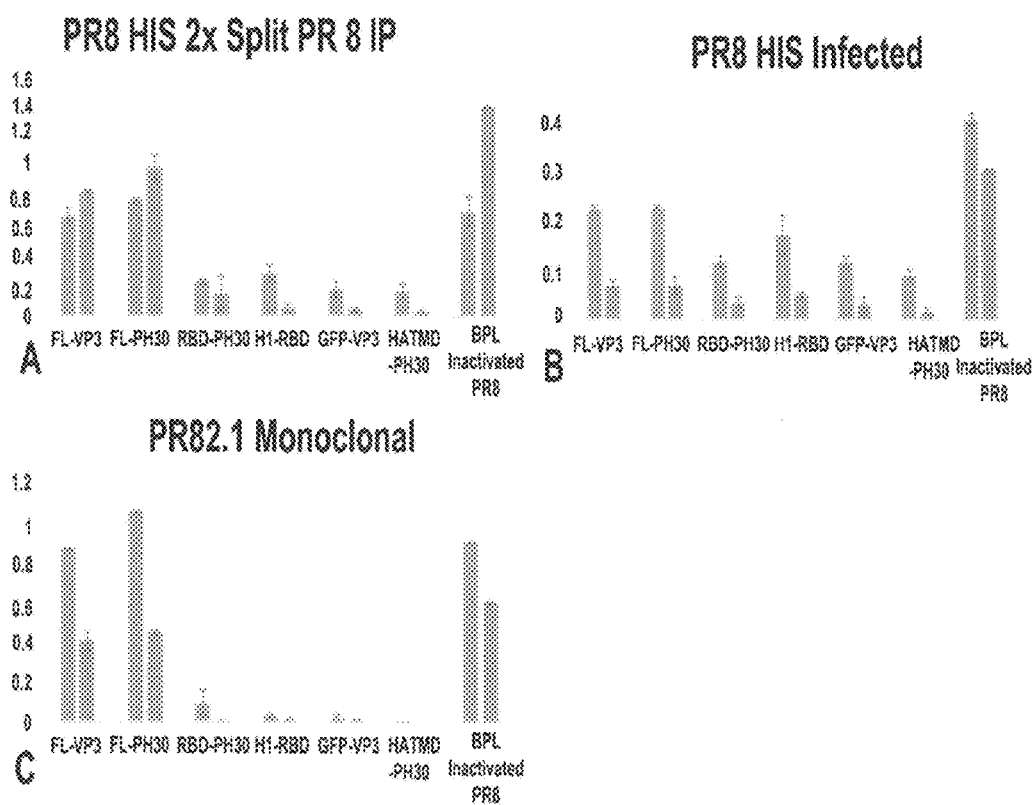
FIG. 11. Antigen expression at the Surface of Influenza MicroCubes determined by ELISA. MicroCubes were coated overnight in a 96-well plate, and the ELISA was performed using (A) Hyper Immune Sera from mice immunized twice with the Split PR8 Vaccine (prepared by CSL for LB), (B) Hyper Immune Sera from mice injected twice with PR8 virus or (C) using a MAb PR82.1. Blue: primary antibody diluted at 1:100, orange: 1:1000.

To confirm the presentation of HA at the surface of PH-MicroCubes, direct ELISA tests were performed by coating a 96 well plate with the MicroCubes (20 µg/well) in Carbonate Buffer. In FIG. 11 and text below FL refers to the full-length HA as described above while RBD is the receptor binding domain used as a control. Inactivated PR8 viruses serves as a positive control. The results indicate that both the FL-PH30 constructs express large amounts of antigens as detected by a hyper-immune serum (HIS), a serum from infected mice (PR8 HIS infected) and the PR82.1Mab antibody, probably directed against the stalk region (FIG. 11).

Figure 12:
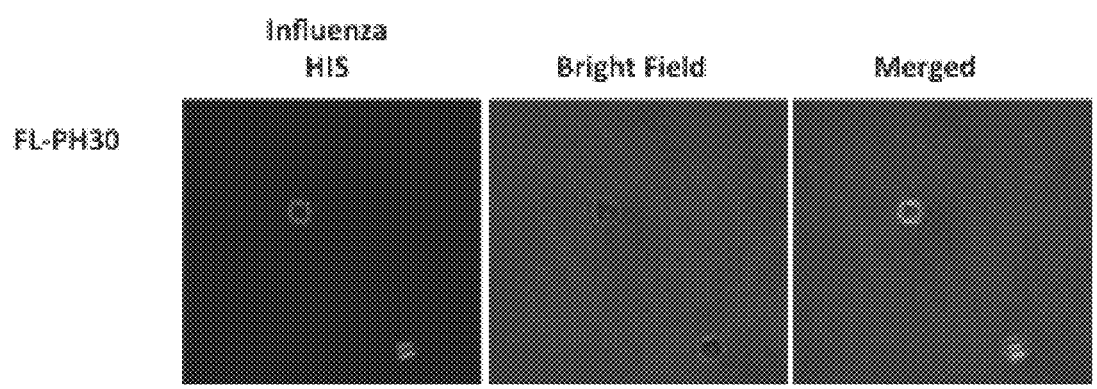
FIG. 12. Confocal Microscopy indicating the expression of the Full-Length (FL) HA at the surface of the PH30-MicroCubes.

To confirm the antigen presentation at the surface of PH-MicroCubes, confocal microscopy was performed using hyper immune sera from mice immunised twice the PR8 split vaccine (obtained from Prof. Lorena Brown). As observed in FIG. 12, FL PH30-MicroCubes expressed the HA FL antigen at very high levels at their surface.

Figure 13:
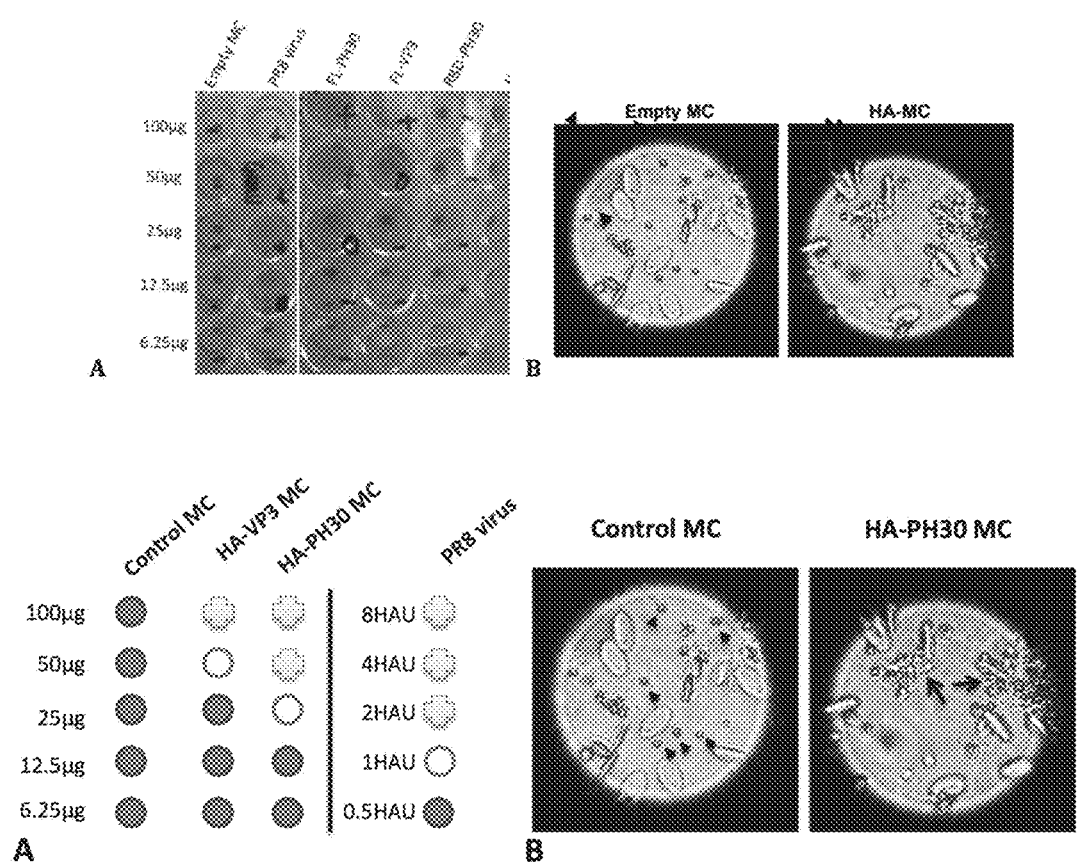
FIG. 13. Hemagglutination Assays using PR8 Influenza virus (control) or Microcubes exposing Influenza antigens. Top A/B. 2-fold virus dilutions (from 1:4 to 1:4096) and different MicroCubes concentrations were applied to a 0.1% RBC dilution for 30 min. The titer is calculated from wells where lattice formation is observed. Bottom A/B. A. Serial dilutions of PR8 virus (8 HA units to 0.5 HA units) and MicroCubes (MC; 100 µg-6.24 µg) were incubated with a 0.1% dilution chicken red blood cells for 30 min at room temperature. Responses are schematized by a filled circle for the absence of hemagglutination (button morphology); an open circle for partial hemagglutination (co-existing button and shield morphologies); a cross for complete hemagglutination (shield morphologies). B. Optical microscopy of control MC (left panel) and HA-PH30 MC (right panel) incubated with chicken red blood cells. Examples of isolated crystals are indicated by arrowheads. Full arrows indicate clusters of crystals that adhere to the surface of the red blood cells suggesting that these MicroCubes present a functional form of the HA receptor.
Figure 20:
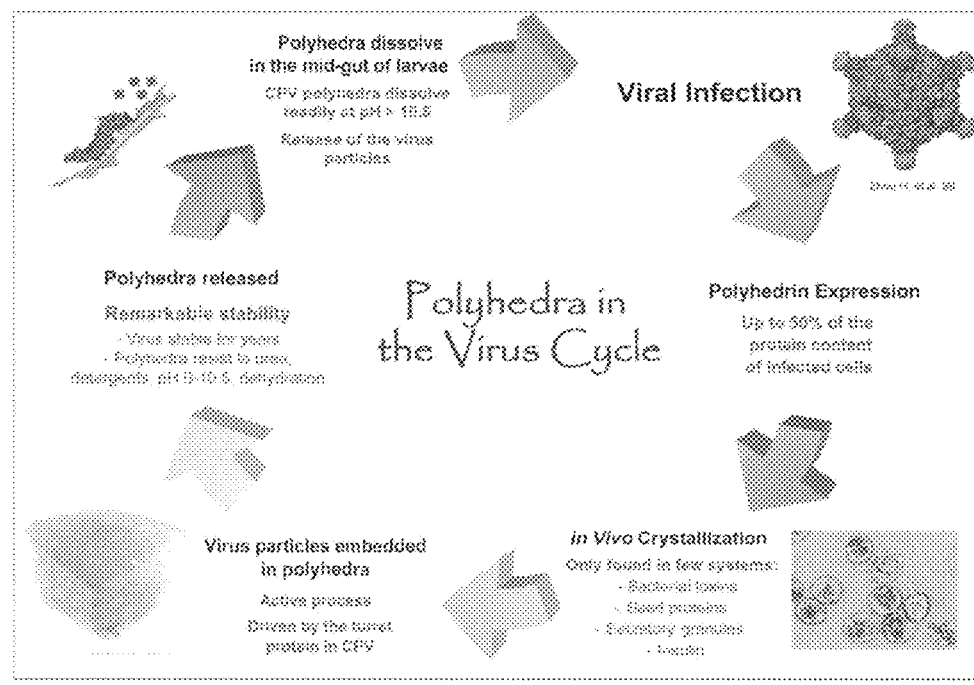
FIG. 20 is a diagram illustrating the role of polyhedra in the virus life cycle.
Figure 21:
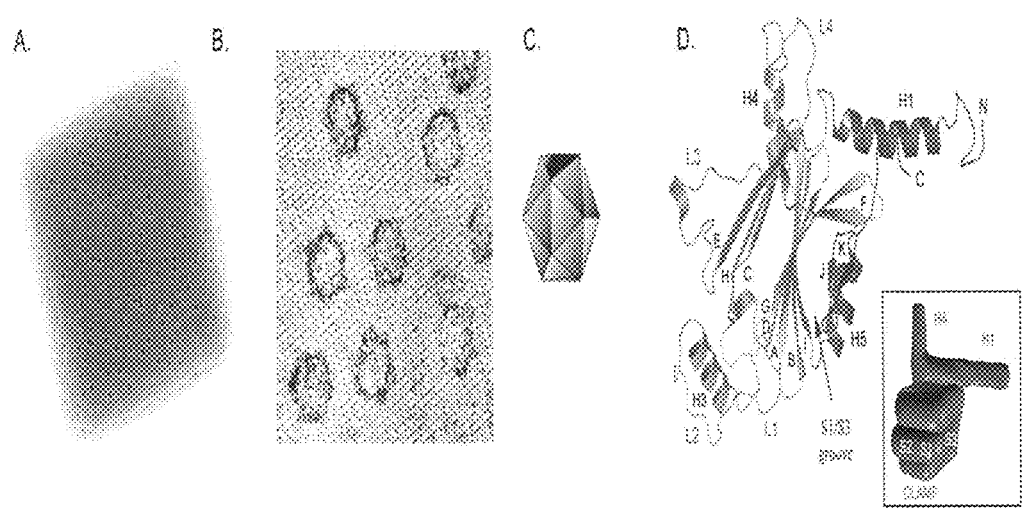
FIG. 21. Structure of cypovirus polyhedra. (A) Scanning electron microscopy, (B) thin section electron microscopy, (C) schematic representation of the virus particles, (D) cypovirus polyhedrin protein structure.
Figure 22:
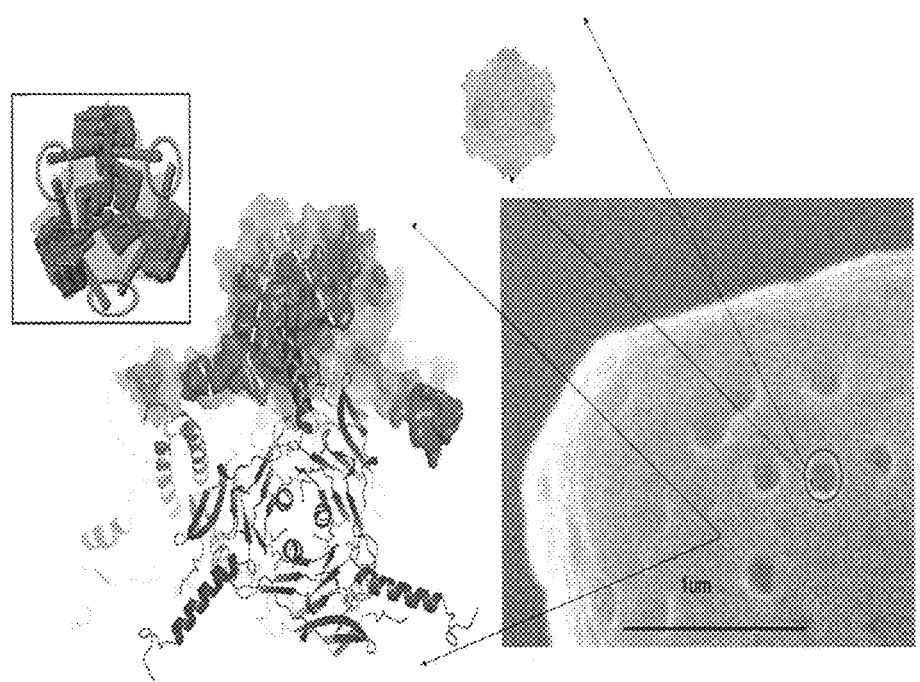
FIG. 22. Central role for the H1 helix in the organisation of cypovirus. The structure of the polyhedrin of the polyhedrin of the silkworm cypovirus (BmCPV) is represented in a ribbon diagram for 3 visible trimers and in a red surface for the fourth trimer. The inset provides a schematic representation of the molecular organisation. The 8 trimers are represented in blue and red with each subunit of the polyhedrin drawn as a pointing left hand. The pivotal role of the N-terminal helix H1 is highlighted by circles. The right panel places the unit cell on an infectious polyhedra seen by scanning electron microscopy. The position of the unit cell is indicated by a small red square and the location of a virus particle is circled in red. A 2 µm polyhedra typically contain about 8 million unit cells and several thousands of virus particles.
Figure 23:
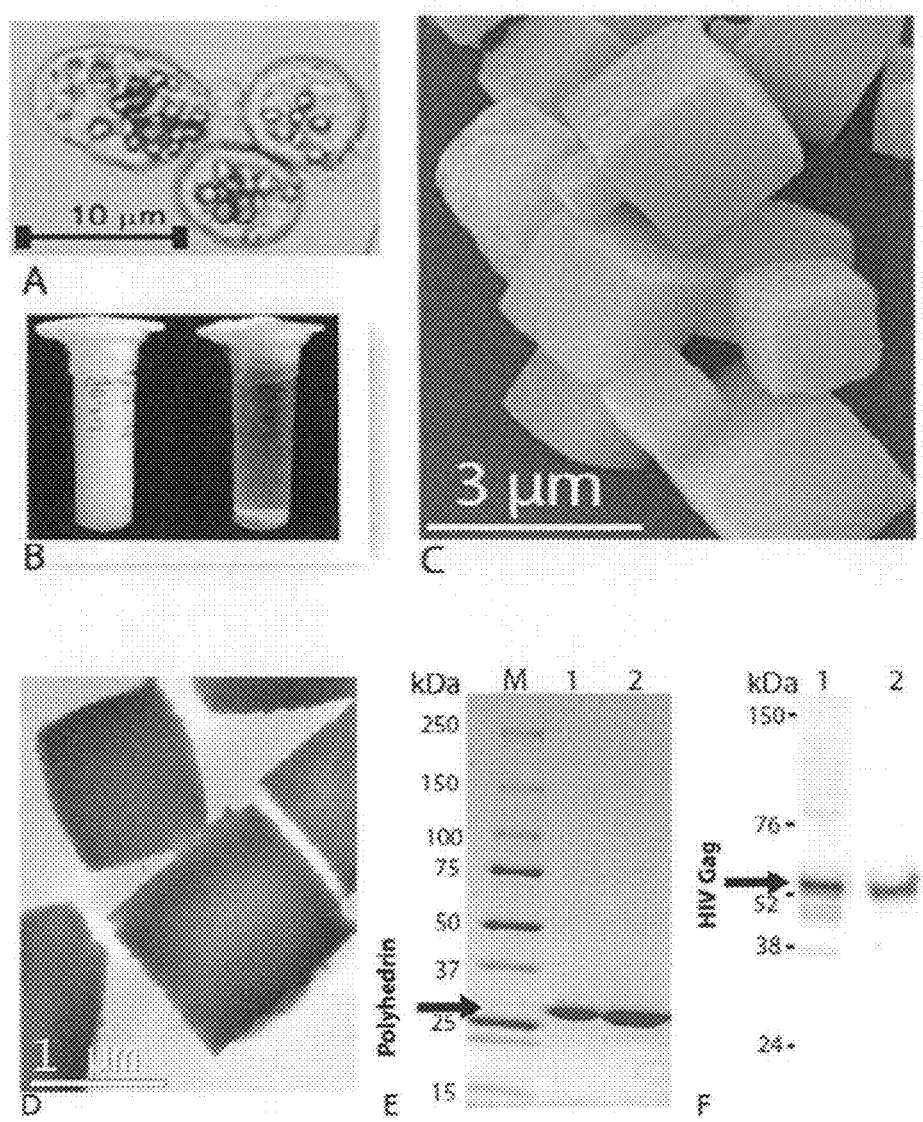
FIG. 23. Gag MicroCubes: polyhedra incorporating recombinant HIV Gag fused to the H1-Tag. (A) Sf9 co-infected by recombinant baculoviruses expressing the BmCPV polyhedrin and H1-Gag proteins. (B) Gag microcubes have an extremely dense crystalline matrix and rapidly sediment into a white paste. (C,D) Scanning electron microscopy (EM) and thin-section transmission EM of purified Gag microcubes. The incorporation of Gag does not disrupt the crystalline matrix. (E) SDS-PAGE analysis of 1 µg (lane 1) and 2 µg (lane 2) of microcubes. (F) Western blot analysis of Gag microcubes in comparison with recombinant Gag showing successful incorporation of full-length p55.
Figure 24:
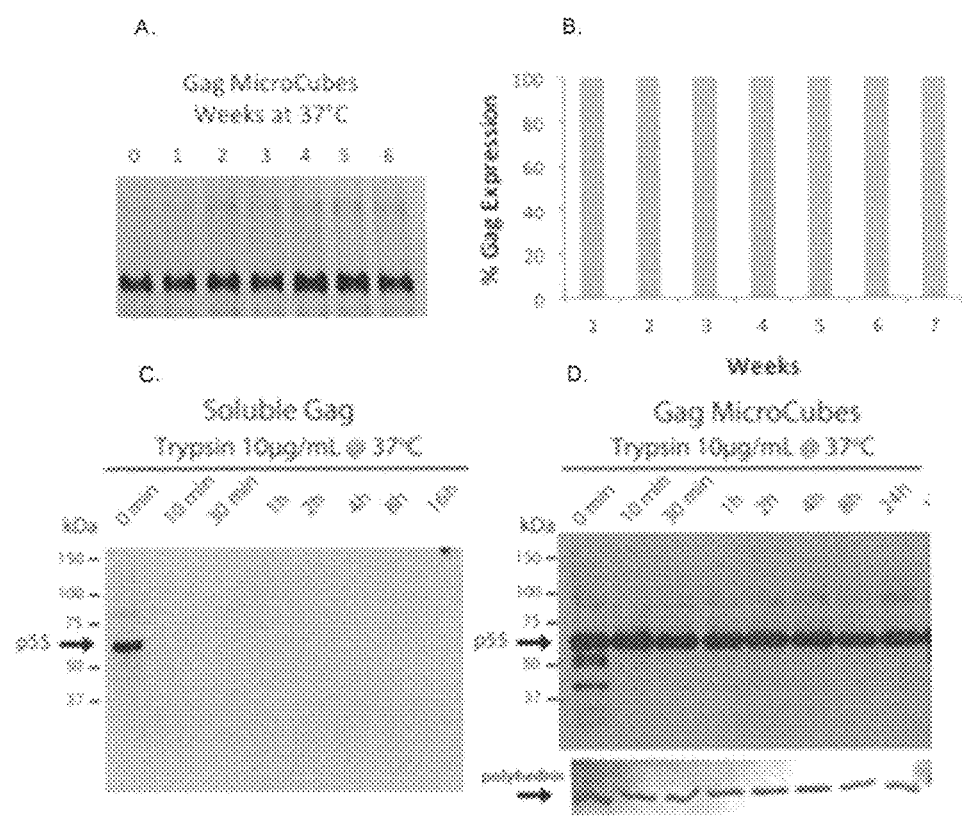
FIG. 24. Gag in MicroCubes is protected from heat denaturation and proteolytic degradation. (A-B) Soluble Gag and Gag MicroCubes were dried for 0-7 weeks incubated at 37° C. and resuspended at the indicated time points. Western blot were then scanned and the intensity of the gag protein was quantified using a Typhoon 9400, revealing no significant degradation of Gag MicroCubes. (C,D) Western blot analysis of soluble Gag and Gag MicroCubes incubated with 10 m/mL of trypsin.
Figure 25:
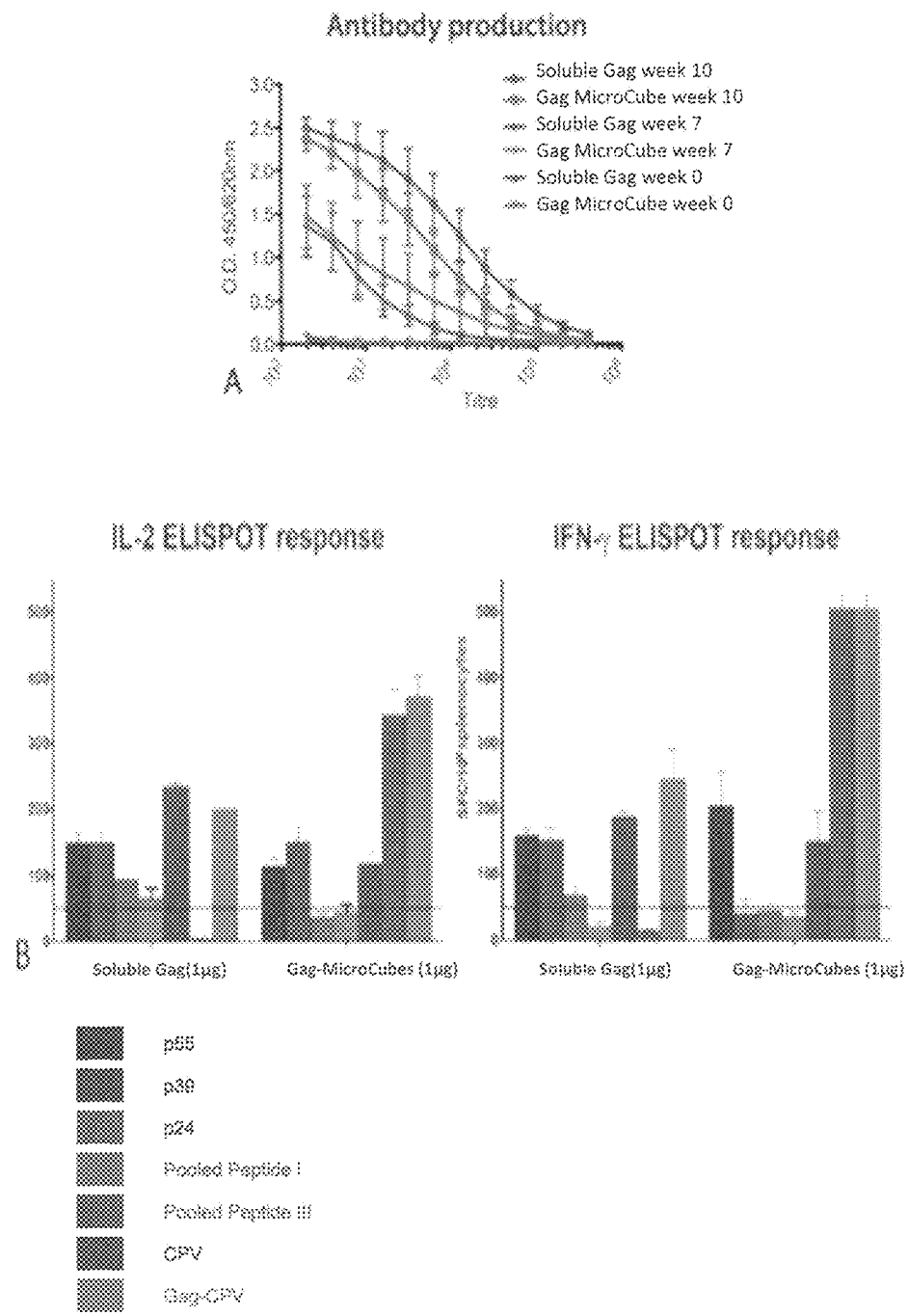
FIG. 25. Gag MicroCubes elicit strong humoral and cellular immune responses in mice. (A) ELISA titre of sera from mice (n=8) immunized with 5 µg of soluble Gag (blue) or Gag MicroCubes (red) at week 0, 7 and 10. The coating antigen is soluble Gag. (B) IL-2 and IFN-g ELISPOT responses of splenocytes from mice (n=8) immunized with 1 µg of soluble Gag or Gag MicroCube, $5 \times 10^5$ splenocytes were stimulated with p55, p39, p24, pooled peptides I and II, MicroCubes and Gag MicroCubes as noted in the inset. Negative control: media, Positive control: ConA (data not shown).
Figure 26:
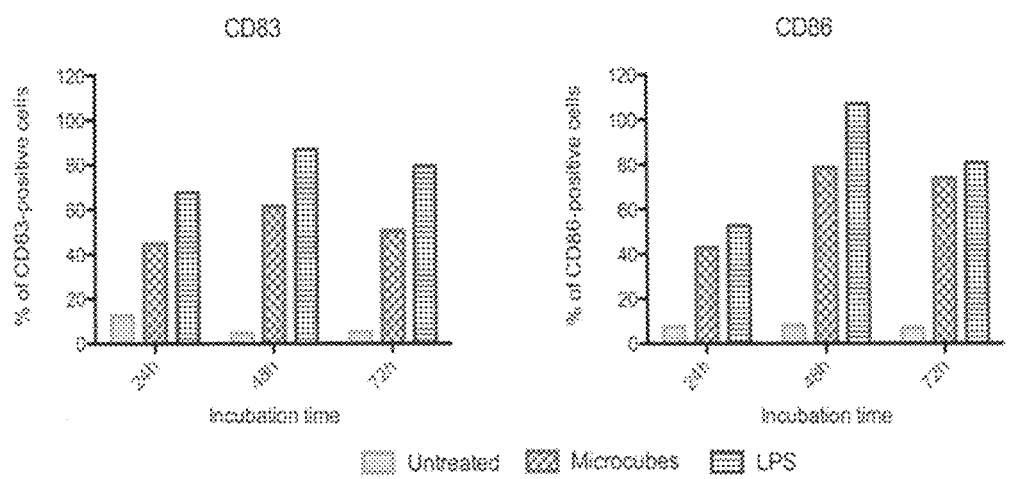
FIG. 26. Uptake of MicroCubes induces DCs maturation. FACS analysis of monocyte-derived dendritic cells surface markers CD83 and CD86 associated with maturation after incubation with MicroCubes. LPS is used as a positive control.
Figure 27:
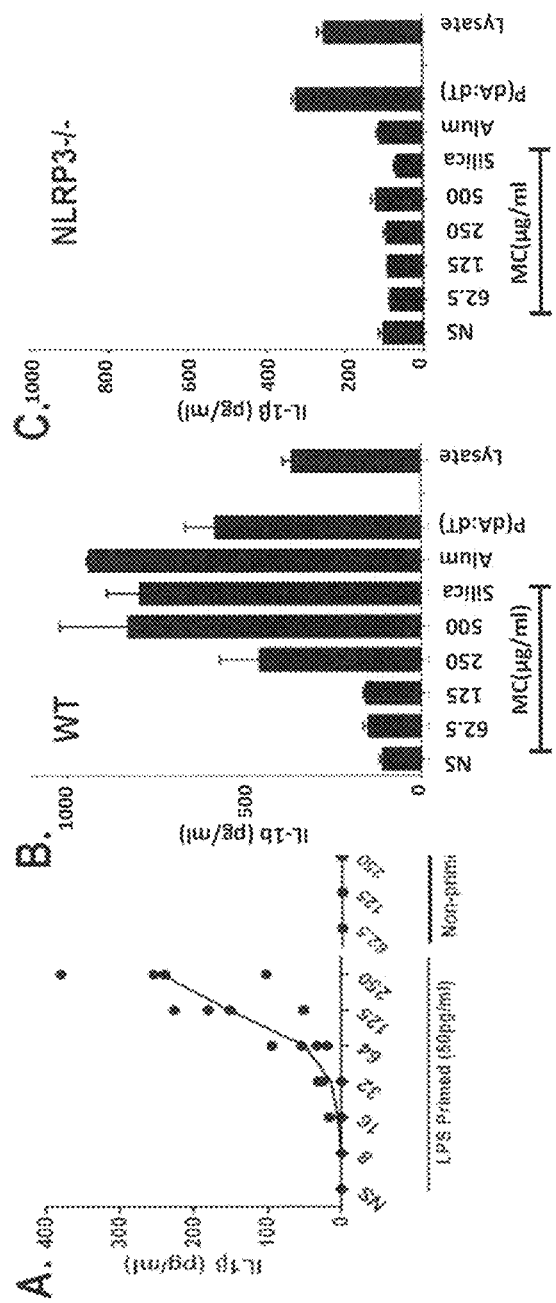
FIG. 27. Macrophage engulfment of MicroCubes activates the NLRP3 inflammasome via lysosomal destabilization. (A) Human PBMCs from 4 individuals were primed with LPS (50 pg/ml) for 3 h, or not, then stimulated with MicroCubes (8-250 mg/m1) for a further 6 h. Bone marrow derived macrophages derived from (B) wild-type, or (C) NLRP3-deficient mice were primed with LPS (100 ng/mL) for 3 h and then stimulated with MicroCubes (62.5-500 mg/ml), silica (125 µg/mL), Alum (250 mg/ml), transfected with poly (dA:dT) (250 ng/ml), or left unstimulated (NS) for a further 6 h. Priming of cells was confirmed by disrupting cellular membranes of unstimulated cells by repeated freezing and analysis of cellular lysate IL-1b concentrations (Lysate). Cultured supernatants were assayed for IL-1β by ELISA.
Figure 28:
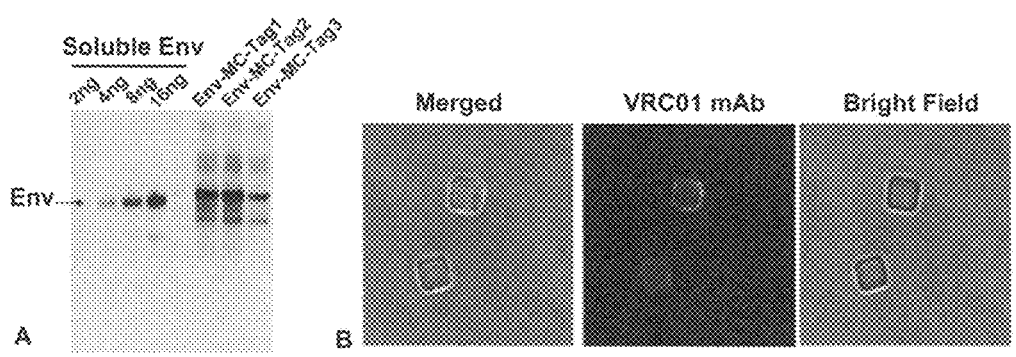
FIG. 28. Env MicroCubes: polyhedra incorporating recombinant HIV Env. (A) Western blot analysis of Env microcubes in comparison with recombinant Env showing successful incorporation of full-length gp160 Env using different tags. (B). Confocal Microscopy indicating the expression of the Env antigen at the surface of the MicroCubes in a native conformation.
Figure 29:
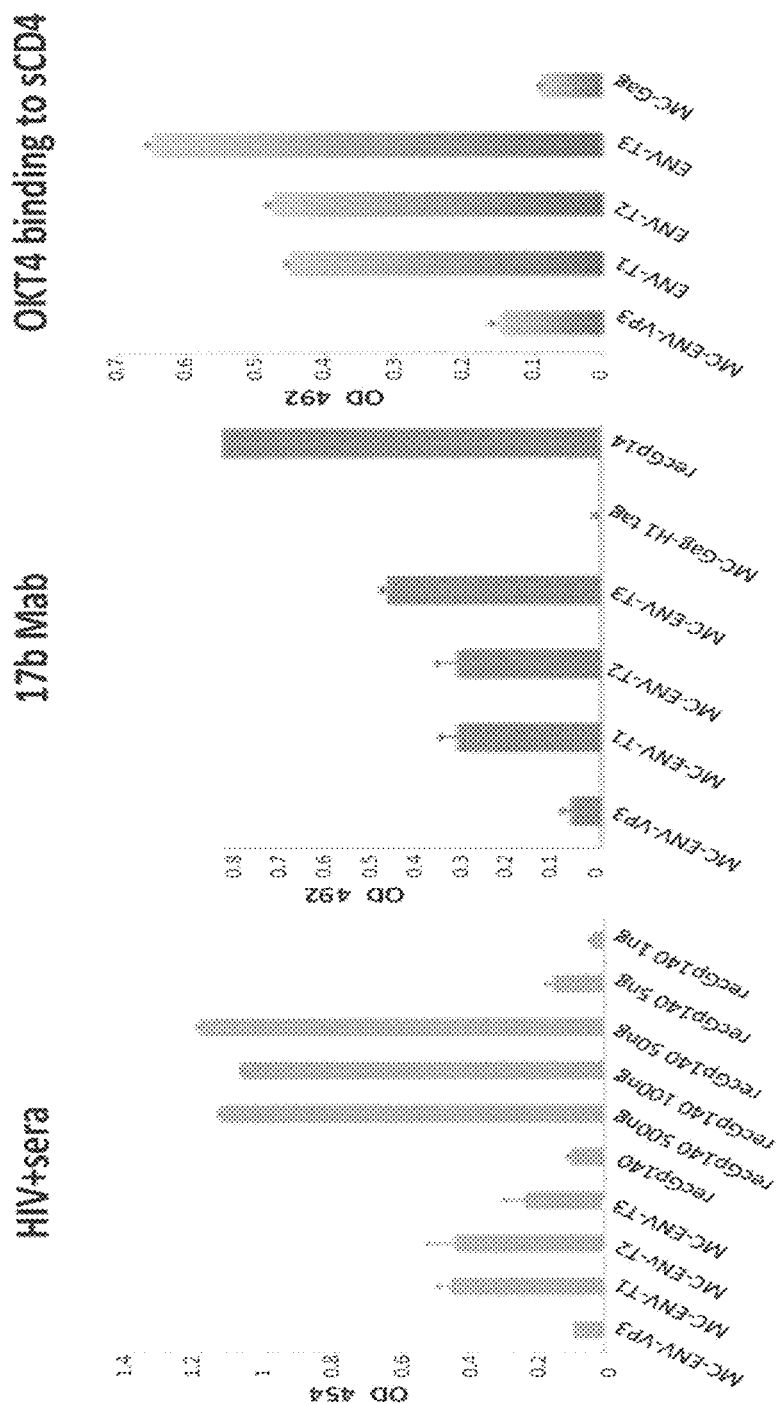
FIG. 29. Env MicroCubes expose epitopes that are recognised by nabs and bind soluble CD4. MicroCubes were coated in ELISA plates (20 µg/well) and ELISA were performed using human sera from HIV positive patients (left), monoclonal antibody 17b (middle) and OKT4 antibody after incubation with soluble CD4.
Figure 30:
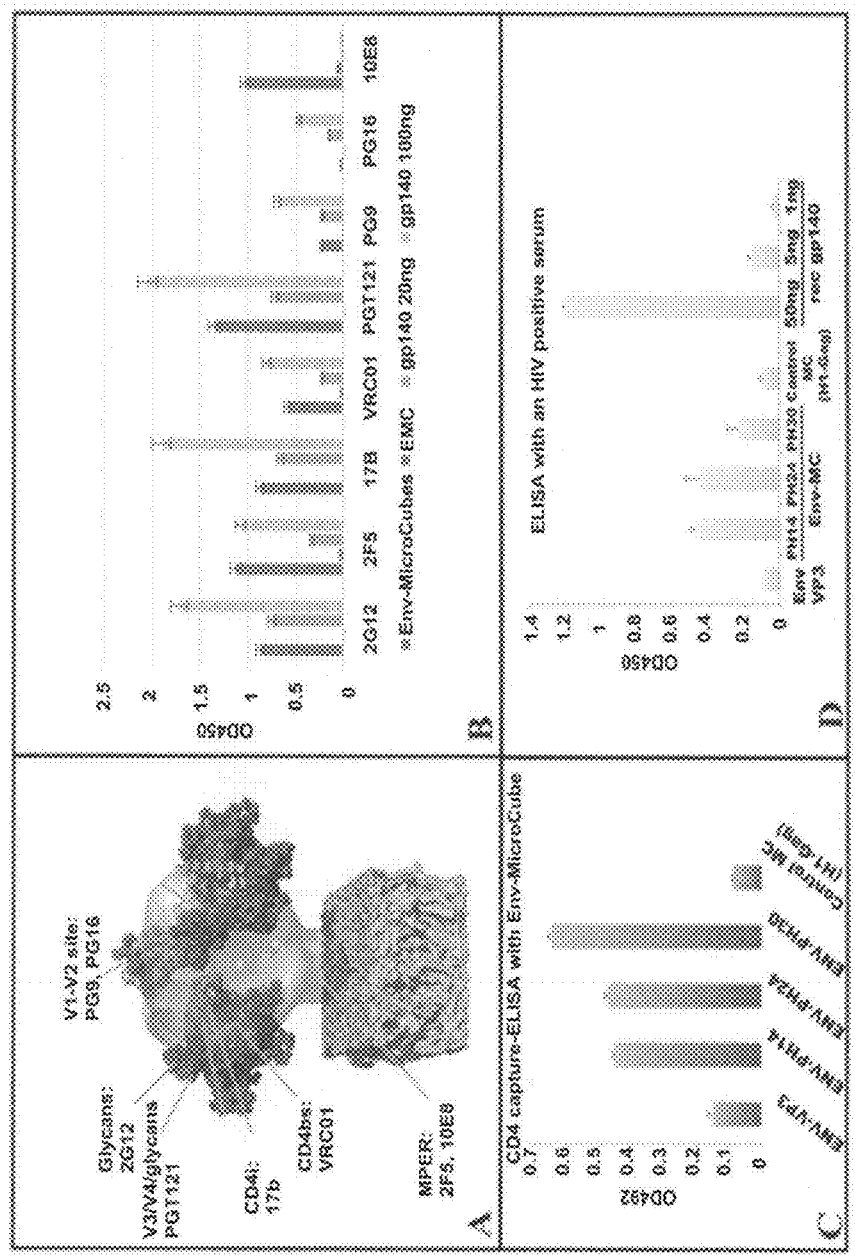
FIG. 30. Env PH-MicroCubes present a form of Env that is antigenically native, recognised by HIV-positive sera and functional. Note the higher recognition of HIV Env for PH tags compared to the old VP3 tag (Env-VP3) in panels C and D. The Env-VP3 is close to background suggesting low incorporation if any.

Analysis of the capacity of Influenza MicroCubes to hemagglutinate red blood cells To assess whether the MicroCubes expressing the FL constructs are able to reproduce the properties of influenza virus particles to hemagglutinate red blood cells (RBCs), hemagglutination assays were performed using decreasing concentrations of MicroCubes as shown in FIG. 13. Only the FL-PH30 and FL-VP3 constructs were able to agglutinate RBC, with FL-PH30 having a HA titer of 100 µg (4HA units) and FL-VP3 a much lower HA titre that could not be reliably determined with the amounts of MC tested here.

The present description enables the incorporation of HA into PH-MicroCubes as an intact full-length membrane protein. In this context, HA is presented at the surface of the crystals and functional as demonstrated by RBC hemagglutination and binding assays.

PH-MicroCubes provide a completely new way of producing full-length membrane proteins in their native membrane environment as opposed to the commonly used soluble constructs, which lack the trans-membrane and cytoplasmic domains By contrast with other platforms (e.g. detergent-solubilised membrane protein; virosome vaccines), this approach also removes the need for detergent solubilisation or chromatography purification of the membrane protein since it is embedded in the crystalline matrix and easily purified by differential centrifugation.

This methodology can be applied in all fields focusing on function protein and membrane protein biology, structure and function such as drug discovery against GPCRs and cell surface receptors; diagnostic; stem cell culture and tissue repair; and vaccine.

Example 2

Heat Stability of the HA Protein in PH30-MicroCubes

Figure 31:
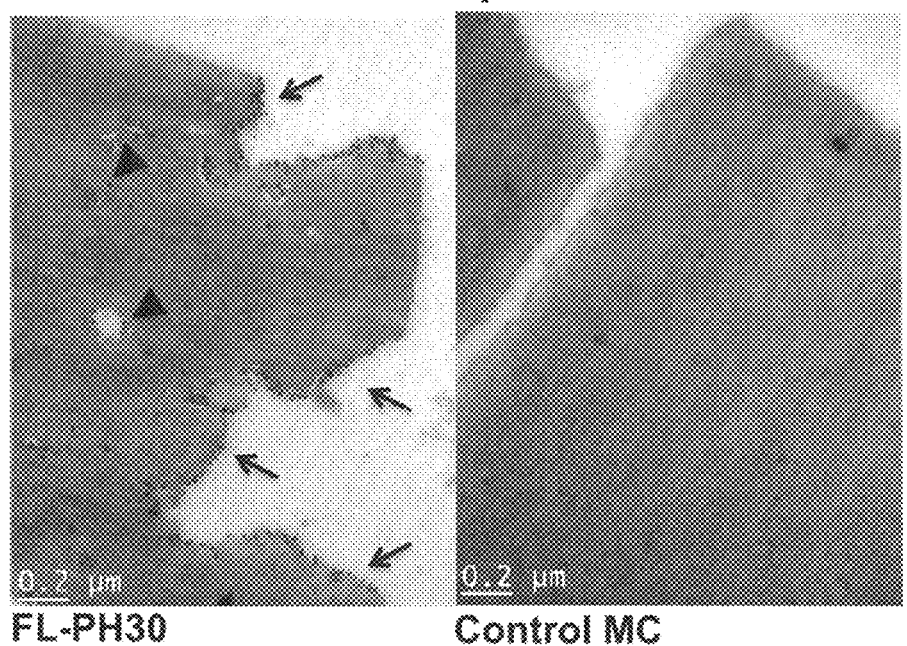
FIG. 31. Detection and localisation of HA protein in microcubes as described in Example 2.
Figure 32:
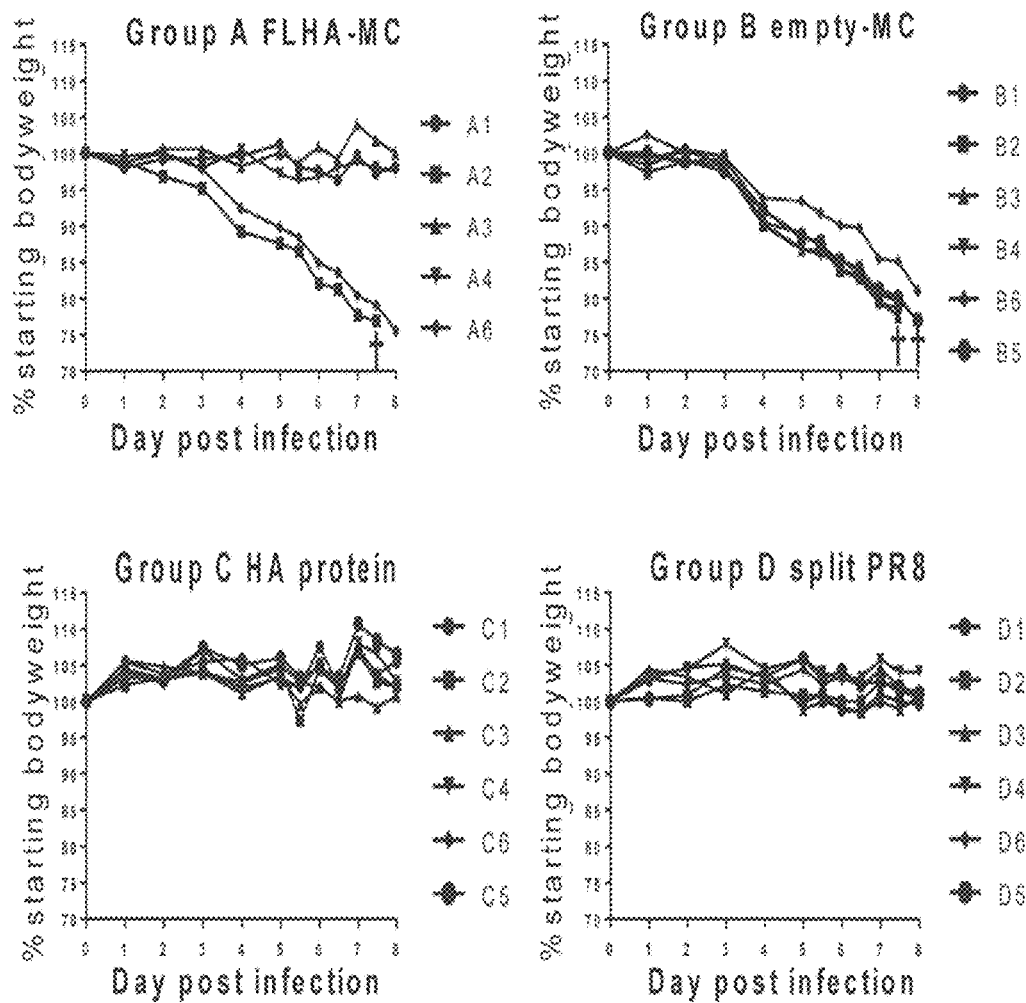
FIG. 32. Protective efficacy of FL30-MC. (A) Survival of balb/c mice (5 mice/group) immunized with 3 doses at one month of interval with FL-MC (GroupA), empty MC (group B), recombinant HA (Group C) or split PR8 vir activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The HA protein is anchored at the surface of MicroCubes and partially embedded into the crystalline matrix which may stabilise the protein compared to its soluble counterpart. Equivalent amounts of HA protein were incubated either in solution or formulated as HA MicroCubes at 4° C., room temperature (~20° C.) and 37° C. Both proteins were stable at a temperature of 4° C. over the 14 days of the experiment. At room temperature and 37° C. the soluble, recombinant HA protein was hardly detectable by Western blot after an incubation of 7 days and the band corresponding to HA was completely lost after 14 days. In contrast, the HA protein in the HA MicroCube samples was clearly detected by Western blot even after 14 days at 37° C. (FIG. 31). The loss compared to storage at 4° C. was estimated to 31% and 70% at 20° C. and 37° C. respectively. Thus HA MicroCubes have an enhanced thermal stability at 20° C. and 37° C. compared to the soluble, recombinant HA protein.

Example 3

Immunogenicity and Protective Capacity of HA Microcubes

Mice Experiment Schedule

Groups of 5-6 mice were immunized subcutaneously with the equivalent dose of 2 µg of HA either with MC-FL-PH30 (group A), empty-MC control (Group B) recombinant HA (Group C), or split Influenza PR8 virus (Group D) at week 0, 4 and 8 and bled prior to each dose to check for antibody responses. Four weeks after the final dose, animals were challenge with PR8 virus and body weight was monitored for 10 days Animals reaching body weight below the pre-determined humane endpoint were euthanized.

Immunogenicity of FL-PH30 in Immunised Mice

A total of 3/5 mice immunised with FL-PH30 mounted high levels of antibodies as tested by ELISA using recombinant PR8 HA as coating antigen. In the control group all the mice immunised with either recombinant HA or split PR8 virus (CSL vaccine) had high levels of anti-HA antibodies. As expected none of the control group mice (empty MC) had antibody raised against HA. This experiment has been repeated and similar results were obtained with 6/6 mice seroconverting in the group immunised with FL-PH30 (equivalent of 2 μg of HA) with levels ranging between 80-25,680.

| Group | Mouse | Titre |
|---|---|---|
| FLPH30 2 μg | A1 | 12800 |
|  | A2 | 80 |
|  | A3 | 25600 |
|  | A4 | 12800 |
|  | A6 | <100 |
| Control MC | B1 | <40 |
|  | B2 | <40 |
|  | B3 | <40 |
|  | B4 | <40 |
|  | B5 | <40 |
|  | B6 | <40 |
| Recombinant HA | C1 | 51,200 |
|  | C2 | 51,200 |
|  | C3 | 51,200 |
|  | C4 | 51,200 |
|  | C5 | 51,200 |
|  | C6 | 12,800 |
| Split PR8 | D1 | 51,200 |
|  | D2 | 204,800 |
|  | D3 | 204,800 |
|  | D4 | 51200 |
|  | D5 | 204,800 |
|  | D6 | 51,200 |

MC-FL-PH30 Protective Efficacy in Mice

To test the capacity of the FL-PH30 to confer protection, mice were challenged with a lethal dose of Influenza PR8 and body weight was monitored for 10 days. None of the animals immunized with the control MC were protected against the lethal challenge as indicated by a quick body weight reduction in this group. In contrast, all mice immunized with the FL-PH30 vaccine (group A) that had high levels of antibodies (mice A1, A2 and A4) were protected when challenged with influenza virus PR8. This indicates that the FL-PH30 vaccine candidate can confer a protective immune response that correlates with the induction of anti-HA humoral immune response. The two mice that were not protected against the lethal viral challenge did not have detectable HA-specific antibodies suggested that they did not receive a sufficient dose of the vaccine.

Many modifications will be apparent to those skilled in the art without departing from the scope of the present description.

TABLE 1

| Sub-classes | Amino acids |
|---|---|
| Acidic | Aspartic acid, Glutamic acid |
| Basic | Noncyclic: Arginine, Lysine; Cyclic: Histidine |

TABLE 1-continued

Amino acid sub-classification

| Sub-classes | Amino acids |
|---|---|
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 2

Exemplary and Preferred Amino Acid Substitutions

| Original residue | Exemplary substitutions | Preferred substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

TABLE 3

| SEQ ID NO: 1 | Vector sequence for pFastBac-Mel-PH14 |
|---|---|
| SEQ ID NO: 2 | Vector sequence for pFastBac-Mel-PH24 |
| SEQ ID NO: 3 | Vector sequence for pFastBac-Mel-PH30 |
| SEQ ID NO: 4 | Nucleotide sequence encoding Env construct with flanking NcoI restriction sites |
| SEQ ID NO: 5 | Protein translation (frame + 3) of SEQ ID NO: 4 |
| SEQ ID NO: 6 | Vector sequence for pFastBac-Mel-PH14-Env |
| SEQ ID NO: 7 | Protein translation for SEQ ID NO: 6 |
| SEQ ID NO: 8 | Vector sequence for pFastBac-Mel-PH24-Env |
| SEQ ID NO: 9 | Protein translation for SEQ ID NO: 8 |
| SEQ ID NO: 10 | Vector sequence for pFastBac-Mel-PH30-Env |
| SEQ ID NO: 11 | Protein translation for SEQ ID NO: 10 |
| SEQ ID NO: 12 | Protein sequence PH14-tag |
| SEQ ID NO: 13 | Protein sequence PH24-tag |
| SEQ ID NO: 14 | Protein sequence PH30-tag |
| SEQ ID NO: 15 | HA PR8 sequence |
| SEQ ID NO: 16 | Melitin sequence |

BIBLIOGRAPHY

Altschul et al., *Nucl. Acids Res.*, 25: 3389-3402, 1997

Arkin and Yourvan, *Proc. Natl. Acad. Sci. USA*, 89: 7811-7815, 1992

Ausubel et al., *Cell Immunol.*, 193(1): 99-107, 1999

Ausubel et al., *Current Protocols in Molecular Biology*, John Wiley & Sons Inc, Chapters 10, 15-16, Unit 19.3 and pages 2.10.1 to 2.10.16, 1994-1998

Bird, *Science* 242:423, 1988
Carter et al., *Bio/Technology* 10:163-167, 1992
Carter et al., *Proc. Nat. Acad. Sci.* 89:4285 1992
Clackson et al., *Nature* 352:624-628, 1991
Coligan et al., *Current Protocols in Protein Science*, John Wiley & Sons, Inc., Chapters 1, 5 and 6, 1995-1997,
Colowick and Kaplan, eds., *Methods In Enzymology*, Academic Press, Inc.
Coulibaly et al., *Nature*, 446: 97-101, 2007
Coulibaly et al., *Proc. Natl. Acad. Sci. U.S.A.* 106(52): 22205-22210, 2009
Dale et al., *Vaccine*, 23(2): 188-197, 2004
Dayhoff et al., *Atlas of Protein Sequence and Structure*, Natl. Biomed. Res. Found., Washington, D.C., Vol. 5, pp. 345-358, 1978
Delgrave et al., *Protein Engineering*, 6: 327-331, 1993
Deveraux et al., *Nucleic Acids Research* 12: 387-395, 1984
Fields and Knipe, eds, *Fundamental Virology*, 2nd Edition, 1991
Fields et al., eds, *Virology*, 3rd Edition, Lippincott-Raven, Philadelphia, Pa., 1996
Gonnet et al., *Science*, 256(5062): 1443-1445, 1992
Hornung et al., *Nat Immunol.*, 9(8): 847-856, 2008
Huston et al., *Proc. Natl. Acad. Sci. USA* 85:5879, 1988
Ijiri et al. *Biomaterials* 30: 4297-4308, 2009
Ikeda et al., *J. Virol.* 75: 988-995, 2001
Ikeda et al., *Proteomics*, 6: 54-66, 2006
Joklik ed., *Virology, 3rd Edition,* 1988
Jones et al., *Nature* 321:522-525, 1986
Kabat et al in *Sequences of Proteins of Immunological Interest*, 5th Ed., US Department of Health and Human Services, PHS, NIH, NIH Publication No. 91-3242, 1991
Kelleher et al., *AIDS*, 20(2): 294-297, 2006
Keoshkerian et al., *J. Med. Virol.* 71(4): 483-491, 2003
Kohler and Milstein, *Nature* 256:495-499, 1975
Kortt et al., *Protein Engineering* 10:423, 1997
Kunkel et al., *Methods in Enzymol.*, 154: 367-382, 1987
Kunkel, *Proc. Natl. Acad. Sci. USA,* 82: 488-492, 1985
Larrick et al., *Bio/Technology* 7:934, 1989
Liu et al., *Proc. Natl. Acad. Sci. USA* 84:3439, 1987
Marks et al., *J. Mol. Biol.* 222:581-597, 1991
Mori et al., *J. Biol. Chem.* 282(23): 17289-17296, 2007
Mori et al., *J. Gen. Virol.* 74(1): 99-102, 1993
Morrison et al., *Proc. Nat. Acad. Sci.* 81:6851, 1984
Newton and Graham eds., *PCR, Introduction to Biotechniques Series,* 2nd ed., Springer Verlag, 1997
Atherton and Shephard (supra), Chapter 9
Padlan et al., *Mol. Immunol.* 28:489-498, 1991
Pedersen et al., *J. Mol. Biol.* 235:959-973, 1994
Presta, *Curr. Op. Struct. Biol.* 2:593-596, 1992
Ream et al., eds., *Molecular Biology Techniques: An Intensive Laboratory Course*, Academic Press, 1998
Reichmann et al., *Nature* 332:323-329, 1988
*Remington's Pharmaceutical Sciences,* 18th Ed., Mack Publishing, Company, Easton, Pa., U.S.A., 1990
Rice-Ficht et al., *Current Opinion in Microbiology,* 13: 106-112, 2010
Roberge et al., *Science,* 269(5221): 202-204, 1995
Sambrook et al., *Molecular Cloning: A Laboratory Manual,* Cold Spring Harbor Laboratory, Cold Spring Harbor, N.Y., Sections 1.101 to 1.104, 16 and 17, 1989
Thomson et al., *Vaccine,* 23(38): 4647-4657, 2005
Tomizuka et al., *Proc. Natl. Acad. Sci. USA* 97: 722-727, 2000
Ward et al., *Nature* 334:544, 1989
Watson et al., *Molecular Biology of the Gene*, Fourth Edition, Benjamin/Cummings, Menlo Park, Calif., 1987
Weir and Blackwell, eds., *Handbook of Experimental Immunology*, Vols. I-IV, Blackwell Scientific Publications, 1986
Winter & Harris, *TIPS* 14: 139, 1993
Yu et al., *Nature,* 453(7193): 415-419, 2008
Zubay, G., *Biochemistry*, third edition, Wm.C. Brown Publishers, 199

---

The invention claimed is:

1. A fusion protein comprising an N-terminal portion and a C-terminal portion, wherein the N-terminal portion is a heterologous protein of interest and the C-terminal portion is a polyhedrin targeting polypeptide, wherein the polyhedrin targeting polypeptide is a cypovirus polyhedrin polypeptide or a cypovirus polyhedrin polypeptide having a deletion of about 1% to about 20% contiguous amino acids at the N-terminus of the full length cypovirus polyhedrin polypeptide.

2. The fusion protein of claim 1, when the polyhedrin targeting polypeptide comprises amino acids 31 to 248, or amino acids 25 to 248, or amino acids 15 to 248 of a cypovirus polyhedrin polypeptide.

3. The fusion protein of claim 1, when the polyhedrin targeting polypeptide is a cypovirus polyhedrin polypeptide having a deletion of about 1% to about 12% contiguous amino acids at the N-terminus of the full length cypovirus polyhedrin polypeptide.

4. The fusion protein of claim 1, wherein the polyhedrin targeting polypeptide is derived from silkworm cypovirus (BmCPV) polyhedrin.

5. The fusion protein of claim 1, wherein the polyhedrin targeting polypeptide comprises the polypeptide sequence set forth in SEQ ID NO: 14 (PH30), SEQ ID NO:13 (PH24) or SEQ ID NO:12 (PH14).

6. The fusion protein of claim 1, wherein the heterologous protein of interest is a membrane protein of interest or an antigen of a disease-causing organism or a condition.

7. The fusion protein of claim 6, wherein the membrane protein of interest is an antigen of a disease-causing organism or a condition.

8. A complex comprising the fusion protein of claim 6 and cypovirus polyhedrin.

9. A polyhedron comprising the fusion protein of claim 1.

10. A composition or kit comprising the polyhedron of claim 9.

11. The composition of claim 10 comprising a physiologically or pharmaceutically acceptable carrier and/or diluent.

12. A nucleic acid molecule encoding and capable of expressing the fusion protein of claim 1, or a vector capable of directing expression of the a polyhedrin targeting polypeptide according to claim 1, and comprising sites for introduction of a heterologous protein of interest.

13. A host cell comprising the fusion protein of claim 1, or the complex of claim 8, or the polyhedron of claim 9 or the nucleic acid molecule of claim 12.

14. A method for eliciting an immune response in a subject to treat or prevent infection by a pathogen or a cancer or other condition, comprising administering to a subject the composition of claim 11 wherein the heterologous protein of interest is an antigen of a disease-causing organism or a condition.

* * * * *

SEQUENCE LISTING

```
<160> NUMBER OF SEQ ID NOS: 16

<210> SEQ ID NO 1
<211> LENGTH: 815
<212> TYPE: DNA
<213> ORGANISM: Artificial Sequence
<220> FEATURE:
<223> OTHER INFORMATION: synthetic

<400> SEQUENCE: 1
ctcgagatga aattcttagt caacgttgcc cttgttttta tggtcgtata catttcttac      60
atctatgcca tggcagcggc ggcggcggca gcggcagcgg acgcgaacaa agactattca     120
atagcgagca atacaactat aacaacagct tgaacggaga agtgagcgtg tgggtatacg     180
catactactc agacgggtct gtactcgtaa tcaacaagaa ctcgcaatac aaggttggca     240
tttcagagac attcaaggca cttaaggaat atcgcaaggg acaacacaac gactcttacg     300
atgagtatga agtgaatcag agcatctact atcctaacgg cggtgacgct cgcaaattcc     360
actcgaatgc taaaccacgc gcgatccaga tcatcttcag ccctagtgtg aatgtgcgta     420
ctatcaagat ggctaaaggt aacgcggtat ccgtgcccga tgagtactta cagcgatctc     480
acccatggga agcgaccgga atcaagtacc gcaagattaa gagagacggg gaaatcgttg     540
gttacagcca ttacttcgaa ctaccccatg aatacaactc catctcccta gcggtaagtg     600
```

| | |
|---|---|
| gtgtacataa gaacccatca tcatacaatg tcggatcagc acataacgta atggacgtct | 660 |
| tccaatcatg cgacttggct ctcagattct gcaaccgcta ctgggccgaa ctcgaattgg | 720 |
| tgaaccacta catttcgccg aacgcctacc catacctcga tatcaacaat catagctatg | 780 |
| gagtagctct gagtaaccgt cagtaataag catgc | 815 |

<210> SEQ ID NO 2
<211> LENGTH: 785
<212> TYPE: DNA
<213> ORGANISM: Artificial Sequence
<220> FEATURE:
<223> OTHER INFORMATION: synthetic

<400> SEQUENCE: 2

| | |
|---|---|
| ctcgagatga aattcttagt caacgttgcc cttgttttta tggtcgtata catttcttac | 60 |
| atctatgcca tggcagcggc ggcggcggca gcggcagcca atacaactat aacaacagct | 120 |
| tgaacggaga agtgagcgtg tgggtatacg catactactc agacgggtct gtactcgtaa | 180 |
| tcaacaagaa ctcgcaatac aaggttggca tttcagagac attcaaggca cttaaggaat | 240 |
| atcgcaaggg acaacacaac gactcttacg atgagtatga agtgaatcag agcatctact | 300 |
| atcctaacgg cggtgacgct cgcaaattcc actcgaatgc taaaccacgc gcgatccaga | 360 |
| tcatcttcag ccctagtgtg aatgtgcgta ctatcaagat ggctaaaggt aacgcggtat | 420 |
| ccgtgcccga tgagtactta cagcgatctc acccatggga agcgaccgga atcaagtacc | 480 |
| gcaagattaa gagagacggg gaaatcgttg gttacagcca ttacttcgaa ctaccccatg | 540 |
| aatacaactc catctcccta gcggtaagtg gtgtacataa gaacccatca tcatacaatg | 600 |
| tcggatcagc acataacgta atggacgtct tccaatcatg cgacttggct ctcagattct | 660 |
| gcaaccgcta ctgggccgaa ctcgaattgg tgaaccacta catttcgccg aacgcctacc | 720 |
| catacctcga tatcaacaat catagctatg gagtagctct gagtaaccgt cagtaataag | 780 |
| catgc | 785 |

<210> SEQ ID NO 3
<211> LENGTH: 767
<212> TYPE: DNA
<213> ORGANISM: Artificial Sequence
<220> FEATURE:
<223> OTHER INFORMATION: synthetic

<400> SEQUENCE: 3

| | |
|---|---|
| ctcgagatga aattcttagt caacgttgcc cttgttttta tggtcgtata catttcttac | 60 |
| atctatgcca tggcagcggc ggcggcggca gcggcagcag cttgaacgga gaagtgagcg | 120 |
| tgtgggtata cgcatactac tcagacgggt ctgtactcgt aatcaacaag aactcgcaat | 180 |
| acaaggttgg catttcagag acattcaagg cacttaagga atatcgcaag ggacaacaca | 240 |
| acgactctta cgatgagtat gaagtgaatc agagcatcta ctatcctaac ggcggtgacg | 300 |
| ctcgcaaatt ccactcgaat gctaaaccac gcgcgatcca gatcatcttc agccctagtg | 360 |
| tgaatgtgcg tactatcaag atggctaaag gtaacgcggt atccgtgccc gatgagtact | 420 |
| tacagcgatc tcacccatgg gaagcgaccg gaatcaagta ccgcaagatt aagagagacg | 480 |
| gggaaatcgt tggttacagc cattacttcg aactacccca tgaatacaac tccatctccc | 540 |
| tagcggtaag tggtgtacat aagaacccat catcatacaa tgtcggatca gcacataacg | 600 |
| taatggacgt cttccaatca tgcgacttgg ctctcagatt ctgcaaccgc tactgggccg | 660 |

| aactcgaatt ggtgaaccac tacatttcgc cgaacgccta cccatacctc gatatcaaca | 720 |
| atcatagcta tggagtagct ctgagtaacc gtcagtaata agcatgc | 767 |

<210> SEQ ID NO 4
<211> LENGTH: 2482
<212> TYPE: DNA
<213> ORGANISM: Artificial Sequence
<220> FEATURE:
<223> OTHER INFORMATION: synthetic

<400> SEQUENCE: 4

| ccatggaaaa attgtgggtc acagtctatt atggggtacc tgtgtggaag gaagcaacca | 60 |
| ccactctatt ttgtgcatca gatgctaaag catatgatac agaggtacat aatgtttggg | 120 |
| ccacacatgc ctgtgtaccc acagacccca acccacaaga agtagtattg gaaaatgtga | 180 |
| cagaaaattt taacatgtgg aaaaataaca tggtagaaca gatgcatgag gatataatca | 240 |
| gtttatggga tcaaagccta aagccatgtg taaaattaac cccactctgt gttactttaa | 300 |
| attgcactga tttgaggaat gttactaata tcaataatag tagtgaggga atgagaggag | 360 |
| aaataaaaaa ctgctctttc aatatcacca caagcataag agataaggtg aagaaagact | 420 |
| atgcactttt ttatagactt gatgtagtac caatagataa tgataatact agctataggt | 480 |
| tgataaattg taatacctca accattacac aggcctgtcc aaaggtatcc tttgagccaa | 540 |
| ttcccataca ttattgtacc ccggctggtt ttgcgattct aaagtgtaaa gataagaagt | 600 |
| tcaatggaac agggccatgt aaaaatgtca gcacagtaca atgtacacat ggaattaggc | 660 |
| cagtagtgtc aactcaactg ctgttaaatg gcagtctagc agaagaagag gtagtaatta | 720 |
| gatctagtaa tttcacagac aatgcaaaaa acataatagt acagttgaaa gaatctgtag | 780 |
| aaattaattg tacaagaccc aacaacaata caaggaaaag tatacatata ggaccaggaa | 840 |
| gagcatttta tacaacagga gacataatag gagatataag acaagcacat tgcaacatta | 900 |
| gtagaacaaa atggaataac actttaaatc aaatagctac aaaattaaaa gaacaatttg | 960 |
| ggaataataa aacaatagtc tttaatcaat cctcaggagg ggacccagaa attgtaatgc | 1020 |
| acagttttaa ttgtggaggg gaattttttct actgtaattc aacacaactg tttaatagta | 1080 |
| cttggaattt taatggtact tggaatttaa cacaatcgaa tggtactgaa ggaaatgaca | 1140 |
| ctatcacact cccatgtaga ataaaacaaa ttataaacat gtggcaagaa gtaggaaaag | 1200 |
| caatgtatgc ccctcccatc agaggacaaa ttagatgttc atcaaatatt acagggctga | 1260 |
| tattaacaag agatggtgga ataaccaca ataatgatac cgagaccttt agacctggag | 1320 |
| gaggagatat gagggacaat tggagaagtg aattatataa atataaagta gtaaaaattg | 1380 |
| aaccattagg agtagcaccc accaaggcaa agagaagagt ggtgcagaga gaaaccggtg | 1440 |
| cagtgggaac aataggagct atgttccttg ggttcttggg agcagcagga agcactatgg | 1500 |
| gcgcagcgtc aataacgctg acggtacagg ccagactatt attgtctggt atagtgcaac | 1560 |
| agcagaacaa cttgctgagg gctattgagg cgcaacagca tctgttgcaa ctcacagtct | 1620 |
| ggggcatcaa gcagctccag gcaagagtcc tggctgtgga agataccta agggatcaac | 1680 |
| agctcctagg gatttggggt tgctctggaa aactcatctg caccactgct gtgccttgga | 1740 |
| atgctagttg gagtaataaa tctctggaac agatttggaa taacatgacc tggatggagt | 1800 |
| gggacagaga aattaacaat tacacaagct taatacactc cttaattgaa gaatcgcaaa | 1860 |
| accagcaaga aaagaatgaa caagaattat tggaattaga taaatgggca agtttgtgga | 1920 |
| attggtttaa cataacaaat tggctgtggt atataaaatt attcataatg atagtaggag | 1980 |

```
gcttggtagg tttaagaata gttttgctg tactttctat agtgaataga gttaggcagg    2040
gatattcacc attatcgttt cagacccacc tcccaatccc gaggggaccc gacaggcccg    2100
aaggaataga agaagaaggt ggagagagag acagagacag atccattcga ttagtgaacg    2160
gatccttagc acttatctgg gacgatctgc ggagcctgtg cctcttcagc taccaccgct    2220
tgagagactt actcttgatt gtaacgagga ttgtggaact tctgggacgc aggggtggg     2280 aagccctcaa atattggtgg aatctcctac agtattggag tcaggaacta agaatagtg     2340 ctgttaactt gctcaatgcc acagccatag cagtagctga ggggacagat agggttatag    2400
aagtattaca agcagcttat agagctattc gccacatacc tagaagaata agacagggct    2460
tggaaaggat tttgctccat gg                                             2482
```

<210> SEQ ID NO 5
<211> LENGTH: 826
<212> TYPE: PRT
<213> ORGANISM: Artificial Sequence
<220> FEATURE:
<223> OTHER INFORMATION: synthetic

<400> SEQUENCE: 5

```
Met Asp Glu Lys Leu Trp Val Thr Val Tyr Tyr Gly Val Pro Val Trp
1               5                   10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Glu Asn Val Thr Glu Asn Phe
    50                  55                  60

Asn Met Trp Lys Asn Asn Met Val Glu Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asn Cys Thr Asp Leu Arg Asn Val Thr Asn Ile Asn
            100                 105                 110

Asn Ser Ser Glu Gly Met Arg Gly Glu Ile Lys Asn Cys Ser Phe Asn
        115                 120                 125

Ile Thr Thr Ser Ile Arg Asp Lys Val Lys Lys Asp Tyr Ala Leu Phe
    130                 135                 140

Tyr Arg Leu Asp Val Val Pro Ile Asp Asn Asp Asn Thr Ser Tyr Arg
145                 150                 155                 160

Leu Ile Asn Cys Asn Thr Ser Thr Ile Thr Gln Ala Cys Pro Lys Val
                165                 170                 175

Ser Phe Glu Pro Ile Pro Ile His Tyr Cys Thr Pro Ala Gly Phe Ala
            180                 185                 190

Ile Leu Lys Cys Lys Asp Lys Lys Phe Asn Gly Thr Gly Pro Cys Lys
        195                 200                 205

Asn Val Ser Thr Val Gln Cys Thr His Gly Ile Arg Pro Val Val Ser
    210                 215                 220

Thr Gln Leu Leu Leu Asn Gly Ser Leu Ala Glu Glu Val Val Ile
225                 230                 235                 240

Arg Ser Ser Asn Phe Thr Asp Asn Ala Lys Asn Ile Ile Val Gln Leu
                245                 250                 255

Lys Glu Ser Val Glu Ile Asn Cys Thr Arg Pro Asn Asn Asn Thr Arg
            260                 265                 270
```

```
Lys Ser Ile His Ile Gly Pro Gly Arg Ala Phe Tyr Thr Thr Gly Asp
            275                 280                 285

Ile Ile Gly Asp Ile Arg Gln Ala His Cys Asn Ile Ser Arg Thr Lys
290                 295                 300

Trp Asn Asn Thr Leu Asn Gln Ile Ala Thr Lys Leu Lys Glu Gln Phe
305                 310                 315                 320

Gly Asn Asn Lys Thr Ile Val Phe Asn Gln Ser Ser Gly Gly Asp Pro
                325                 330                 335

Glu Ile Val Met His Ser Phe Asn Cys Gly Gly Glu Phe Phe Tyr Cys
            340                 345                 350

Asn Ser Thr Gln Leu Phe Asn Ser Thr Trp Asn Phe Asn Gly Thr Trp
        355                 360                 365

Asn Leu Thr Gln Ser Asn Gly Thr Glu Gly Asn Asp Thr Ile Thr Leu
    370                 375                 380

Pro Cys Arg Ile Lys Gln Ile Ile Asn Met Trp Gln Glu Val Gly Lys
385                 390                 395                 400

Ala Met Tyr Ala Pro Pro Ile Arg Gly Gln Ile Arg Cys Ser Ser Asn
                405                 410                 415

Ile Thr Gly Leu Ile Leu Thr Arg Asp Gly Gly Asn Asn His Asn Asn
            420                 425                 430

Asp Thr Glu Thr Phe Arg Pro Gly Gly Gly Asp Met Arg Asp Asn Trp
        435                 440                 445

Arg Ser Glu Leu Tyr Lys Tyr Lys Val Val Lys Ile Glu Pro Leu Gly
    450                 455                 460

Val Ala Pro Thr Lys Ala Lys Arg Arg Val Val Gln Arg Glu Lys Arg
465                 470                 475                 480

Ala Val Gly Thr Ile Gly Ala Met Phe Leu Gly Phe Leu Gly Ala Ala
                485                 490                 495

Gly Ser Thr Met Gly Ala Ala Ser Ile Thr Leu Thr Val Gln Ala Arg
            500                 505                 510

Leu Leu Leu Ser Gly Ile Val Gln Gln Gln Asn Asn Leu Leu Arg Ala
        515                 520                 525

Ile Glu Ala Gln Gln His Leu Leu Gln Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Thr Thr
                565                 570                 575

Ala Val Pro Trp Asn Ala Ser Trp Ser Asn Lys Ser Leu Glu Gln Ile
            580                 585                 590

Trp Asn Asn Met Thr Trp Met Glu Trp Asp Arg Glu Ile Asn Asn Tyr
        595                 600                 605

Thr Ser Leu Ile His Ser Leu Ile Glu Glu Ser Gln Asn Gln Gln Glu
    610                 615                 620

Lys Asn Glu Gln Glu Leu Leu Glu Leu Asp Lys Trp Ala Ser Leu Trp
625                 630                 635                 640

Asn Trp Phe Asn Ile Thr Asn Trp Leu Trp Tyr Ile Lys Leu Phe Ile
                645                 650                 655

Met Ile Val Gly Gly Leu Val Gly Leu Arg Ile Val Phe Ala Val Leu
            660                 665                 670

Ser Ile Val Asn Arg Val Arg Gln Gly Tyr Ser Pro Leu Ser Phe Gln
        675                 680                 685
```

```
Thr His Leu Pro Ile Pro Arg Gly Pro Asp Arg Pro Glu Gly Ile Glu
    690             695                 700

Glu Glu Gly Gly Glu Arg Asp Arg Asp Arg Ser Ile Arg Leu Val Asn
705                 710                 715                 720

Gly Ser Leu Ala Leu Ile Trp Asp Asp Leu Arg Ser Leu Cys Leu Phe
            725                 730                 735

Ser Tyr His Arg Leu Arg Asp Leu Leu Ile Val Thr Arg Ile Val
            740                 745                 750

Glu Leu Leu Gly Arg Arg Gly Trp Glu Ala Leu Lys Tyr Trp Trp Asn
        755                 760                 765

Leu Leu Gln Tyr Trp Ser Gln Glu Leu Lys Asn Ser Ala Val Asn Leu
    770                 775                 780

Leu Asn Ala Thr Ala Ile Ala Val Ala Glu Gly Thr Asp Arg Val Ile
785                 790                 795                 800

Glu Val Leu Gln Ala Ala Tyr Arg Ala Ile Arg His Ile Pro Arg Arg
                805                 810                 815

Ile Arg Gln Gly Leu Glu Arg Ile Leu Leu
            820                 825
```

<210> SEQ ID NO 6
<211> LENGTH: 3291
<212> TYPE: DNA
<213> ORGANISM: Artificial Sequence
<220> FEATURE:
<223> OTHER INFORMATION: Synthetic

<400> SEQUENCE: 6

```
ctcgagatga aattcttagt caacgttgcc cttgttttta tggtcgtata catttcttac     60
atctatgcca tggaaaaatt gtgggtcaca gtctattatg gggtacctgt gtggaaggaa    120
gcaaccacca ctctattttg tgcatcagat gctaaagcat atgatacaga ggtacataat    180
gtttgggcca cacatgcctg tgtacccaca gaccccaacc cacaagaagt agtattggaa    240
aatgtgacag aaaattttaa catgtggaaa ataacatgg tagaacagat gcatgaggat    300
ataatcagtt tatgggatca aagcctaaag ccatgtgtaa aattaacccc actctgtgtt    360
actttaaatt gcactgattt gaggaatgtt actaatatca ataatagtag tgagggaatg    420
agaggagaaa taaaaaactg ctctttcaat atcaccacaa gcataagaga taaggtgaag    480
aaagactatg cacttttttta tagacttgat gtagtaccaa tagataatga taatactagc    540
tataggttga taaattgtaa tacctcaacc attacacagg cctgtccaaa ggtatccttt    600
gagccaattc ccatacatta ttgtaccccg gctggttttg cgattctaaa gtgtaaagat    660
aagaagttca atggaacagg gccatgtaaa aatgtcagca gtacaatg tacacatgga    720 attaggccag tagtgtcaac tcaactgctg ttaaatggca gtctagcaga agaaggta     780 gtaattagat ctagtaattt cacagacaat gcaaaaaaca atatagtaca gttgaaagaa    840
tctgtagaaa ttaattgtac aagacccaac aacaatacaa ggaaaagtat acatatagga    900
ccaggaagag catttatac aacaggagac ataataggag atataagaca agcacattgc    960
aacattagta gaacaaaatg gaataacact ttaaatcaaa tagctacaaa attaaaagaa   1020
caatttggga ataataaaac aatagtcttt aatcaatcct caggagggga cccagaaatt   1080
gtaatgcaca gttttaattg tggagggaa ttttttctact gtaattcaac acaactgttt   1140
aatagtactt ggaattttaa tggtacttgg aatttaacac aatcgaatgg tactgaagga   1200
```

```
aatgacacta tcacactccc atgtagaata aaacaaatta taaacatgtg gcaagaagta    1260
ggaaaagcaa tgtatgcccc tcccatcaga ggacaaatta gatgttcatc aaatattaca    1320
gggctgatat taacaagaga tggtggaaat aaccacaata atgataccga gacctttaga    1380
cctggaggag gagatatgag ggacaattgg agaagtgaat tatataaata taaagtagta    1440
aaaattgaac cattaggagt agcacccacc aaggcaaaga gaagagtggt gcagagagaa    1500
accggtgcag tgggaacaat aggagctatg ttccttgggt tcttgggagc agcaggaagc    1560
actatgggcg cagcgtcaat aacgctgacg gtacaggcca gactattatt gtctggtata    1620
gtgcaacagc agaacaactt gctgagggct attgaggcgc aacagcatct gttgcaactc    1680
acagtctggg gcatcaagca gctccaggca agagtcctgg ctgtggaaag atacctaagg    1740
gatcaacagc tcctagggat ttggggttgc tctggaaaac tcatctgcac cactgctgtg    1800
ccttggaatg ctagttggag taataaatct ctggaacaga tttggaataa catgacctgg    1860
atggagtggg acagagaaat taacaattac acaagcttaa tacactcctt aattgaagaa    1920
tcgcaaaacc agcaagaaaa gaatgaacaa gaattattgg aattagataa atgggcaagt    1980
ttgtggaatt ggtttaacat aacaaattgg ctgtggtata taaaattatt cataatgata    2040
gtaggaggct tggtaggttt aagaatagtt tttgctgtac tttctatagt gaatagagtt    2100
aggcagggat attcaccatt atcgtttcag acccacctcc caatcccgag gggacccgac    2160
aggcccgaag gaatagaaga agaaggtgga gagagagaca gagacagatc cattcgatta    2220
gtgaacggat ccttagcact tatctgggac gatctgcgga gcctgtgcct cttcagctac    2280
caccgcttga gagacttact cttgattgta acgaggattg tggaacttct gggacgcagg    2340
gggtgggaag ccctcaaata ttggtggaat ctcctacagt attggagtca ggaactaaag    2400
aatagtgctg ttaacttgct caatgccaca gccatagcag tagctgaggg gacagatagg    2460
gttatagaag tattacaagc agcttataga gctattcgcc acatacctag aagaataaga    2520
cagggcttgg aaaggatttt gctccatggc agcggcggcg gcggcagcgg cagcggacgc    2580
gaacaaagac tattcaatag cgagcaatac aactataaca acagcttgaa cggagaagtg    2640
agcgtgtggg tatacgcata ctactcagac gggtctgtac tcgtaatcaa caagaactcg    2700
caatacaagg ttggcatttc agagacattc aaggcactta aggaatatcg caagggacaa    2760
cacaacgact cttacgatga gtatgaagtg aatcagagca tctactatcc taacggcggt    2820
gacgctcgca aattccactc gaatgctaaa ccacgcgcga tccagatcat cttcagccct    2880
agtgtgaatg tgcgtactat caagatggct aaaggtaacg cggtatccgt gcccgatgag    2940
tacttacagc gatctcaccc atgggaagcg accggaatca agtaccgcaa gattaagaga    3000
gacggggaaa tcgttggtta cagccattac ttcgaactac ccatgaata caactccatc    3060 tccctagcgg taagtggtgt acataagaac ccatcatcat acaatgtcgg atcagcacat    3120
aacgtaatgg acgtcttcca atcatgcgac ttggctctca gattctgcaa ccgctactgg    3180
gccgaactcg aattggtgaa ccactacatt tcgccgaacg cctacccata cctcgatatc    3240
aacaatcata gctatggagt agctctgagt aaccgtcagt aataagcatg c             3291
```

<210> SEQ ID NO 7
<211> LENGTH: 1091
<212> TYPE: PRT
<213> ORGANISM: Artificial Sequence
<220> FEATURE:
<223> OTHER INFORMATION: synthetic -continued

<400> SEQUENCE: 7

Met Lys Phe Leu Val Asn Val Ala Leu Val Phe Met Val Val Tyr Ile
1               5                   10                  15

Ser Tyr Ile Tyr Ala Met Glu Lys Leu Trp Val Thr Val Tyr Tyr Gly
            20                  25                  30

Val Pro Val Trp Lys Glu Ala Thr Thr Thr Leu Phe Cys Ala Ser Asp
        35                  40                  45

Ala Lys Ala Tyr Asp Thr Glu Val His Asn Val Trp Ala Thr His Ala
    50                  55                  60

Cys Val Pro Thr Asp Pro Asn Pro Gln Glu Val Val Leu Glu Asn Val
65                  70                  75                  80

Thr Glu Asn Phe Asn Met Trp Lys Asn Asn Met Val Glu Gln Met His
                85                  90                  95

Glu Asp Ile Ile Ser Leu Trp Asp Gln Ser Leu Lys Pro Cys Val Lys
            100                 105                 110

Leu Thr Pro Leu Cys Val Thr Leu Asn Cys Thr Asp Leu Arg Asn Val
        115                 120                 125

Thr Asn Ile Asn Asn Ser Ser Glu Gly Met Arg Gly Glu Ile Lys Asn
    130                 135                 140

Cys Ser Phe Asn Ile Thr Thr Ser Ile Arg Asp Lys Val Lys Lys Asp
145                 150                 155                 160

Tyr Ala Leu Phe Tyr Arg Leu Asp Val Val Pro Ile Asp Asn Asp Asn
                165                 170                 175

Thr Ser Tyr Arg Leu Ile Asn Cys Asn Thr Ser Thr Ile Thr Gln Ala
            180                 185                 190

Cys Pro Lys Val Ser Phe Glu Pro Ile Pro Ile His Tyr Cys Thr Pro
        195                 200                 205

Ala Gly Phe Ala Ile Leu Lys Cys Lys Asp Lys Lys Phe Asn Gly Thr
    210                 215                 220

Gly Pro Cys Lys Asn Val Ser Thr Val Gln Cys Thr His Gly Ile Arg
225                 230                 235                 240

Pro Val Val Ser Thr Gln Leu Leu Asn Gly Ser Leu Ala Glu Glu
                245                 250                 255

Glu Val Val Ile Arg Ser Ser Asn Phe Thr Asp Asn Ala Lys Asn Ile
            260                 265                 270

Ile Val Gln Leu Lys Glu Ser Val Glu Ile Asn Cys Thr Arg Pro Asn
        275                 280                 285

Asn Asn Thr Arg Lys Ser Ile His Ile Gly Pro Gly Arg Ala Phe Tyr
    290                 295                 300

Thr Thr Gly Asp Ile Ile Gly Asp Ile Arg Gln Ala His Cys Asn Ile
305                 310                 315                 320

Ser Arg Thr Lys Trp Asn Asn Thr Leu Asn Gln Ile Ala Thr Lys Leu
                325                 330                 335

Lys Glu Gln Phe Gly Asn Asn Lys Thr Ile Val Phe Asn Gln Ser Ser
            340                 345                 350

Gly Gly Asp Pro Glu Ile Val Met His Ser Phe Asn Cys Gly Gly Glu
        355                 360                 365

Phe Phe Tyr Cys Asn Ser Thr Gln Leu Phe Asn Ser Thr Trp Asn Phe
    370                 375                 380

Asn Gly Thr Trp Asn Leu Thr Gln Ser Asn Gly Thr Glu Gly Asn Asp
385                 390                 395                 400

Thr Ile Thr Leu Pro Cys Arg Ile Lys Gln Ile Ile Asn Met Trp Gln
                405                 410                 415

```
Glu Val Gly Lys Ala Met Tyr Ala Pro Ile Arg Gly Gln Ile Arg
            420                 425                 430

Cys Ser Ser Asn Ile Thr Gly Leu Ile Leu Thr Arg Asp Gly Gly Asn
        435                 440                 445

Asn His Asn Asn Asp Thr Glu Thr Phe Arg Pro Gly Gly Gly Asp Met
450                 455                 460

Arg Asp Asn Trp Arg Ser Glu Leu Tyr Lys Tyr Lys Val Val Lys Ile
465                 470                 475                 480

Glu Pro Leu Gly Val Ala Pro Thr Lys Ala Lys Arg Arg Val Val Gln
                485                 490                 495

Arg Glu Thr Gly Ala Val Gly Thr Ile Gly Ala Met Phe Leu Gly Phe
            500                 505                 510

Leu Gly Ala Ala Gly Ser Thr Met Gly Ala Ala Ser Ile Thr Leu Thr
        515                 520                 525

Val Gln Ala Arg Leu Leu Ser Gly Ile Val Gln Gln Gln Asn Asn
    530                 535                 540

Leu Leu Arg Ala Ile Glu Ala Gln Gln His Leu Leu Gln Leu Thr Val
545                 550                 555                 560

Trp Gly Ile Lys Gln Leu Gln Ala Arg Val Leu Ala Val Glu Arg Tyr
                565                 570                 575

Leu Arg Asp Gln Gln Leu Leu Gly Ile Trp Gly Cys Ser Gly Lys Leu
            580                 585                 590

Ile Cys Thr Thr Ala Val Pro Trp Asn Ala Ser Trp Ser Asn Lys Ser
        595                 600                 605

Leu Glu Gln Ile Trp Asn Asn Met Thr Trp Met Glu Trp Asp Arg Glu
    610                 615                 620

Ile Asn Asn Tyr Thr Ser Leu Ile His Ser Leu Ile Glu Glu Ser Gln
625                 630                 635                 640

Asn Gln Gln Glu Lys Asn Glu Gln Glu Leu Leu Glu Leu Asp Lys Trp
                645                 650                 655

Ala Ser Leu Trp Asn Trp Phe Asn Ile Thr Asn Trp Leu Trp Tyr Ile
            660                 665                 670

Lys Leu Phe Ile Met Ile Val Gly Gly Leu Val Gly Leu Arg Ile Val
        675                 680                 685

Phe Ala Val Leu Ser Ile Val Asn Arg Val Arg Gln Gly Tyr Ser Pro
    690                 695                 700

Leu Ser Phe Gln Thr His Leu Pro Ile Pro Arg Gly Pro Asp Arg Pro
705                 710                 715                 720

Glu Gly Ile Glu Glu Glu Gly Gly Glu Arg Asp Arg Asp Arg Ser Ile
                725                 730                 735

Arg Leu Val Asn Gly Ser Leu Ala Leu Ile Trp Asp Asp Leu Arg Ser
            740                 745                 750

Leu Cys Leu Phe Ser Tyr His Arg Leu Arg Asp Leu Leu Leu Ile Val
        755                 760                 765

Thr Arg Ile Val Glu Leu Leu Gly Arg Arg Gly Trp Glu Ala Leu Lys
    770                 775                 780

Tyr Trp Trp Asn Leu Leu Gln Tyr Trp Ser Gln Glu Leu Lys Asn Ser
785                 790                 795                 800

Ala Val Asn Leu Leu Asn Ala Thr Ala Ile Ala Val Ala Glu Gly Thr
                805                 810                 815

Asp Arg Val Ile Glu Val Leu Gln Ala Ala Tyr Arg Ala Ile Arg His
            820                 825                 830
```

```
Ile Pro Arg Arg Ile Arg Gln Gly Leu Glu Arg Ile Leu Leu His Gly
            835                 840                 845

Ser Gly Gly Gly Gly Ser Gly Ser Gly Arg Glu Gln Arg Leu Phe Asn
    850                 855                 860

Ser Glu Gln Tyr Asn Tyr Asn Asn Ser Leu Asn Gly Glu Val Ser Val
865                 870                 875                 880

Trp Val Tyr Ala Tyr Tyr Ser Asp Gly Ser Val Leu Val Ile Asn Lys
                885                 890                 895

Asn Ser Gln Tyr Lys Val Gly Ile Ser Glu Thr Phe Lys Ala Leu Lys
            900                 905                 910

Glu Tyr Arg Lys Gly Gln His Asn Asp Ser Tyr Asp Glu Tyr Glu Val
            915                 920                 925

Asn Gln Ser Ile Tyr Tyr Pro Asn Gly Gly Asp Ala Arg Lys Phe His
    930                 935                 940

Ser Asn Ala Lys Pro Arg Ala Ile Gln Ile Ile Phe Ser Pro Ser Val
945                 950                 955                 960

Asn Val Arg Thr Ile Lys Met Ala Lys Gly Asn Ala Val Ser Val Pro
                965                 970                 975

Asp Glu Tyr Leu Gln Arg Ser His Pro Trp Glu Ala Thr Gly Ile Lys
            980                 985                 990

Tyr Arg Lys Ile Lys Arg Asp Gly Glu Ile Val Gly Tyr Ser His Tyr
            995                1000                1005

Phe Glu Leu Pro His Glu Tyr Asn Ser Ile Ser Leu Ala Val Ser
       1010                1015                1020

Gly Val His Lys Asn Pro Ser Tyr Asn Val Gly Ser Ala His
       1025                1030                1035

Asn Val Met Asp Val Phe Gln Ser Cys Asp Leu Ala Leu Arg Phe
       1040                1045                1050

Cys Asn Arg Tyr Trp Ala Glu Leu Glu Leu Val Asn His Tyr Ile
       1055                1060                1065

Ser Pro Asn Ala Tyr Pro Tyr Leu Asp Ile Asn Asn His Ser Tyr
       1070                1075                1080

Gly Val Ala Leu Ser Asn Arg Gln
       1085                1090

<210> SEQ ID NO 8
<211> LENGTH: 3261
<212> TYPE: DNA
<213> ORGANISM: Artificial Sequence
<220> FEATURE:
<223> OTHER INFORMATION: synthetic

<400> SEQUENCE: 8
ctcgagatga aattcttagt caacgttgcc cttgttttta tggtcgtata catttcttac      60
atctatgcca tggaaaaatt gtgggtcaca gtctattatg gggtacctgt gtggaaggaa     120
gcaaccacca ctctattttg tgcatcagat gctaaagcat atgatacaga ggtacataat     180
gtttgggcca cacatgcctg tgtacccaca gaccccaacc cacaagaagt agtattggaa     240
aatgtgacag aaaattttaa catgtggaaa aataacatgg tagaacagat gcatgaggat     300
ataatcagtt tatgggatca aagcctaaag ccatgtgtaa aattaaccc actctgtgtt      360 actttaaatt gcactgattt gaggaatgtt actaatatca ataatagtag tgagggaatg     420
agaggagaaa taaaaaactg ctctttcaat atcaccacaa gcataagaga taaggtgaaa     480
aaagactatg cactttttta tagacttgat gtagtaccaa tagataatga taatactagc     540
```

```
tataggttga taaattgtaa tacctcaacc attacacagg cctgtccaaa ggtatccttt    600
gagccaattc ccatacatta ttgtaccccg gctggttttg cgattctaaa gtgtaaagat    660
aagaagttca atggaacagg gccatgtaaa aatgtcagca cagtacaatg tacacatgga    720
attaggccag tagtgtcaac tcaactgctg ttaaatggca gtctagcaga agaagaggta    780
gtaattagat ctagtaattt cacagacaat gcaaaaaaca taatagtaca gttgaaagaa    840
tctgtagaaa ttaattgtac aagacccaac aacaatacaa ggaaaagtat acatatagga    900
ccaggaagag catttttatac aacaggagac ataataggag atataagaca agcacattgc    960
aacattagta gaacaaaatg gaataacact ttaaatcaaa tagctacaaa attaaaagaa   1020
caatttggga ataataaaac aatagtcttt aatcaatcct caggagggga cccagaaatt   1080
gtaatgcaca gttttaattg tggaggggaa ttttttctact gtaattcaac acaactgttt   1140
aatagtactt ggaattttaa tggtacttgg aatttaacac aatcgaatgg tactgaagga   1200
aatgacacta tcacactccc atgtagaata aaacaaatta taaacatgtg gcaagaagta   1260
ggaaaagcaa tgtatgcccc tcccatcaga ggacaaatta gatgttcatc aaatattaca   1320
gggctgatat taacaagaga tggtggaaat aaccacaata atgataccga gacctttaga   1380
cctggaggag gagatatgag ggacaattgg agaagtgaat tatataaata taagtagta   1440 aaaattgaac cattaggagt agcacccacc aaggcaaaga gaagagtggt gcagagagaa   1500
accggtgcag tgggaacaat aggagctatg ttccttgggt tcttgggagc agcaggaagc   1560
actatgggcg cagcgtcaat aacgctgacg gtacaggcca gactattatt gtctggtata   1620
gtgcaacagc agaacaactt gctgagggct attgaggcgc aacagcatct gttgcaactc   1680
acagtctggg gcatcaagca gctccaggca agagtcctgg ctgtggaaag atacctaagg   1740
gatcaacagc tcctagggat ttggggttgc tctggaaaac tcatctgcac cactgctgtg   1800
ccttggaatg ctagttggag taataaatct ctggaacaga tttggaataa catgacctgg   1860
atggagtggg acagagaaat taacaattac acaagcttaa tacactcctt aattgaagaa   1920
tcgcaaaacc agcaagaaaa gaatgaacaa gaattattgg aattagataa atgggcaagt   1980
ttgtggaatt ggtttaacat aacaaattgg ctgtggtata taaaattatt cataatgata   2040
gtaggaggct tggtaggttt aagaatagtt tttgctgtac tttctatagt gaatagagtt   2100
aggcagggat attcaccatt atcgtttcag acccacctcc caatcccgag ggacccgac    2160 aggcccgaag gaatagaaga agaaggtgga gagagagaca gagacagatc cattcgatta   2220
gtgaacggat ccttagcact tatctgggac gatctgcgga gcctgtgcct cttcagctac   2280
caccgcttga gagacttact cttgattgta acgaggattg tggaacttct gggacgcagg   2340
gggtgggaag ccctcaaata ttggtggaat ctcctacagt attggagtca ggaactaaag   2400
aatagtgctg ttaacttgct caatgccaca gccatagcag tagctgaggg gacagatagg   2460
gttatagaag tattacaagc agcttataga gcttatcgcc acatacctag aagaataaga   2520
cagggcttgg aaaggatttt gctccatggc agcggcggcg gcggcagcgg cagccaatac   2580
aactataaca acagcttgaa cggagaagtg agcgtgtggg tatacgcata ctactcagac   2640
gggtctgtac tcgtaatcaa caagaactcg caatacaagg ttggcatttc agagacattc   2700
aaggcactta aggaatatcg caagggacaa cacaacgact cttacgatga gtatgaagtg   2760
aatcagagca tctactatcc taacggcggt gacgctcgca aattccactc gaatgctaaa   2820
ccacgcgcga tccagatcat cttcagccct agtgtgaatg tgcgtactat caagatggct   2880
aaaggtaacg cggtatccgt gcccgatgag tacttacagc gatctcaccc atgggaagcg   2940
```

-continued

```
accggaatca agtaccgcaa gattaagaga gacggggaaa tcgttggtta cagccattac    3000
ttcgaactac cccatgaata caactccatc tccctagcgg taagtggtgt acataagaac    3060
ccatcatcat acaatgtcgg atcagcacat aacgtaatgg acgtcttcca atcatgcgac    3120
ttggctctca gattctgcaa ccgctactgg gccgaactcg aattggtgaa ccactacatt    3180
tcgccgaacg cctacccata cctcgatatc aacaatcata gctatggagt agctctgagt    3240
aaccgtcagt aataagcatg c                                              3261
```

<210> SEQ ID NO 9
<211> LENGTH: 1081
<212> TYPE: PRT
<213> ORGANISM: Artificial Sequence
<220> FEATURE:
<223> OTHER INFORMATION: synthetic

<400> SEQUENCE: 9

```
Met Lys Phe Leu Val Asn Val Ala Leu Val Phe Met Val Val Tyr Ile
1               5                   10                  15

Ser Tyr Ile Tyr Ala Met Glu Lys Leu Trp Val Thr Val Tyr Tyr Gly
            20                  25                  30

Val Pro Val Trp Lys Glu Ala Thr Thr Thr Leu Phe Cys Ala Ser Asp
        35                  40                  45

Ala Lys Ala Tyr Asp Thr Glu Val His Asn Val Trp Ala Thr His Ala
    50                  55                  60

Cys Val Pro Thr Asp Pro Asn Pro Gln Glu Val Val Leu Glu Asn Val
65                  70                  75                  80

Thr Glu Asn Phe Asn Met Trp Lys Asn Asn Met Val Glu Gln Met His
                85                  90                  95

Glu Asp Ile Ile Ser Leu Trp Asp Gln Ser Leu Lys Pro Cys Val Lys
            100                 105                 110

Leu Thr Pro Leu Cys Val Thr Leu Asn Cys Thr Asp Leu Arg Asn Val
        115                 120                 125

Thr Asn Ile Asn Asn Ser Ser Glu Gly Met Arg Gly Glu Ile Lys Asn
    130                 135                 140

Cys Ser Phe Asn Ile Thr Thr Ser Ile Arg Asp Lys Val Lys Lys Asp
145                 150                 155                 160

Tyr Ala Leu Phe Tyr Arg Leu Asp Val Val Pro Ile Asp Asn Asp Asn
                165                 170                 175

Thr Ser Tyr Arg Leu Ile Asn Cys Asn Thr Ser Thr Ile Thr Gln Ala
            180                 185                 190

Cys Pro Lys Val Ser Phe Glu Pro Ile Pro Ile His Tyr Cys Thr Pro
        195                 200                 205

Ala Gly Phe Ala Ile Leu Lys Cys Lys Asp Lys Lys Phe Asn Gly Thr
    210                 215                 220

Gly Pro Cys Lys Asn Val Ser Thr Val Gln Cys Thr His Gly Ile Arg
225                 230                 235                 240

Pro Val Val Ser Thr Gln Leu Leu Leu Asn Gly Ser Leu Ala Glu Glu
                245                 250                 255

Glu Val Val Ile Arg Ser Ser Asn Phe Thr Asp Asn Ala Lys Asn Ile
            260                 265                 270

Ile Val Gln Leu Lys Glu Ser Val Glu Ile Asn Cys Thr Arg Pro Asn
        275                 280                 285

Asn Asn Thr Arg Lys Ser Ile His Ile Gly Pro Gly Arg Ala Phe Tyr
    290                 295                 300
```

-continued

```
Thr Thr Gly Asp Ile Ile Gly Asp Ile Arg Gln Ala His Cys Asn Ile
305                 310                 315                 320

Ser Arg Thr Lys Trp Asn Asn Thr Leu Asn Gln Ile Ala Thr Lys Leu
            325                 330                 335

Lys Glu Gln Phe Gly Asn Asn Lys Thr Ile Val Phe Asn Gln Ser Ser
                340                 345                 350

Gly Gly Asp Pro Glu Ile Val Met His Ser Phe Asn Cys Gly Gly Glu
            355                 360                 365

Phe Phe Tyr Cys Asn Ser Thr Gln Leu Phe Asn Ser Thr Trp Asn Phe
            370                 375                 380

Asn Gly Thr Trp Asn Leu Thr Gln Ser Asn Gly Thr Glu Gly Asn Asp
385                 390                 395                 400

Thr Ile Thr Leu Pro Cys Arg Ile Lys Gln Ile Ile Asn Met Trp Gln
                405                 410                 415

Glu Val Gly Lys Ala Met Tyr Ala Pro Pro Ile Arg Gly Gln Ile Arg
                420                 425                 430

Cys Ser Ser Asn Ile Thr Gly Leu Ile Leu Thr Arg Asp Gly Gly Asn
                435                 440                 445

Asn His Asn Asn Asp Thr Glu Thr Phe Arg Pro Gly Gly Gly Asp Met
450                 455                 460

Arg Asp Asn Trp Arg Ser Glu Leu Tyr Lys Tyr Lys Val Val Lys Ile
465                 470                 475                 480

Glu Pro Leu Gly Val Ala Pro Thr Lys Ala Lys Arg Arg Val Val Gln
                485                 490                 495

Arg Glu Thr Gly Ala Val Gly Thr Ile Gly Ala Met Phe Leu Gly Phe
            500                 505                 510

Leu Gly Ala Ala Gly Ser Thr Met Gly Ala Ala Ser Ile Thr Leu Thr
            515                 520                 525

Val Gln Ala Arg Leu Leu Leu Ser Gly Ile Val Gln Gln Gln Asn Asn
530                 535                 540

Leu Leu Arg Ala Ile Glu Ala Gln Gln His Leu Leu Gln Leu Thr Val
545                 550                 555                 560

Trp Gly Ile Lys Gln Leu Gln Ala Arg Val Leu Ala Val Glu Arg Tyr
                565                 570                 575

Leu Arg Asp Gln Gln Leu Leu Gly Ile Trp Gly Cys Ser Gly Lys Leu
            580                 585                 590

Ile Cys Thr Thr Ala Val Pro Trp Asn Ala Ser Trp Ser Asn Lys Ser
            595                 600                 605

Leu Glu Gln Ile Trp Asn Asn Met Thr Trp Met Glu Trp Asp Arg Glu
610                 615                 620

Ile Asn Asn Tyr Thr Ser Leu Ile His Ser Leu Ile Glu Glu Ser Gln
625                 630                 635                 640

Asn Gln Gln Glu Lys Asn Glu Gln Glu Leu Leu Glu Leu Asp Lys Trp
                645                 650                 655

Ala Ser Leu Trp Asn Trp Phe Asn Ile Thr Asn Trp Leu Trp Tyr Ile
            660                 665                 670

Lys Leu Phe Ile Met Ile Val Gly Gly Leu Val Gly Leu Arg Ile Val
            675                 680                 685

Phe Ala Val Leu Ser Ile Val Asn Arg Val Arg Gln Gly Tyr Ser Pro
690                 695                 700

Leu Ser Phe Gln Thr His Leu Pro Ile Pro Arg Gly Pro Asp Arg Pro
705                 710                 715                 720
```

-continued

Glu Gly Ile Glu Glu Glu Gly Gly Glu Arg Asp Arg Asp Arg Ser Ile
            725                 730                 735

Arg Leu Val Asn Gly Ser Leu Ala Leu Ile Trp Asp Ser Leu Arg Ser
740                 745                 750

Leu Cys Leu Phe Ser Tyr His Arg Leu Arg Asp Leu Leu Ile Val
        755                 760                 765

Thr Arg Ile Val Glu Leu Leu Gly Arg Arg Gly Trp Glu Ala Leu Lys
        770                 775                 780

Tyr Trp Trp Asn Leu Leu Gln Tyr Trp Ser Gln Leu Lys Asn Ser
785                 790                 795                 800

Ala Val Asn Leu Leu Asn Ala Thr Ala Ile Ala Val Ala Glu Gly Thr
                805                 810                 815

Asp Arg Val Ile Glu Val Leu Gln Ala Ala Tyr Arg Ala Ile Arg His
                820                 825                 830

Ile Pro Arg Arg Ile Arg Gln Gly Leu Glu Arg Ile Leu Leu His Gly
        835                 840                 845

Ser Gly Gly Gly Gly Ser Gly Ser Gln Tyr Asn Tyr Asn Asn Ser Leu
850                 855                 860

Asn Gly Glu Val Ser Val Trp Val Tyr Ala Tyr Tyr Ser Asp Gly Ser
865                 870                 875                 880

Val Leu Val Ile Asn Lys Asn Ser Gln Tyr Lys Val Gly Ile Ser Glu
                885                 890                 895

Thr Phe Lys Ala Leu Lys Glu Tyr Arg Lys Gly Gln His Asn Asp Ser
                900                 905                 910

Tyr Asp Glu Tyr Glu Val Asn Gln Ser Ile Tyr Tyr Pro Asn Gly Gly
            915                 920                 925

Asp Ala Arg Lys Phe His Ser Asn Ala Lys Pro Arg Ala Ile Gln Ile
        930                 935                 940

Ile Phe Ser Pro Ser Val Asn Val Arg Thr Ile Lys Met Ala Lys Gly
945                 950                 955                 960

Asn Ala Val Ser Val Pro Asp Glu Tyr Leu Gln Arg Ser His Pro Trp
                965                 970                 975

Glu Ala Thr Gly Ile Lys Tyr Arg Lys Ile Lys Arg Asp Gly Glu Ile
            980                 985                 990

Val Gly Tyr Ser His Tyr Phe Glu Leu Pro His Glu Tyr Asn Ser Ile
        995                 1000                1005

Ser Leu Ala Val Ser Gly Val His Lys Asn Pro Ser Ser Tyr Asn
    1010                1015                1020

Val Gly Ser Ala His Asn Val Met Asp Val Phe Gln Ser Cys Asp
    1025                1030                1035

Leu Ala Leu Arg Phe Cys Asn Arg Tyr Trp Ala Glu Leu Glu Leu
    1040                1045                1050

Val Asn His Tyr Ile Ser Pro Asn Ala Tyr Pro Tyr Leu Asp Ile
    1055                1060                1065

Asn Asn His Ser Tyr Gly Val Ala Leu Ser Asn Arg Gln
    1070                1075                1080

<210> SEQ ID NO 10
<211> LENGTH: 3243
<212> TYPE: DNA
<213> ORGANISM: Artificial Sequence
<220> FEATURE:
<223> OTHER INFORMATION: synthetic

```
<400> SEQUENCE: 10
ctcgagatga aattcttagt caacgttgcc cttgttttta tggtcgtata catttcttac      60
atctatgcca tggaaaaatt gtgggtcaca gtctattatg gggtacctgt gtggaaggaa     120
gcaaccacca ctctattttg tgcatcagat gctaaagcat atgatacaga ggtacataat     180
gtttgggcca cacatgcctg tgtacccaca gaccccaacc cacaagaagt agtattggaa     240
aatgtgacag aaaattttaa catgtggaaa ataacatgg tagaacagat gcatgaggat      300
ataatcagtt tatgggatca aagcctaaag ccatgtgtaa aattaacccc actctgtgtt     360
actttaaatt gcactgattt gaggaatgtt actaatatca ataatagtag tgagggaatg     420
agaggagaaa taaaaaactg ctcttttcaat atcaccacaa gcataagaga taaggtgaag    480
aaagactatg cactttttta tagacttgat gtagtaccaa tagataatga taatactagc     540
tataggttga taaattgtaa tacctcaacc attacacagg cctgtccaaa ggtatccttt     600
gagccaattc ccatacatta ttgtaccccg gctggttttg cgattctaaa gtgtaaagat     660
aagaagttca tggaacagg gccatgtaaa aatgtcagca cagtacaatg tacacatgga     720
attaggccag tagtgtcaac tcaactgctg ttaaatggca gtctagcaga agaagaggta     780
gtaattagat ctagtaattt cacagacaat gcaaaaaaca taatagtaca gttgaaagaa     840
tctgtagaaa ttaattgtac aagcccaac aacaatacaa ggaaaagtat acatatagga     900
ccaggaagag catttatac aacaggagac ataataggag atataagaca agcacattgc     960
aacattagta gaacaaaatg gaataacact ttaaatcaaa tagctacaaa attaaaagaa    1020
caatttggga ataataaaac aatagtctttt aatcaatcct caggagggga cccagaaatt    1080
gtaatgcaca gttttaattg tggaggggaa ttttttctact gtaattcaac acaactgttt    1140
aatagtactt ggaattttaa tggtacttgg aatttaacac aatcgaatgg tactgaagga    1200
aatgacacta tcacactccc atgtagaata aaacaaatta taaacatgtg gcaagaagta    1260
ggaaaagcaa tgtatgcccc tcccatcaga ggacaaatta gatgttcatc aaatattaca    1320
gggctgatat taacaagaga tggtggaaat aaccacaata atgataccga gacctttaga    1380
cctggaggag gagatatgag ggacaattgg agaagtgaat tatataaata taaagtagta    1440
aaaattgaac cattaggagt agcacccacc aaggcaaaga gaagagtggt gcagagagaa    1500
accggtgcag tgggaacaat aggagctatg ttccttgggt tcttgggagc agcaggaagc    1560
actatgggcg cagcgtcaat aacgctgacg gtacaggcca gactattatt gtctggtata    1620
gtgcaacagc agaacaactt gctgagggct attgaggcgc aacagcatct gttgcaactc    1680
acagtctggg gcatcaagca gctccaggca agagtcctgg ctgtggaaag atacctaagg    1740
gatcaacagc tcctagggat ttggggttgc tctggaaaac tcatctgcac cactgctgtg    1800
ccttggaatg ctagttggag taataaatct ctggaacaga tttggaataa catgacctgg    1860
atggagtggg acagagaaat taacaattac acaagcttaa tacactcctt aattgaagaa    1920
tcgcaaaacc agcaagaaaa gaatgaacaa gaattattgg aattagataa atgggcaagt    1980
ttgtggaatt ggtttaacat aacaaattgg ctgtggtata taaaattatt cataatgata    2040
gtaggaggct tggtaggttt aagaatagtt tttgctgtac tttctatagt gaatagagtt    2100
aggcagggat attcaccatt atcgtttcag acccacctcc caatcccgag ggacccgac     2160
aggcccgaag aatagaaga agaaggtgga gagagagaca gagacagatc cattcgatta    2220
gtgaacggat ccttagcact tatctgggac gatctgcgga gcctgtgcct cttcagctac    2280
caccgcttga gagacttact cttgattgta acgaggattg tggaacttct ggacgcagg    2340
```

-continued

```
gggtgggaag ccctcaaata ttggtggaat ctcctacagt attggagtca ggaactaaag   2400
aatagtgctg ttaacttgct caatgccaca gccatagcag tagctgaggg gacagatagg   2460
gttatagaag tattacaagc agcttataga gctattcgcc acatacctag aagaataaga   2520
cagggcttgg aaaggatttt gctccatggc agcggcggcg gcggcagcgg cagcagcttg   2580
aacggagaag tgagcgtgtg ggtatacgca tactactcag acgggtctgt actcgtaatc   2640
aacaagaact cgcaatacaa ggttggcatt tcagagacat tcaaggcact taaggaatat   2700
cgcaagggac aacacaacga ctcttacgat gagtatgaag tgaatcagag catctactat   2760
cctaacggcg gtgacgctcg caaattccac tcgaatgcta accacgcgc gatccagatc    2820 atcttcagcc ctagtgtgaa tgtgcgtact atcaagatgg ctaaaggtaa cgcggtatcc   2880
gtgcccgatg agtacttaca gcatctcac ccatgggaag cgaccggaat caagtaccgc    2940
aagattaaga gagacgggga aatcgttggt tacagccatt acttcgaact accccatgaa   3000
tacaactcca tctccctagc ggtaagtggt gtacataaga acccatcatc atacaatgtc   3060
ggatcagcac ataacgtaat ggacgtcttc caatcatgcg acttggctct cagattctgc   3120
aaccgctact gggccgaact cgaattggtg aaccactaca tttcgccgaa cgcctaccca   3180
tacctcgata tcaacaatca tagctatgga gtagctctga gtaaccgtca gtaataagca   3240
tgc                                                                 3243
```

<210> SEQ ID NO 11
<211> LENGTH: 1076
<212> TYPE: PRT
<213> ORGANISM: Artificial Sequence
<220> FEATURE:
<223> OTHER INFORMATION: synthetic

<400> SEQUENCE: 11

```
Met Lys Phe Leu Val Asn Val Ala Leu Val Phe Met Val Val Tyr Ile
1               5                   10                  15

Ser Tyr Ile Tyr Ala Met Asp Glu Lys Leu Trp Val Thr Val Tyr Tyr
            20                  25                  30

Gly Val Pro Val Trp Lys Glu Ala Thr Thr Thr Leu Phe Cys Ala Ser
        35                  40                  45

Asp Ala Lys Ala Tyr Asp Thr Glu Val His Asn Val Trp Ala Thr His
    50                  55                  60

Ala Cys Val Pro Thr Asp Pro Asn Pro Gln Glu Val Val Leu Glu Asn
65                  70                  75                  80

Val Thr Glu Asn Phe Asn Met Trp Lys Asn Asn Met Val Glu Gln Met
                85                  90                  95

His Glu Asp Ile Ile Ser Leu Trp Asp Gln Ser Leu Lys Pro Cys Val
            100                 105                 110

Lys Leu Thr Pro Leu Cys Val Thr Leu Asn Cys Thr Asp Leu Arg Asn
        115                 120                 125

Val Thr Asn Ile Asn Asn Ser Ser Glu Gly Met Arg Gly Glu Ile Lys
    130                 135                 140

Asn Cys Ser Phe Asn Ile Thr Thr Ser Ile Arg Asp Lys Val Lys Lys
145                 150                 155                 160

Asp Tyr Ala Leu Phe Tyr Arg Leu Asp Val Val Pro Ile Asp Asn Asp
                165                 170                 175

Asn Thr Ser Tyr Arg Leu Ile Asn Cys Asn Thr Ser Thr Ile Thr Gln
            180                 185                 190
```

-continued

```
Ala Cys Pro Lys Val Ser Phe Glu Pro Ile Pro Ile His Tyr Cys Thr
        195                 200                 205
Pro Ala Gly Phe Ala Ile Leu Lys Cys Lys Asp Lys Lys Phe Asn Gly
    210                 215                 220
Thr Gly Pro Cys Lys Asn Val Ser Thr Val Gln Cys Thr His Gly Ile
225                 230                 235                 240
Arg Pro Val Val Ser Thr Gln Leu Leu Leu Asn Gly Ser Leu Ala Glu
                245                 250                 255
Glu Glu Val Val Ile Arg Ser Ser Asn Phe Thr Asp Asn Ala Lys Asn
            260                 265                 270
Ile Ile Val Gln Leu Lys Glu Ser Val Glu Ile Asn Cys Thr Arg Pro
        275                 280                 285
Asn Asn Asn Thr Arg Lys Ser Ile His Ile Gly Pro Gly Arg Ala Phe
    290                 295                 300
Tyr Thr Thr Gly Asp Ile Ile Gly Asp Ile Arg Gln Ala His Cys Asn
305                 310                 315                 320
Ile Ser Arg Thr Lys Trp Asn Asn Thr Leu Asn Gln Ile Ala Thr Lys
                325                 330                 335
Leu Lys Glu Gln Phe Gly Asn Asn Lys Thr Ile Val Phe Asn Gln Ser
            340                 345                 350
Ser Gly Gly Asp Pro Glu Ile Val Met His Ser Phe Asn Cys Gly Gly
        355                 360                 365
Glu Phe Phe Tyr Cys Asn Ser Thr Gln Leu Phe Asn Ser Thr Trp Asn
    370                 375                 380
Phe Asn Gly Thr Trp Asn Leu Thr Gln Ser Asn Gly Thr Glu Gly Asn
385                 390                 395                 400
Asp Thr Ile Thr Leu Pro Cys Arg Ile Lys Gln Ile Ile Asn Met Trp
                405                 410                 415
Gln Glu Val Gly Lys Ala Met Tyr Ala Pro Pro Ile Arg Gly Gln Ile
            420                 425                 430
Arg Cys Ser Ser Asn Ile Thr Gly Leu Ile Leu Thr Arg Asp Gly Gly
        435                 440                 445
Asn Asn His Asn Asn Asp Thr Glu Thr Phe Arg Pro Gly Gly Gly Asp
    450                 455                 460
Met Arg Asp Asn Trp Arg Ser Glu Leu Tyr Lys Tyr Lys Val Val Lys
465                 470                 475                 480
Ile Glu Pro Leu Gly Val Ala Pro Thr Lys Ala Lys Arg Arg Val Val
                485                 490                 495
Gln Arg Glu Thr Gly Ala Val Gly Thr Ile Gly Ala Met Phe Leu Gly
            500                 505                 510
Phe Leu Gly Ala Ala Gly Ser Thr Met Gly Ala Ala Ser Ile Thr Leu
        515                 520                 525
Thr Val Gln Ala Arg Leu Leu Leu Ser Gly Ile Val Gln Gln Gln Asn
    530                 535                 540
Asn Leu Leu Arg Ala Ile Glu Ala Gln Gln His Leu Leu Gln Leu Thr
545                 550                 555                 560
Val Trp Gly Ile Lys Gln Leu Gln Ala Arg Val Leu Ala Val Glu Arg
                565                 570                 575
Tyr Leu Arg Asp Gln Gln Leu Leu Gly Ile Trp Gly Cys Ser Gly Lys
            580                 585                 590
Leu Ile Cys Thr Thr Ala Val Pro Trp Asn Ala Ser Trp Ser Asn Lys
        595                 600                 605
```

-continued

```
Ser Leu Glu Gln Ile Trp Asn Asn Met Thr Trp Met Glu Trp Asp Arg
610                 615                 620
Glu Ile Asn Asn Tyr Thr Ser Leu Ile His Ser Leu Ile Glu Glu Ser
625                 630                 635                 640
Gln Asn Gln Gln Glu Lys Asn Glu Gln Glu Leu Leu Glu Leu Asp Lys
            645                 650                 655
Trp Ala Ser Leu Trp Asn Trp Phe Asn Ile Thr Asn Trp Leu Trp Tyr
            660                 665                 670
Ile Lys Leu Phe Ile Met Ile Val Gly Leu Val Gly Leu Arg Ile
            675                 680                 685
Val Phe Ala Val Leu Ser Ile Val Asn Arg Val Arg Gln Gly Tyr Ser
690                 695                 700
Pro Leu Ser Phe Gln Thr His Leu Pro Ile Pro Arg Gly Pro Asp Arg
705                 710                 715                 720
Pro Glu Gly Ile Glu Glu Gly Gly Glu Arg Asp Arg Asp Arg Ser
                725                 730                 735
Ile Arg Leu Val Asn Gly Ser Leu Ala Leu Ile Trp Asp Asp Leu Arg
            740                 745                 750
Ser Leu Cys Leu Phe Ser Tyr His Arg Leu Arg Asp Leu Leu Leu Ile
            755                 760                 765
Val Thr Arg Ile Val Glu Leu Leu Gly Arg Arg Gly Trp Glu Ala Leu
770                 775                 780
Lys Tyr Trp Trp Asn Leu Leu Gln Tyr Trp Ser Gln Glu Leu Lys Asn
785                 790                 795                 800
Ser Ala Val Asn Leu Leu Asn Ala Thr Ala Ile Ala Val Ala Glu Gly
            805                 810                 815
Thr Asp Arg Val Ile Glu Val Leu Gln Ala Ala Tyr Arg Ala Ile Arg
            820                 825                 830
His Ile Pro Arg Arg Ile Arg Gln Gly Leu Glu Arg Ile Leu Leu His
            835                 840                 845
Gly Ser Gly Gly Gly Ser Gly Ser Ser Leu Asn Gly Glu Val Ser
850                 855                 860
Val Trp Val Tyr Ala Tyr Tyr Ser Asp Gly Ser Val Leu Val Ile Asn
865                 870                 875                 880
Lys Asn Ser Gln Tyr Lys Val Gly Ile Ser Glu Thr Phe Lys Ala Leu
            885                 890                 895
Lys Glu Tyr Arg Lys Gly Gln His Asn Asp Ser Tyr Asp Glu Tyr Glu
            900                 905                 910
Val Asn Gln Ser Ile Tyr Tyr Pro Asn Gly Gly Asp Ala Arg Lys Phe
            915                 920                 925
His Ser Asn Ala Lys Pro Arg Ala Ile Gln Ile Phe Ser Pro Ser
930                 935                 940
Val Asn Val Arg Thr Ile Lys Met Ala Lys Gly Asn Ala Val Ser Val
945                 950                 955                 960
Pro Asp Glu Tyr Leu Gln Arg Ser His Pro Trp Glu Ala Thr Gly Ile
            965                 970                 975
Lys Tyr Arg Lys Ile Lys Arg Asp Gly Glu Ile Val Gly Tyr Ser His
            980                 985                 990
Tyr Phe Glu Leu Pro His Glu Tyr Asn Ser Ile Ser Leu Ala Val Ser
            995                 1000                1005
Gly Val His Lys Asn Pro Ser Ser Tyr Asn Val Gly Ser Ala His
    1010                1015                1020
```

```
Asn Val Met Asp Val Phe Gln Ser Cys Asp Leu Ala Leu Arg Phe
    1025                1030                1035

Cys Asn Arg Tyr Trp Ala Glu Leu Glu Leu Val Asn His Tyr Ile
    1040                1045                1050

Ser Pro Asn Ala Tyr Pro Tyr Leu Asp Ile Asn Asn His Ser Tyr
    1055                1060                1065

Gly Val Ala Leu Ser Asn Arg Gln
    1070                1075

<210> SEQ ID NO 12
<211> LENGTH: 235
<212> TYPE: PRT
<213> ORGANISM: Artificial Sequence
<220> FEATURE:
<223> OTHER INFORMATION: synthetic

<400> SEQUENCE: 12

Gly Arg Glu Gln Arg Leu Phe Asn Ser Glu Gln Tyr Asn Tyr Asn
1               5                   10                  15

Ser Leu Asn Gly Glu Val Ser Val Trp Val Tyr Ala Tyr Tyr Ser Asp
            20                  25                  30

Gly Ser Val Leu Val Ile Asn Lys Asn Ser Gln Tyr Lys Val Gly Ile
            35                  40                  45

Ser Glu Thr Phe Lys Ala Leu Lys Glu Tyr Arg Lys Gly Gln His Asn
    50                  55                  60

Asp Ser Tyr Asp Glu Tyr Glu Val Asn Gln Ser Ile Tyr Tyr Pro Asn
65                  70                  75                  80

Gly Gly Asp Ala Arg Lys Phe His Ser Asn Ala Lys Pro Arg Ala Ile
                85                  90                  95

Gln Ile Ile Phe Ser Pro Ser Val Asn Val Arg Thr Ile Lys Met Ala
            100                 105                 110

Lys Gly Asn Ala Val Ser Val Pro Asp Glu Tyr Leu Gln Arg Ser His
            115                 120                 125

Pro Trp Glu Ala Thr Gly Ile Lys Tyr Arg Lys Ile Lys Arg Asp Gly
    130                 135                 140

Glu Ile Val Gly Tyr Ser His Tyr Phe Glu Leu Pro His Glu Tyr Asn
145                 150                 155                 160

Ser Ile Ser Leu Ala Val Ser Gly Val His Lys Asn Pro Ser Ser Tyr
                165                 170                 175

Asn Val Gly Ser Ala His Asn Val Met Asp Val Phe Gln Ser Cys Asp
            180                 185                 190

Leu Ala Leu Arg Phe Cys Asn Arg Tyr Trp Ala Glu Leu Glu Leu Val
            195                 200                 205

Asn His Tyr Ile Ser Pro Asn Ala Tyr Pro Tyr Leu Asp Ile Asn Asn
    210                 215                 220

His Ser Tyr Gly Val Ala Leu Ser Asn Arg Gln
225                 230                 235

<210> SEQ ID NO 13
<211> LENGTH: 225
<212> TYPE: PRT
<213> ORGANISM: Artificial Sequence
<220> FEATURE:
<223> OTHER INFORMATION: synthetic
```

-continued

```
<400> SEQUENCE: 13

Gln Tyr Asn Tyr Asn Asn Ser Leu Asn Gly Glu Val Ser Val Trp Val
1               5                   10                  15

Tyr Ala Tyr Tyr Ser Asp Gly Ser Val Leu Val Ile Asn Lys Asn Ser
            20                  25                  30

Gln Tyr Lys Val Gly Ile Ser Glu Thr Phe Lys Ala Leu Lys Glu Tyr
        35                  40                  45

Arg Lys Gly Gln His Asn Asp Ser Tyr Asp Tyr Glu Val Asn Gln
    50                  55                  60

Ser Ile Tyr Tyr Pro Asn Gly Gly Asp Ala Arg Lys Phe His Ser Asn
65                  70                  75                  80

Ala Lys Pro Arg Ala Ile Gln Ile Ile Phe Ser Pro Ser Val Asn Val
                85                  90                  95

Arg Thr Ile Lys Met Ala Lys Gly Asn Ala Val Ser Val Pro Asp Glu
            100                 105                 110

Tyr Leu Gln Arg Ser His Pro Trp Glu Ala Thr Gly Ile Lys Tyr Arg
        115                 120                 125

Lys Ile Lys Arg Asp Gly Glu Ile Val Gly Tyr Ser His Tyr Phe Glu
130                 135                 140

Leu Pro His Glu Tyr Asn Ser Ile Ser Leu Ala Val Ser Gly Val His
145                 150                 155                 160

Lys Asn Pro Ser Ser Tyr Asn Val Gly Ser Ala His Asn Val Met Asp
                165                 170                 175

Val Phe Gln Ser Cys Asp Leu Ala Leu Arg Phe Cys Asn Arg Tyr Trp
            180                 185                 190

Ala Glu Leu Glu Leu Val Asn His Tyr Ile Ser Pro Asn Ala Tyr Pro
        195                 200                 205

Tyr Leu Asp Ile Asn Asn His Ser Tyr Gly Val Ala Leu Ser Asn Arg
    210                 215                 220

Gln
225

<210> SEQ ID NO 14
<211> LENGTH: 219
<212> TYPE: PRT
<213> ORGANISM: Artificial Sequence
<220> FEATURE:
<223> OTHER INFORMATION: synthetic

<400> SEQUENCE: 14

Ser Leu Asn Gly Glu Val Ser Val Trp Val Tyr Ala Tyr Tyr Ser Asp
1               5                   10                  15

Gly Ser Val Leu Val Ile Asn Lys Asn Ser Gln Tyr Lys Val Gly Ile
            20                  25                  30

Ser Glu Thr Phe Lys Ala Leu Lys Glu Tyr Arg Lys Gly Gln His Asn
        35                  40                  45

Asp Ser Tyr Asp Glu Tyr Glu Val Asn Gln Ser Ile Tyr Tyr Pro Asn
    50                  55                  60

Gly Gly Asp Ala Arg Lys Phe His Ser Asn Ala Lys Pro Arg Ala Ile
65                  70                  75                  80

Gln Ile Ile Phe Ser Pro Ser Val Asn Val Arg Thr Ile Lys Met Ala
                85                  90                  95

Lys Gly Asn Ala Val Ser Val Pro Asp Glu Tyr Leu Gln Arg Ser His
            100                 105                 110
```

```
Pro Trp Glu Ala Thr Gly Ile Lys Tyr Arg Lys Ile Lys Arg Asp Gly
        115                 120                 125

Glu Ile Val Gly Tyr Ser His Tyr Phe Glu Leu Pro His Glu Tyr Asn
    130                 135                 140

Ser Ile Ser Leu Ala Val Ser Gly Val His Lys Asn Pro Ser Ser Tyr
145                 150                 155                 160

Asn Val Gly Ser Ala His Asn Val Met Asp Val Phe Gln Ser Cys Asp
                165                 170                 175

Leu Ala Leu Arg Phe Cys Asn Arg Tyr Trp Ala Glu Leu Glu Leu Val
            180                 185                 190

Asn His Tyr Ile Ser Pro Asn Ala Tyr Pro Tyr Leu Asp Ile Asn Asn
        195                 200                 205

His Ser Tyr Gly Val Ala Leu Ser Asn Arg Gln
    210                 215
```

<210> SEQ ID NO 15
<211> LENGTH: 1654
<212> TYPE: DNA
<213> ORGANISM: Artificial Sequence
<220> FEATURE:
<223> OTHER INFORMATION: synthetic

<400> SEQUENCE: 15

```
ccatggatac aatctgtatt ggataccacg ccaataactc aaccgacact gtggatactg    60
tcctcgaaaa gaacgtgacg gtcactcaca gtgtcaattt gttggaagat agccacaatg   120
gtaaactgtg cagactgaaa ggcattgccc ctctgcaact cggaaagtgt aacattgctg   180
gatggctgtt gggtaacccc gagtgcgacc cacttctccc tgtccgctcg tggtcctaca   240
tcgtggagac tcccaatagc gagaatggta tttgttaccc aggcgacttt atcgactatg   300
aggagctgcg cgagcagctc tcatcggtca gctcattcga gaggtttgag atctttccca   360
aggaatcgag ctggccaaat cataacacca acggagttac tgcagcttgc tcccacgagg   420
gaaaatcttc gttctatcgt aatttgttgt ggctgactga aaaggaggga agttacccga   480
agttgaaaaa ctcctacgtc aataagaagg gtaagaagt gctggttctc tgggcatcc    540 accatcctcc gaattccaag gaacaacaga acatctacca gaacgaaaat gcttatgtgt   600
ccgtggttac ctccaactac aacaggcgct tcacaccaga gatcgctgag cgtcctaaag   660
tccgcgacca ggcgggtcgc atgaattact actggaccct gctgaagccg ggtgatacta   720
ttatcttcga ggctaacggt aacctcatag cgcccatgta tgctttcgcc ttgtcaagag   780
gttttggcag tggaatcatt acctctaacg cgtctatgca tgagtgcaat actaagtgcc   840
agacacctct cggagctata aacagctccc ttccctatca aaacatccac ccagtcacca   900
taggagaatg tcctaagtat gtacgctccg ccaagttgag gatggtaacg ggcttgcgta   960
acacaccctc gatccagagt aggggtctgt tcggagcaat tgcaggcttc atcgagggcg  1020
gttggacggg tatgatcgat ggctggtatg ctaccacca tcaaaacgag cagggcagtg  1080
gatacgccgc agatcagaag tctacacaaa acgctatcaa tggaattacc aacaaggtta  1140
ataccgttat cgaaaagatg aatatacagt tcacagccgt gggcaaagaa ttcaacaagt  1200
tggaaaaacg tatggaaaac cttaacaaga agtggatga cggttttctc gacatctgga  1260
cctacaacgc agagcttctg gtacttcttg agaacgaaag aaccctggac ttccacgact  1320
cgaacgtgaa gaatctttac gaaaaggtaa agagtcaact caagaacaac gctaagagaa  1380
ttggtaacgg ttgtttcgaa ttctatcaca gtgcgacaa cgaatgcatg gagtccgttc  1440
```

```
gtaacggtac gtacgactac ccaaagtaca gcgaggagag caaactgaac agagaaaaag    1500
tagatggcgt caaactcgaa tcaatgggca tataccagat cctggcgatc tactctacgg    1560
ttgcctcttc tctcgtgctg cttgtgtcat tgggagccat aagtttctgg atgtgcagca    1620
acggctcact gcaatgtcgt atttgcatcc atgg                                1654
```

<210> SEQ ID NO 16
<211> LENGTH: 22
<212> TYPE: PRT
<213> ORGANISM: Artificial Sequence
<220> FEATURE:
<223> OTHER INFORMATION: synthetic

<400> SEQUENCE: 16

```
Met Lys Phe Leu Val Asn Val Ala Leu Val Phe Met Val Val Tyr Ile
1               5                   10                  15

Ser Tyr Ile Tyr Ala Met
            20
```